United States Patent
Chan et al.

(10) Patent No.: US 11,083,755 B2
(45) Date of Patent: Aug. 10, 2021

(54) FACTORS AND CELLS THAT PROVIDE FOR INDUCTION OF BONE, BONE MARROW, AND CARTILAGE

(71) Applicant: The Board of Trustees of the Leland Stanford Junior University, Stanford, CA (US)

(72) Inventors: Charles K. F. Chan, Redwood City, CA (US); Irving L. Weissman, Stanford, CA (US); Michael T. Longaker, Atherton, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/538,894

(22) PCT Filed: Jan. 6, 2016

(86) PCT No.: PCT/US2016/012347
§ 371 (c)(1),
(2) Date: Jun. 22, 2017

(87) PCT Pub. No.: WO2016/112111
PCT Pub. Date: Jul. 14, 2016

(65) Prior Publication Data
US 2017/0360838 A1    Dec. 21, 2017

Related U.S. Application Data

(60) Provisional application No. 62/101,282, filed on Jan. 8, 2015.

(51) Int. Cl.
| | |
|---|---|
| A61K 35/28 | (2015.01) |
| A61L 27/38 | (2006.01) |
| A61K 35/32 | (2015.01) |
| A61L 27/54 | (2006.01) |
| A61K 38/17 | (2006.01) |
| A61P 19/08 | (2006.01) |
| A61P 19/02 | (2006.01) |
| A61K 38/18 | (2006.01) |
| C12N 5/0775 | (2010.01) |

(52) U.S. Cl.
CPC .............. *A61K 35/28* (2013.01); *A61K 35/32* (2013.01); *A61K 38/1709* (2013.01); *A61K 38/1875* (2013.01); *A61L 27/3834* (2013.01); *A61L 27/54* (2013.01); *A61P 19/02* (2018.01); *A61P 19/08* (2018.01); *C12N 5/0668* (2013.01); *A61L 2300/252* (2013.01); *A61L 2430/02* (2013.01); *A61L 2430/06* (2013.01); *C12N 2501/155* (2013.01); *C12N 2501/165* (2013.01); *C12N 2501/415* (2013.01)

(58) Field of Classification Search
CPC .... A61K 35/28; A61K 38/1709; A61K 35/32; A61L 27/3834; A61L 27/54; A61L 2300/252; A61L 2430/06; A61L 2430/02
See application file for complete search history.

(56) References Cited

U.S. PATENT DOCUMENTS

| | | | |
|---|---|---|---|
| 2011/0104230 A1 | 5/2011 | Mousa et al. | |
| 2014/0370111 A1* | 12/2014 | Boyan ................. | C12N 5/0655 424/493 |

FOREIGN PATENT DOCUMENTS

| | | |
|---|---|---|
| WO | 1999/046366 | 9/1999 |
| WO | 2014/093836 A1 | 6/2014 |

OTHER PUBLICATIONS

Koga et al. Comparison of mesenchymal tissues-derived stem cells for in vivo chondrogenesis: suitable conditions for cell therapy of cartilage defects in rabbit. Cell Tissue Res (2008) 333:207-215 (Year: 2008).*
Mesimaki et al. Novel maxillary reconstruction with ectopic bone formation by GMP adipose stem cells. Int. J. Oral Maxillofac. Surg. 2009; 38: 201-209 (Year: 2009).*
Fan et al. Adipose-Derived Stem Cells and BMP-2 Delivery in Chitosan-Based 3D Constructs to Enhance Bone Regeneration in a Rat Mandibular Defect Model. Tissue Engineering: Part A vol. 20, Nos. 15 and 16, p. 2169-2179 (Year: 2014).*
Shi et al. Adipose-Derived Stem Cells Combined with a Demineralized Cancellous Bone Substrate for Bone Regeneration. Tissue Engineering: Part A. vol. 18, Nos. 13 and 14. p. 1-9 (Year: 2012).*
Zhang et al. A signal-amplification circuit between miR-218 and Wnt/β-catenin signal promotes human adipose tissue-derived stem cells osteogenic differentiation. Bone 58 (2014) 59-66 (Year: 2014).*
Levi et al. Adipose Derived Stromal Cells for Skeletal Regenerative Medicine. Stem Cells. Apr. 2011; 29(4): 576-582 (Year: 2011).*
Santos et al. WNT5A induces osteogenic differentiation of human adipose stem cells via rho-associated kinase Rock. Cytotherapy, 2010; 12: 924-932 (Year: 2010).*

(Continued)

*Primary Examiner* — Taeyoon Kim
(74) *Attorney, Agent, or Firm* — Pamela J. Sherwood; Bozicevic, Field & Francis LLP

(57) ABSTRACT

Methods, compositions and kits for producing functional chondrocytes, skeletal cells, bone marrow stromal cells, and progenitor cells thereof are provided. These methods, compositions and kits find use in producing chondrocytes, osteoblasts, stromal cells, and progenitor cells thereof in vivo, or in vitro for transplantation, for experimental evaluation, as a source of lineage- and cell-specific products, and the like, for example for use in treating human disorders of the cartilage, bone and hematopoietic system. In some embodiments, specific combinations of protein factors are identified for reprogramming non-skeletal cells into bones, hematopoietic stroma, and chondrocytes, which may be provided in vitro or in vivo.

19 Claims, 44 Drawing Sheets
(44 of 44 Drawing Sheet(s) Filed in Color)

(56) References Cited

OTHER PUBLICATIONS

Wei et al. Regulation of adipose-derived adult stem cells differentiating into chondrocytes with the use of rhBMP-2. Cytotherapy (2006) vol. 8, No. 6, 570 579 (Year: 2006).*
Lee et al. Adipose stem cells can secrete angiogenic factors that inhibit hyaline cartilage regeneration. Stem Cell Research & Therapy 2012, 3:35 (Year: 2012).*
Luo et al. Inactivation of Wnt/b-catenin signaling in human adipose-derived stem cells is necessary for chondrogenic differentiation and maintenance. Biomedicine & Pharmacotherapy 67 (2013) 819-824 (Year: 2013).*
Peran et al. Activin/BMP2 chimeric ligands direct adipose-derived stem cells to chondrogenic differentiation. Stem Cell Research (2013) 10, 464-476 (Year: 2013).*
Saito et al. VEGF-A induces its negative regulator, soluble form of VEGFR-1, by modulating its alternative splicing. FEBS Letters 587 (2013) 2179-2185 (Year: 2013).*
Ranieri et al. Vascular Endothelial Growth Factor (VEGF) as a Target of Bevacizumab in Cancer: From the Biology to the Clinic. Current Medicinal Chemistry, 2006, 13, 1845-1857 (Year: 2006).*
Grottkau et al. Osteogenesis of Adipose-Derived Stem Cells. Bone Research (2013) 2: 133-145. (Year: 2013).*
Levi et al., "In Vivo Directed Differentiation of Pluripotent Stem Cells for Skeletal Regeneration", PNAS, Dec. 11, 2012, pp. 20379-20384, vol. 109, No. 50, PNAS, Washington, DC.
University of Southampton, "Ground Breaking Hip and Stem Cell Surgery Completed Using 3D-Printed Implant", May 16, 2014, pp. 1-7. [online] [retrieved on Mar. 7, 2016]. Retrieved from the internet: https://www.sciencedaily.com/releases/2014/05/140516203334.htm.
Chan et al., "Clonal Precursor of Bone, Cartilage, and Hematopoietic Niche Stromal Cells", PNAS, Jul. 30, 2013, pp. 12643-12648, vol. 110, No. 31, PNAS, Washington, DC.
Knippenberg et al., "Osteogenesis Versus Chondrogenesis by BMP-2 and BMP-7 in Adipose Stem Cells", Biochemical and Biophysical Research Communications. 2006, pp. 902-908, vol. 342, Elsevier, Amsterdam, Netherlands.
Mcardle et al., "Positive Selection for Bone Morphogenetic Protein Receptor Type-IB Promotes Differentiation and Specification of Human Adipose Derived Stromal Cells Toward an Osteogenic Lineage", Tissue Engineering: Part A, 2014, pp. 3031-3040, vol. 20, Nos. 21 and 22, Mary Ann Liebert, Inc., New Rochelle, NY.
Ruetze et al., "Adipose-Derived Stromal Cells for Osteoarticular Repair: Trophic Function Versus Stem Cell Activity", Expert Reviews in Molecular Medicine, May 2014, pp. 1-19, vol. 16, e9, Cambridge University Press, Cambridge, United Kingdom.
Levi et al. "Human Adipose Derived Stromal Cells Heal Critical Size Mouse Calvarial Defects", PLos One, Jun. 17, 2010, pp. 1-11, vol. 5, No. 6, e11177, PLos One, San Francisco, CA.
Kuznetsov et al., "Circulating Skeletal Stem Cells", The Journal of Cell Biology, May 28, 2001, pp. 1133-1139 vol. 153, No. 5, Rockefeller University Press, New York, NY.
Bianco et al., "Stem Cells in Tissue Engineering", Nature, Nov. 1, 2001, pp. 118-121, vol. 414, Macmillan Publishers, London, United Kingdom.
Dawson et al., "Concise Review: Bridging the Gap: Bone Regeneration Using Skeletal Stem Cell-Based Strategies—Where Are We Now?", Stem Cells, 2014, pp. 35-44, vol. 32, AlphaMed Press, Durham, NC.
Tevlin et al. "Osteoclast derivation from mouse bone marrow", J. Vis. Exp., Nov. 5, 2014, pp. 1-6, (93), a52056,JoVE, Cambridge, MA.
Chan et al., "Endochondral ossification is required for hematopoietic stem cell niche formation", Nature, Jan. 22, 2009, pp. 490-449. ;457(7228), Nature Publishing Group, London, United Kingdom.
Bonewald et al., "Osteocytes, mechanosensing and Wnt signaling", Bone, Apr. 2008, pp. 606-615, vol. 42, Issue 4, Elsevier, New York City, NY.
Dragoo et al., "Bone induction by BMP-2 transduced stem cells derived from human fat", Journal of Orthopaedic Research, Jul. 2003, pp. 622-629, vol. 21, Issue 4, Elsevier, New York City, NY.
Khan et al., "Strategies for cell manipulation and skeletal tissue engineering using high-throughput polymer blend formulation and microarray techniques", Biomaterials, Mar. 2010, pp. 2216-2228, vol. 31, Issue 8, Elsevier, New York City, NY.
Rochefort et al., "Osteocyte: the unrecognized side of bone tissue", Osteoporosis International, Sep. 2010, pp. 1457-1469, vol. 21, Issue 9, Springer, Berlin, Germany.
Quatro et al. (2010) "Opposite Spectrum of Activity of Canonical Wnt Signaling in the Osteogenic Context of Undifferentiated and Differentiated Mesenchymal Cells: Implications for Tissue Engineering" Tissue Engineering, vol. 16, No. 10, pp. 3185-3197.
Olivares-Navarrete (2011) "Mediation of Osteogenic Differentiation of Human Mesenchymal Stem Cells on Titanium Surfaces by a Wnt-Integrin Feedback Loop" Biomaterials, vol. 32, pp. 6399-6411.
Gerber et al. (1999) "VEGF couples hypertrophic cartilage remodeling, ossification and angiogenesis during endochondral bone formation" Nature Medicine, vol. 5, No. 6, pp. 623-628.
Koga et al. (2008) "Comparison of mesenchymal tissues-derived stem cells for in vivo chondrogenesis: suitable conditions for cell therapy of cartilage defects in rabbit" Cell Tissue Res, 333:207-215.

\* cited by examiner

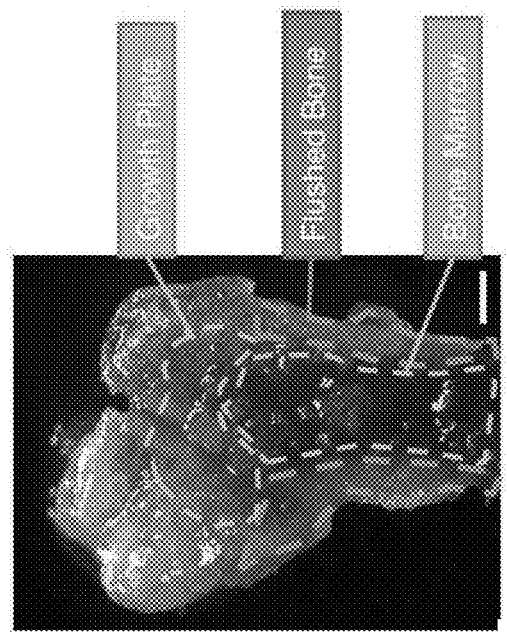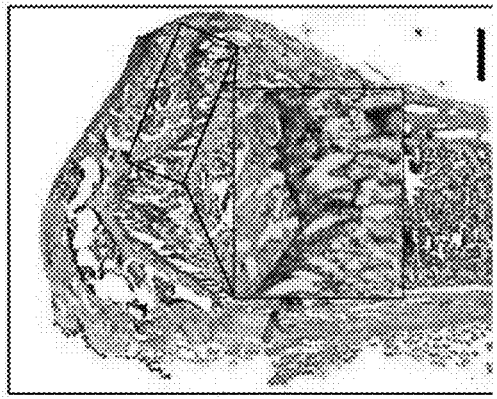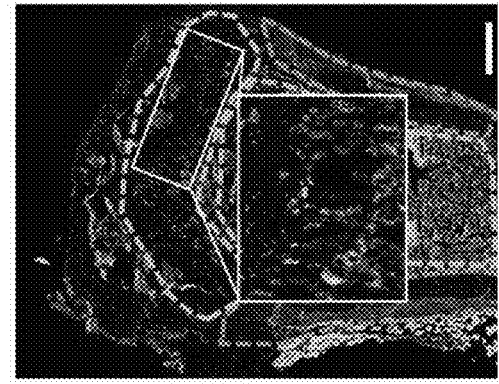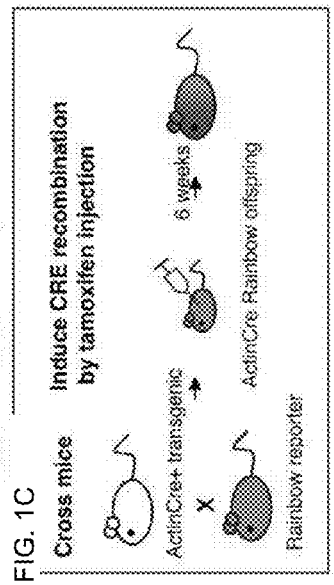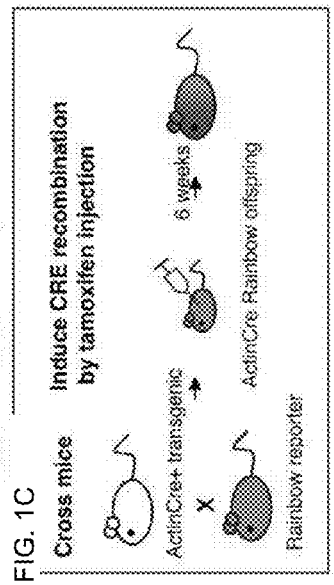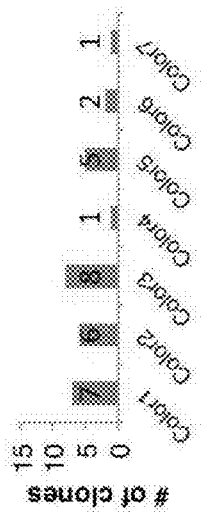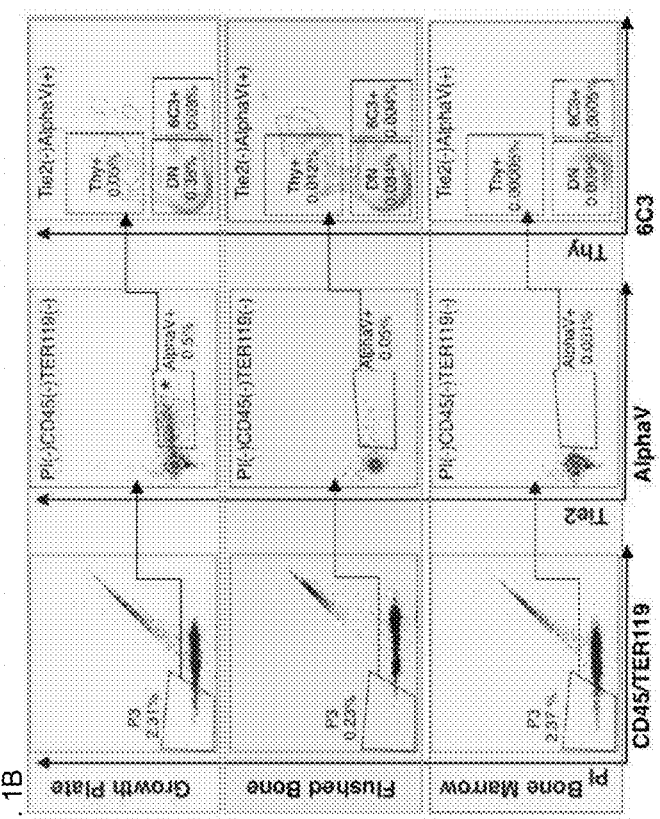

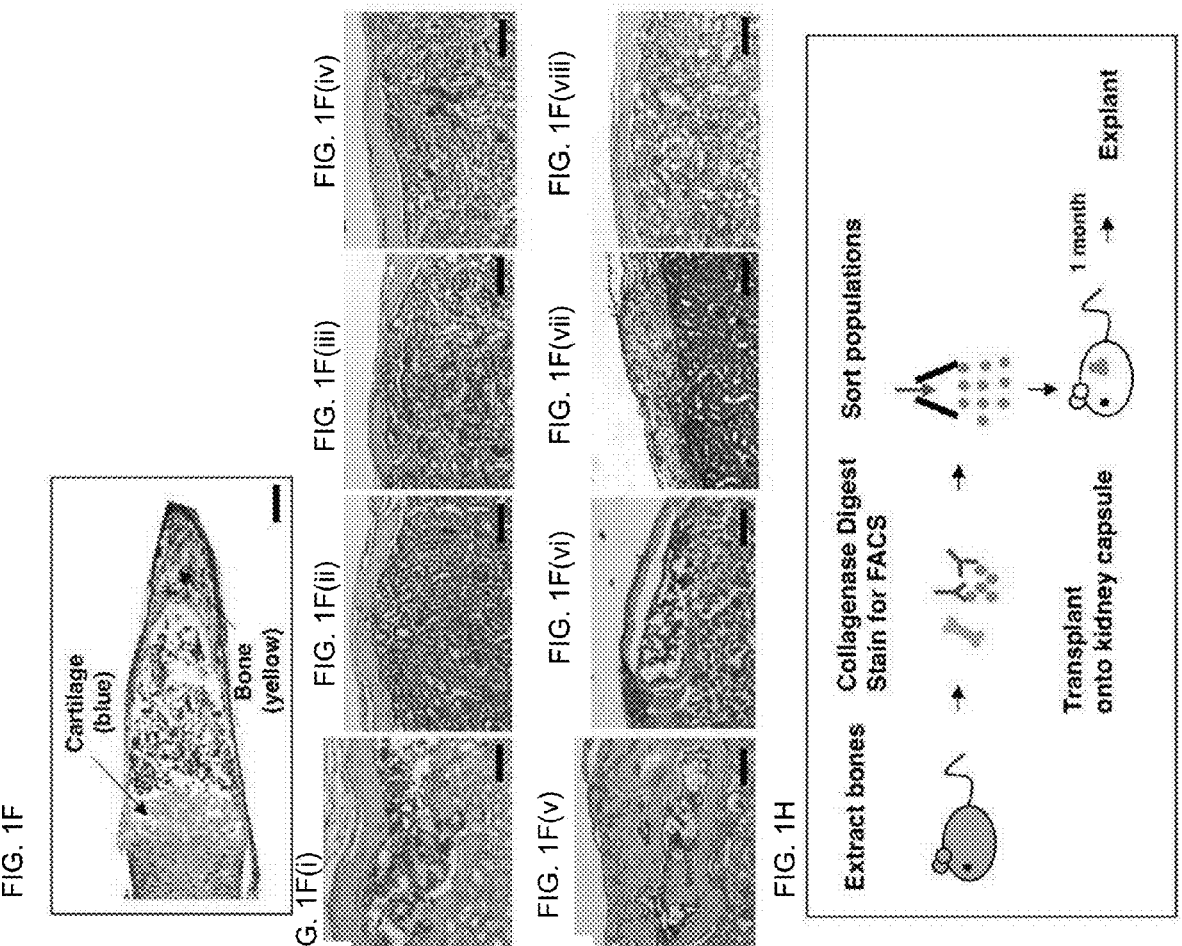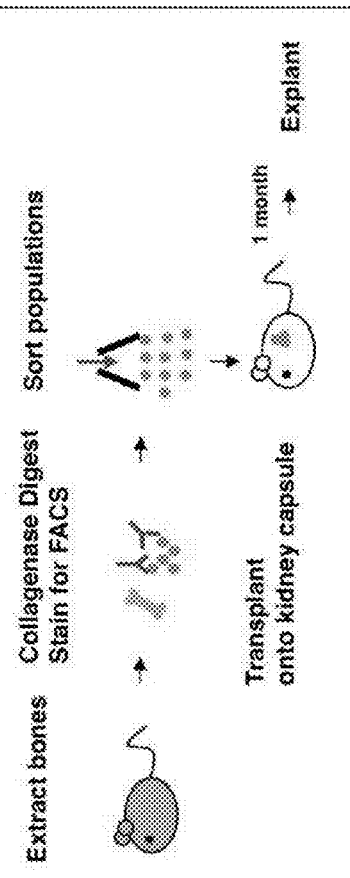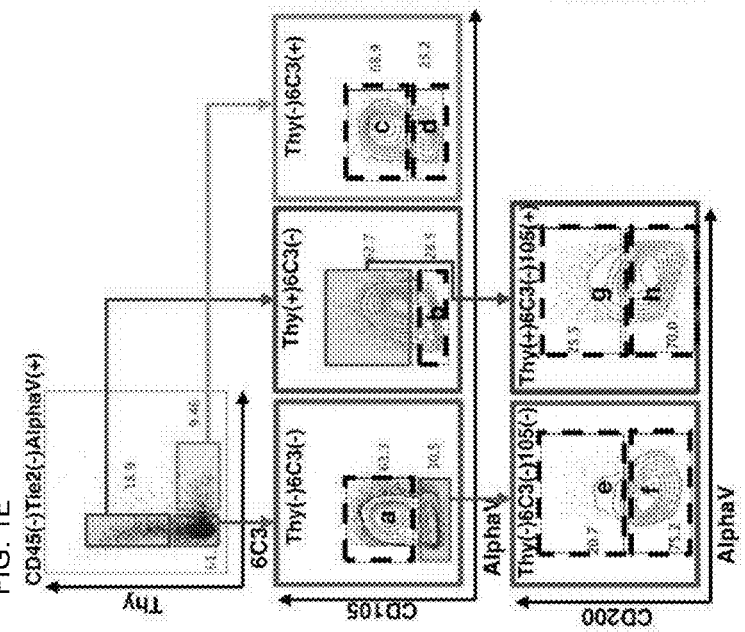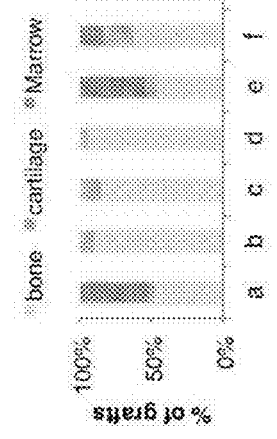

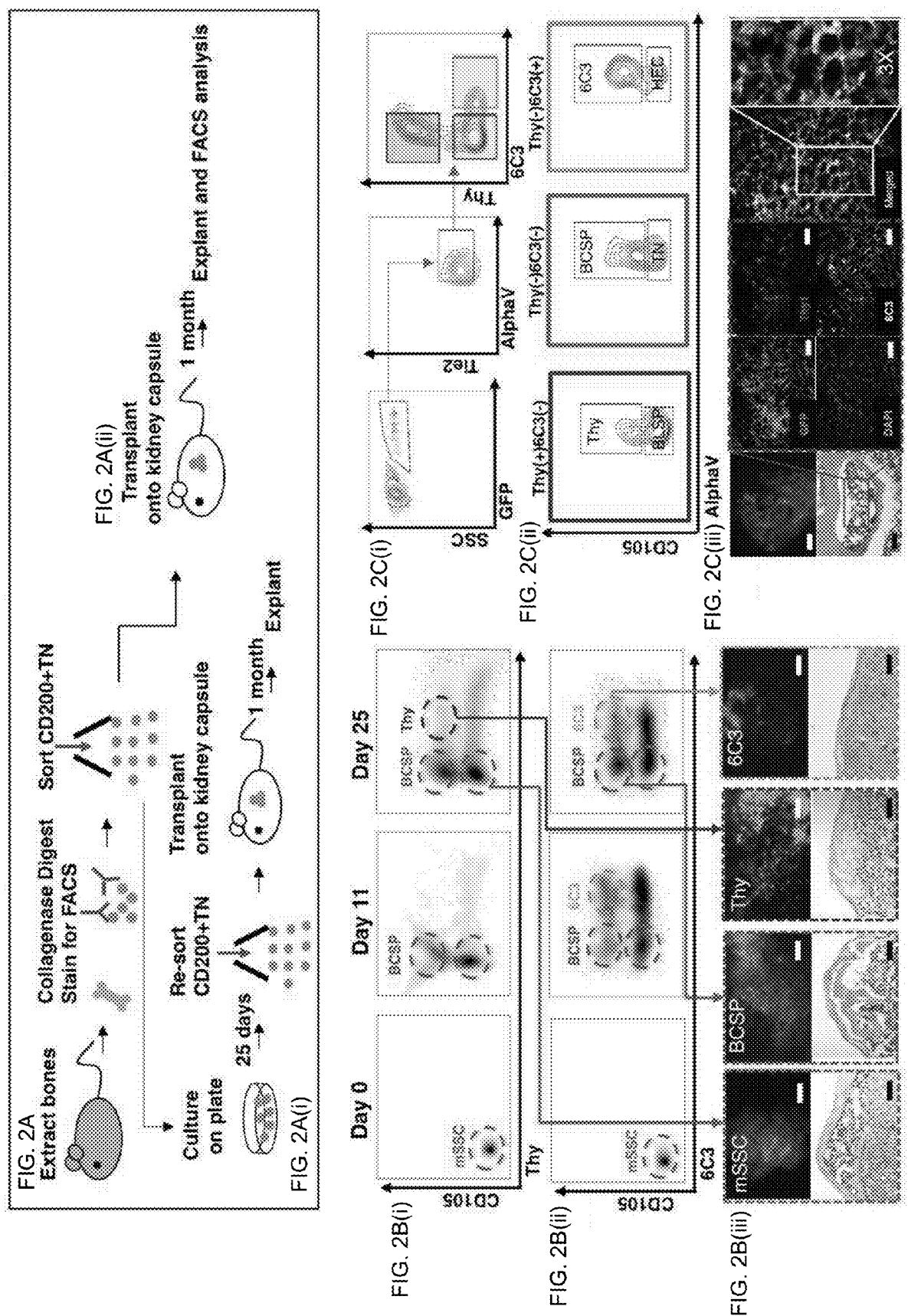

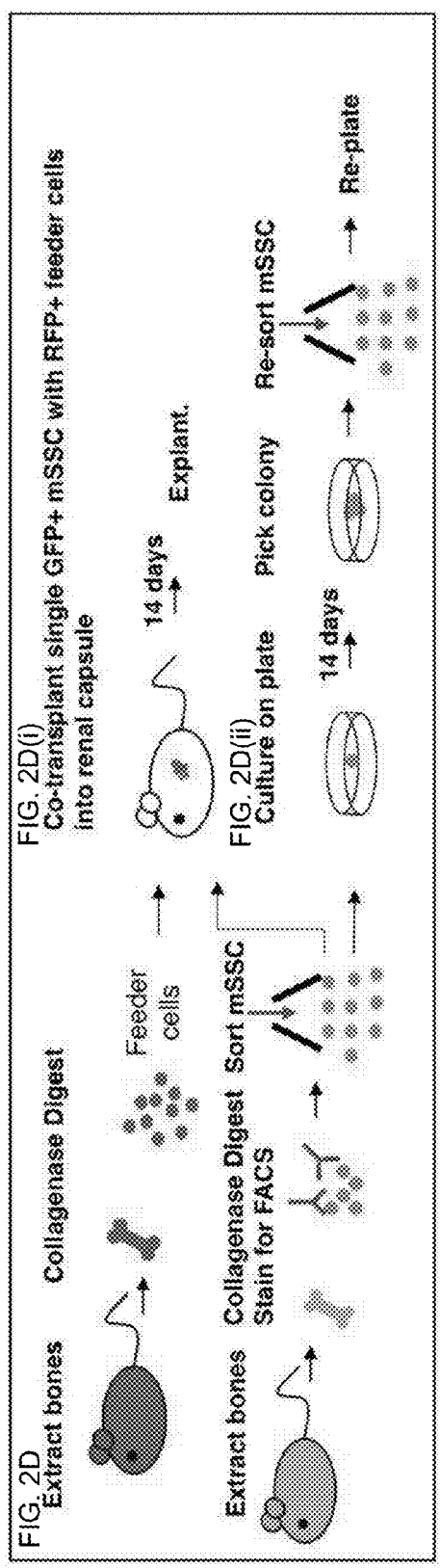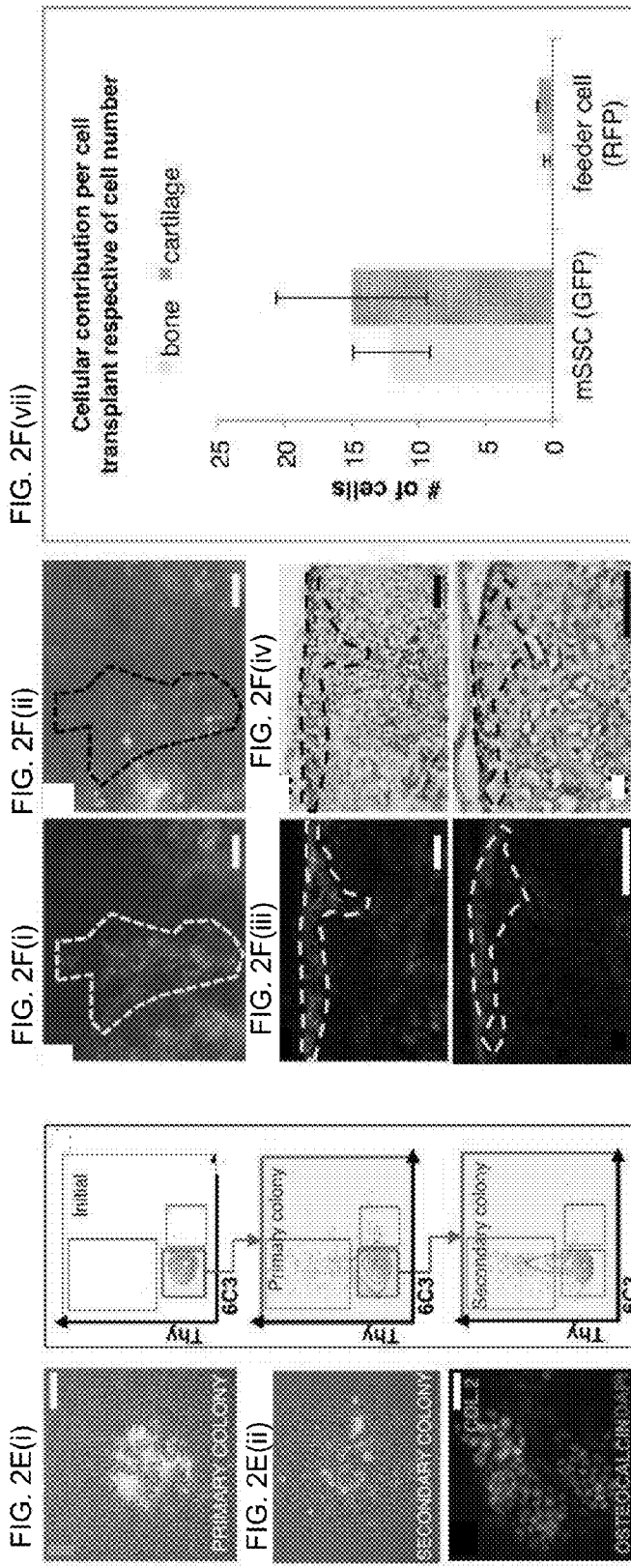

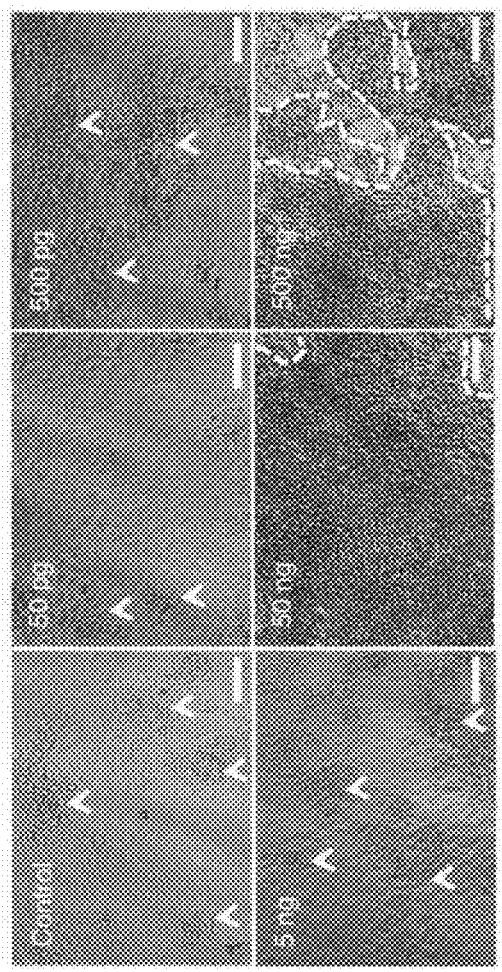
FIG. 3H
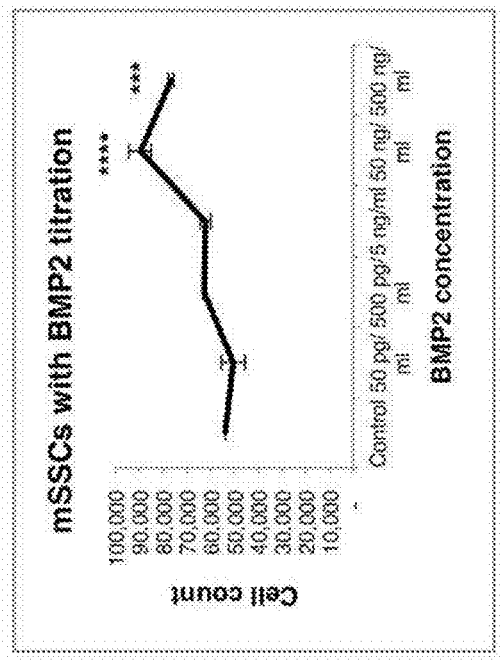
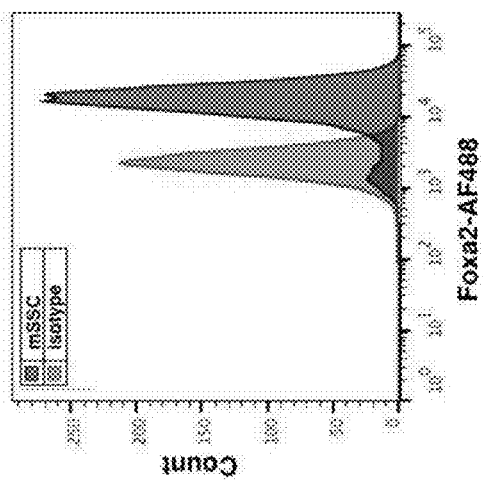
FIG. 3K
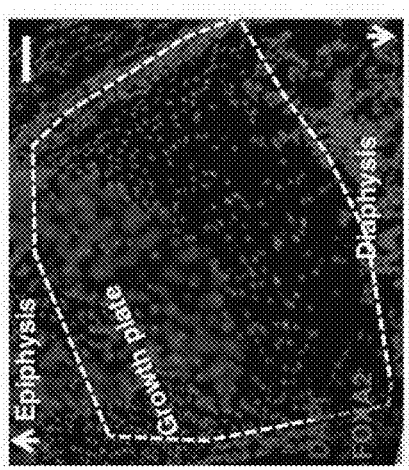
FIG. 3J
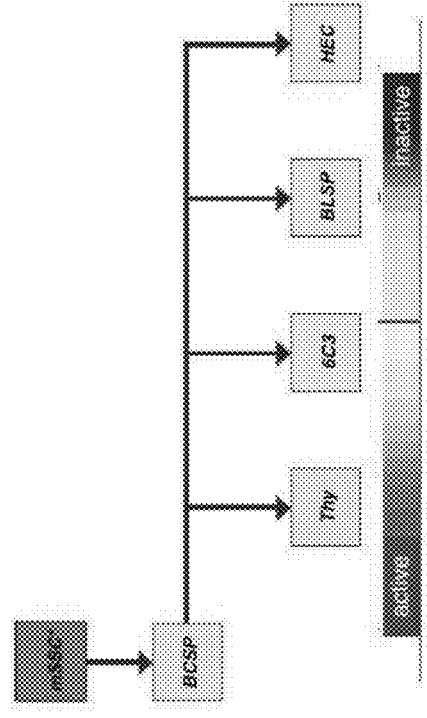
FIG. 3I  *Foxa2*

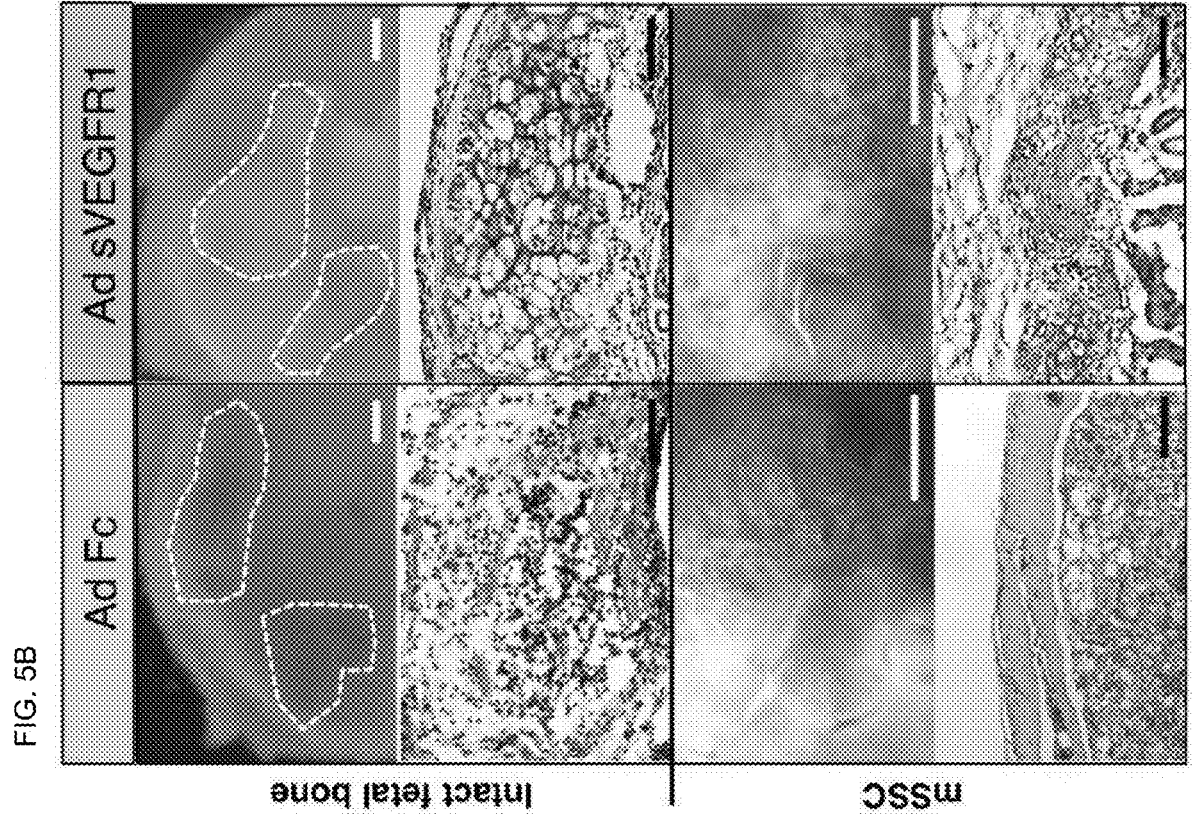
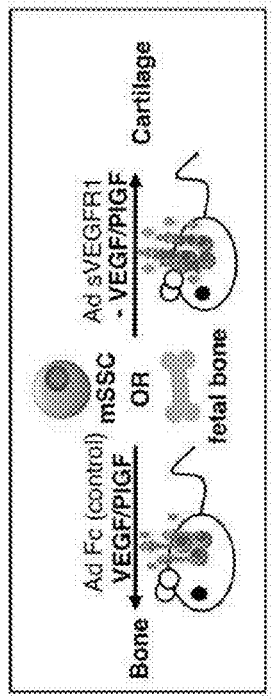
FIG. 5A
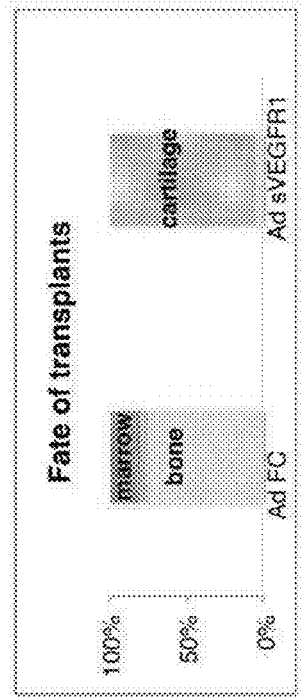
FIG. 5C
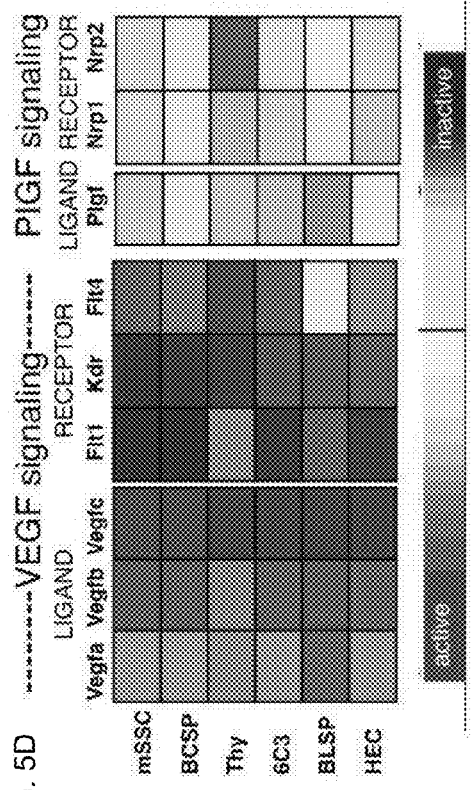
FIG. 5D
FIG. 5B

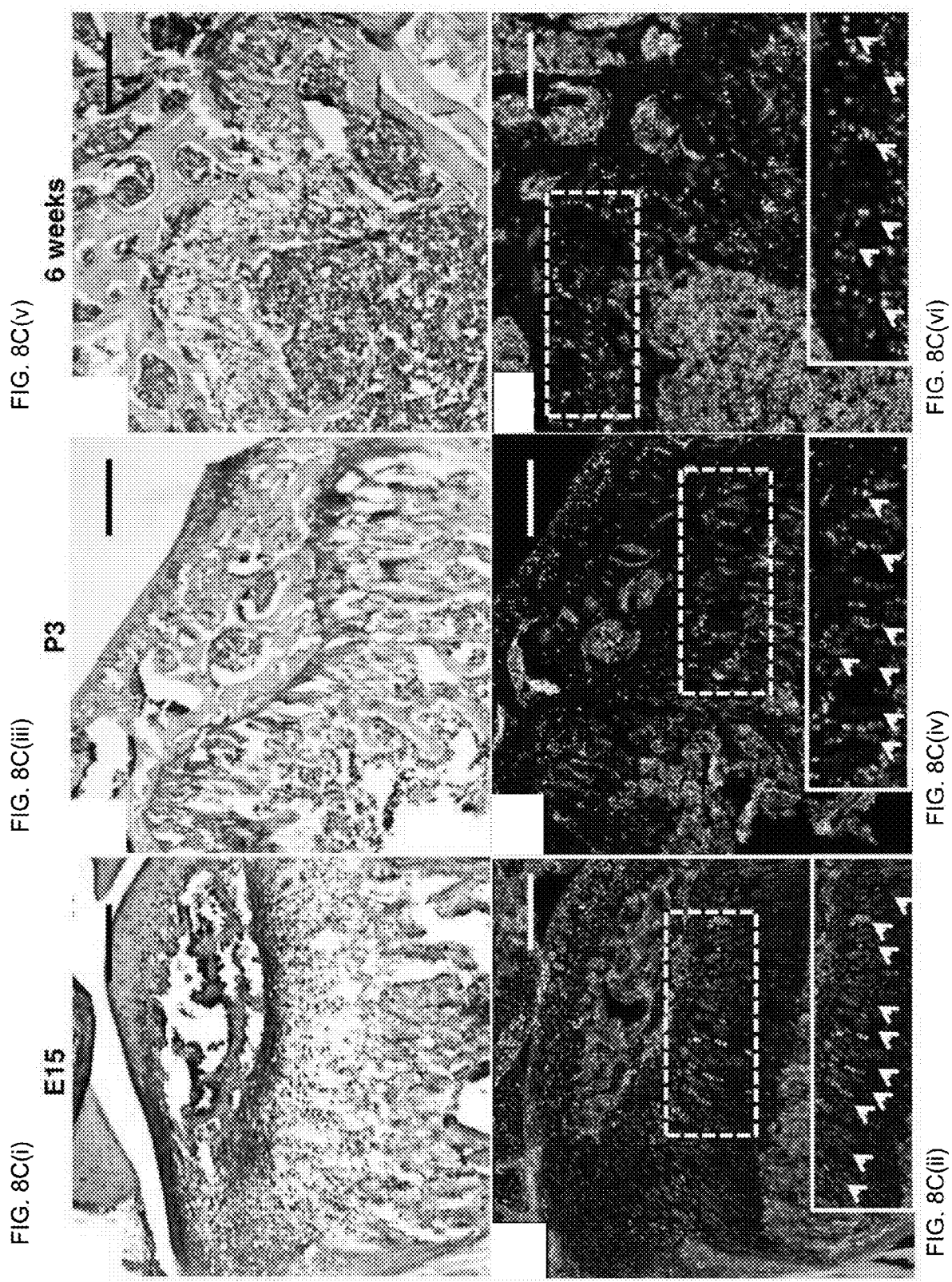

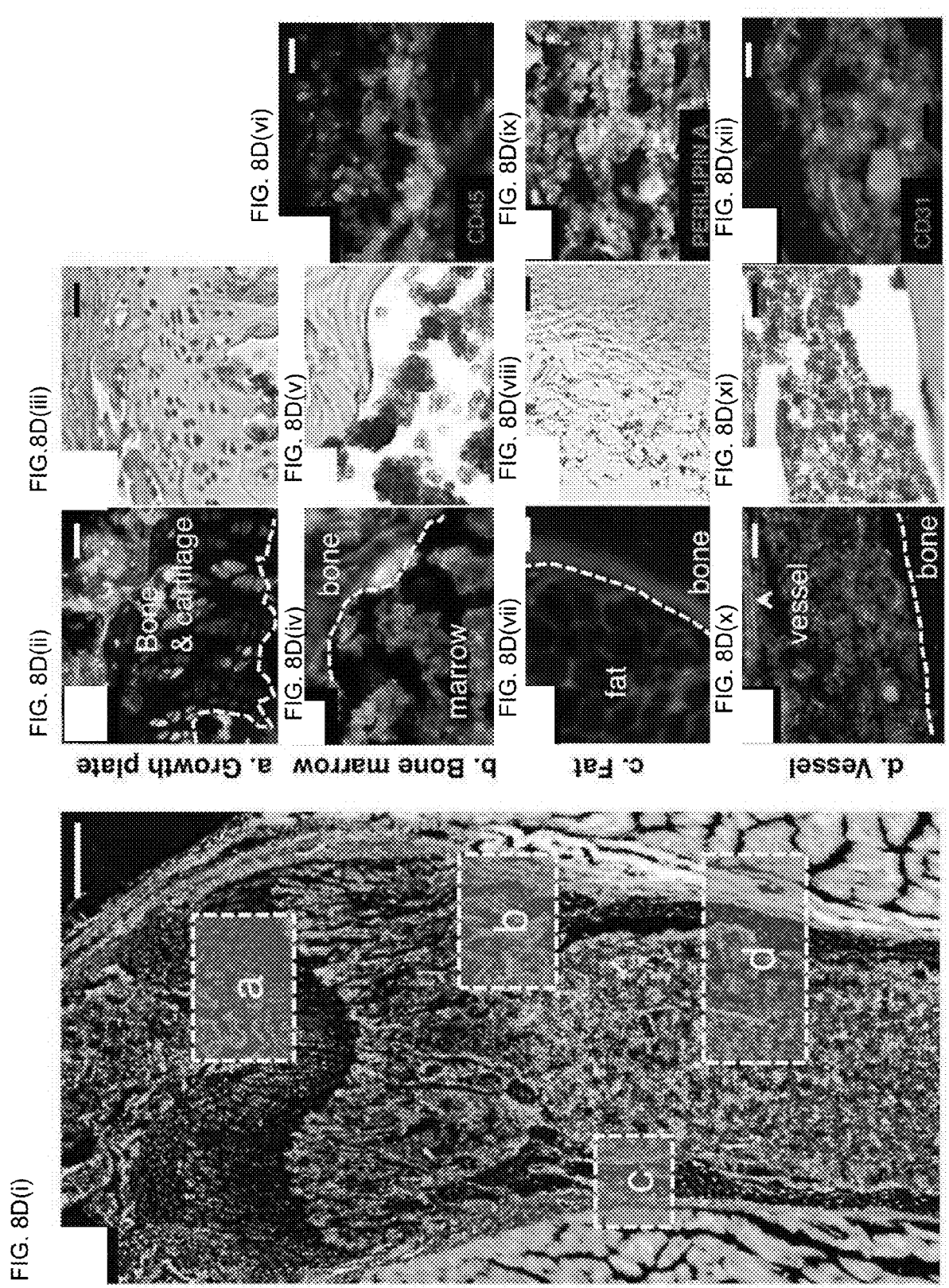

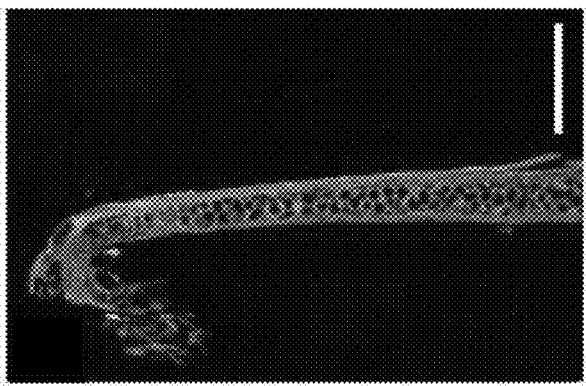
FIG. 8E(iii)
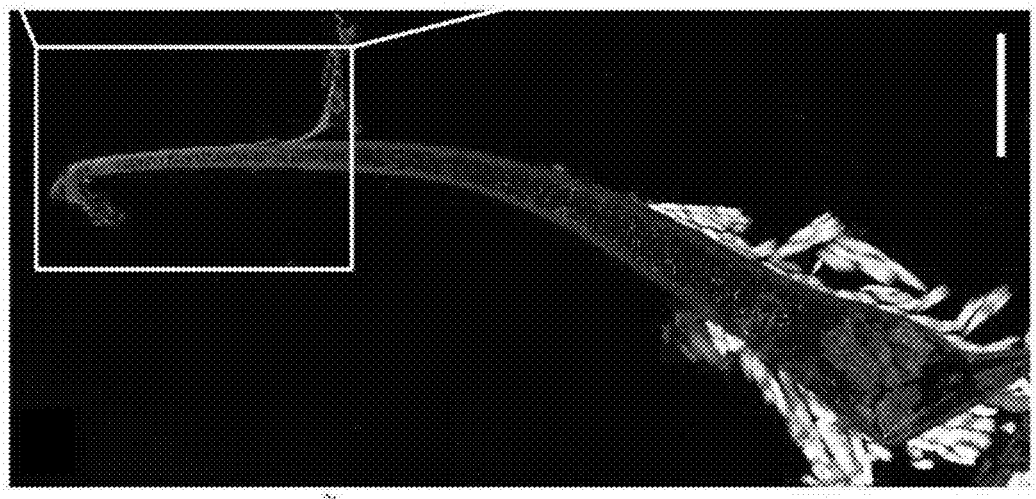
FIG. 8E(ii)
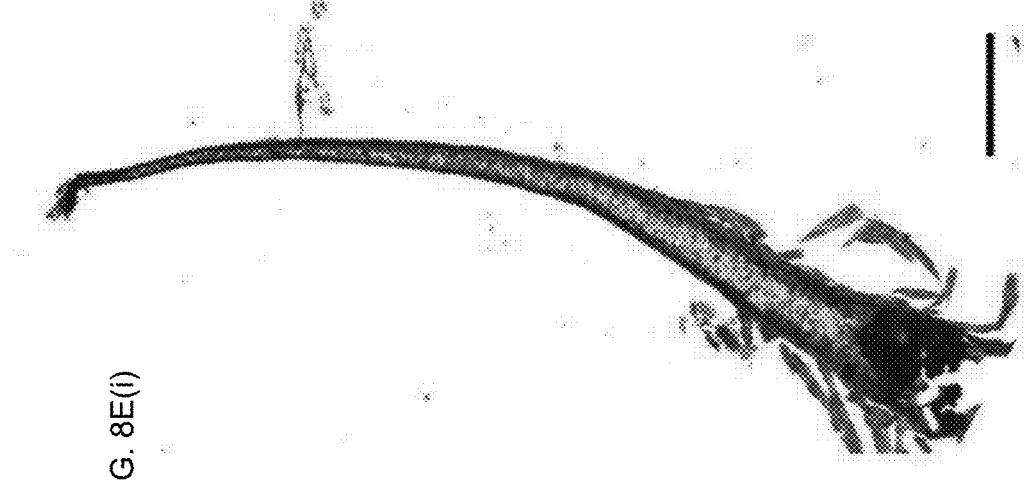
FIG. 8E(i)

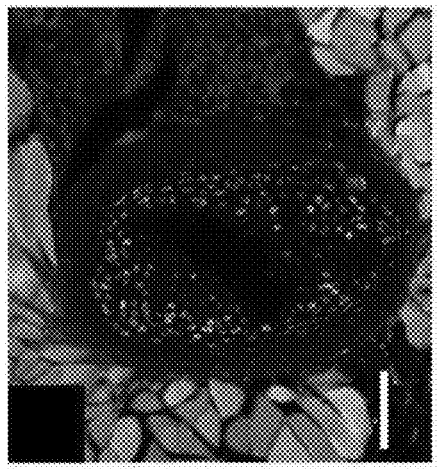
FIG. 8F(iii)
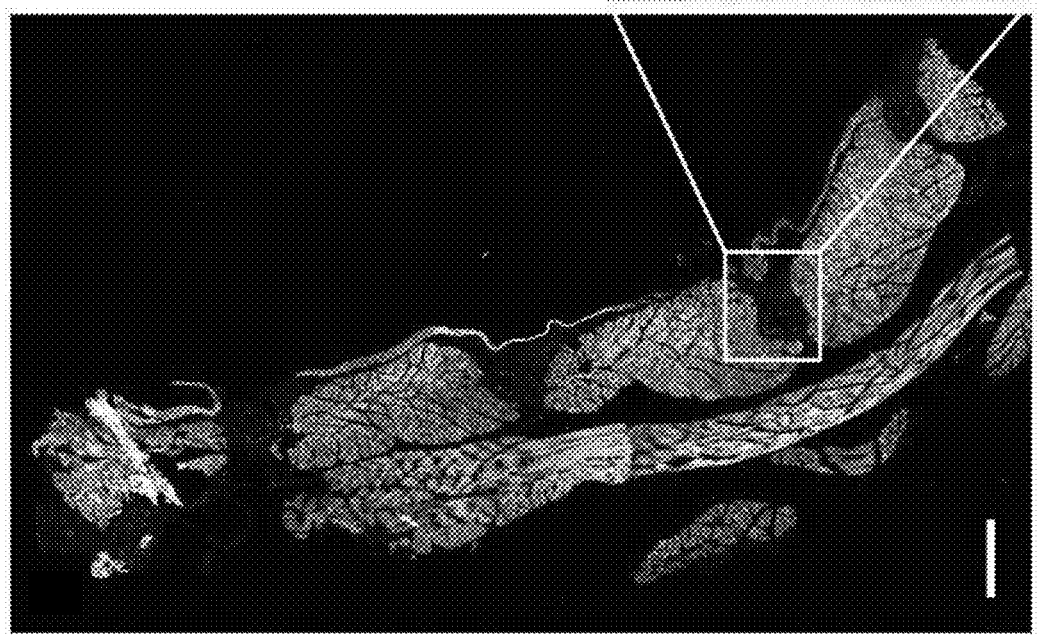
FIG. 8F(ii)
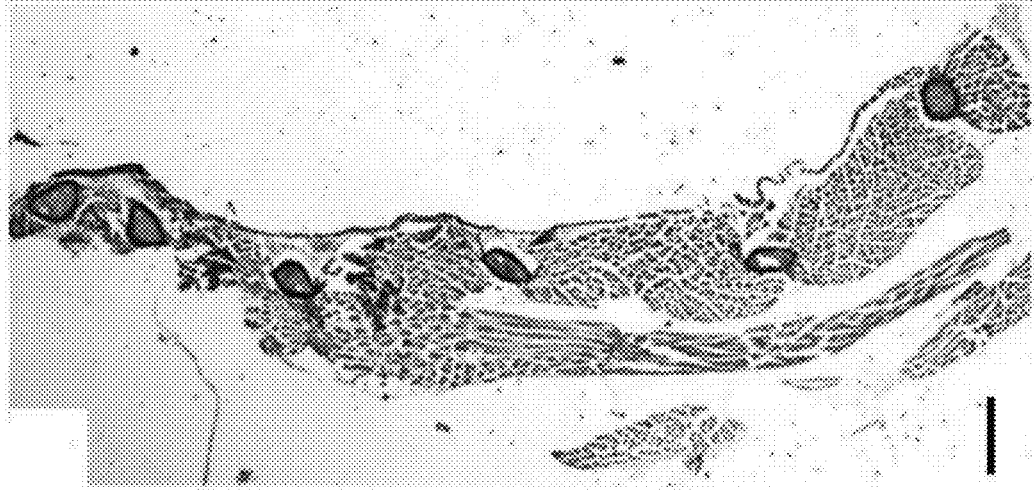
FIG. 8F(i)

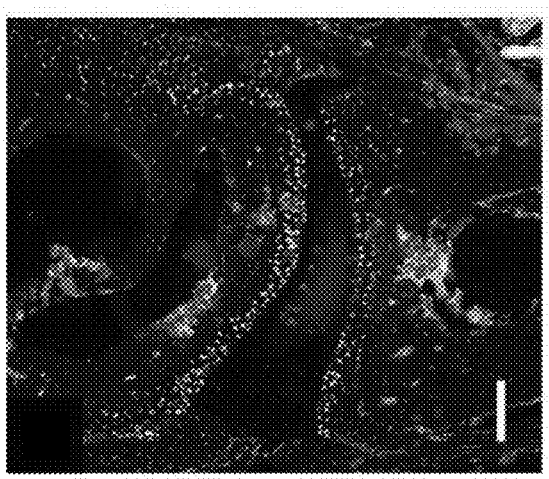
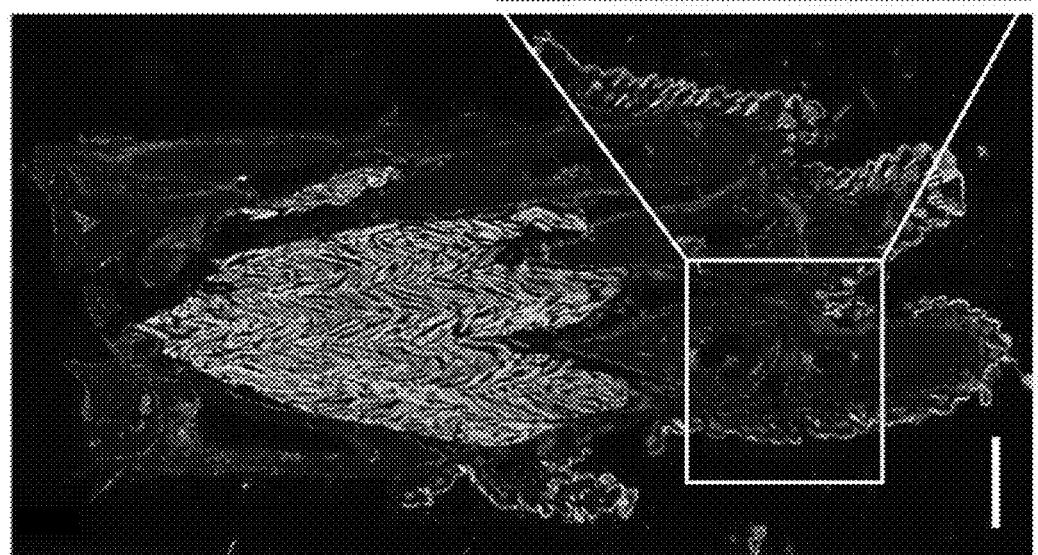
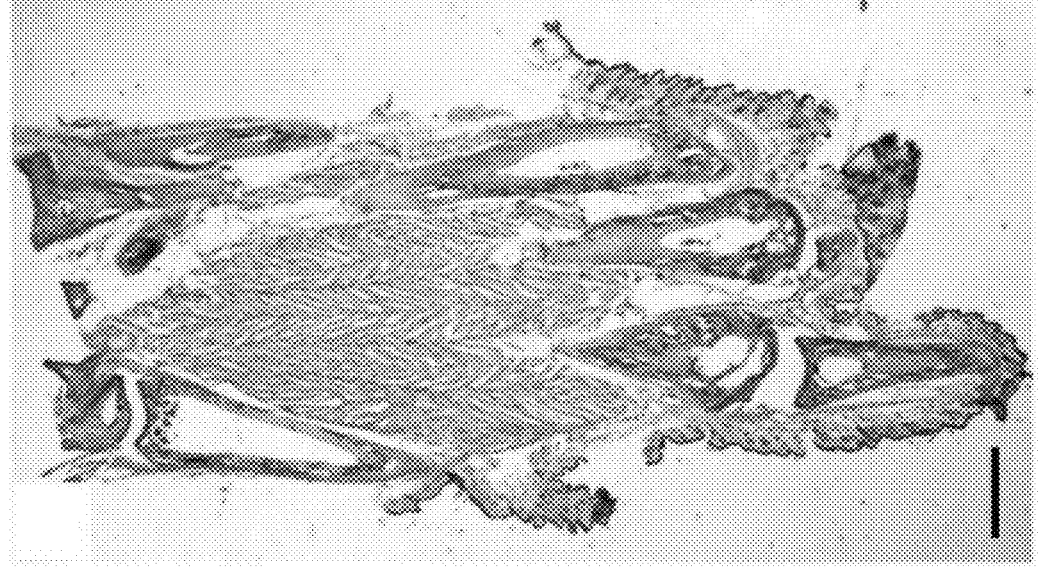

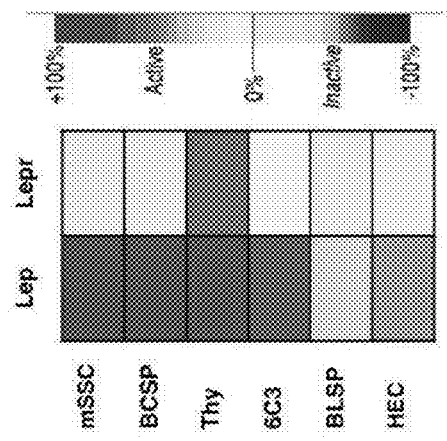
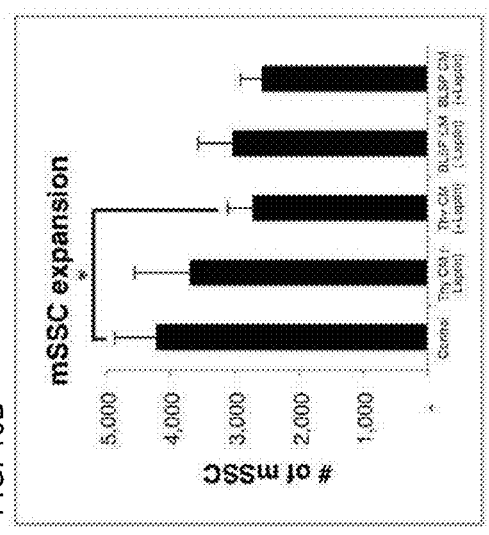
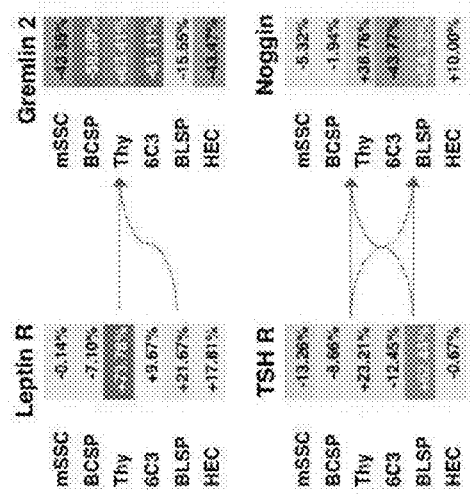
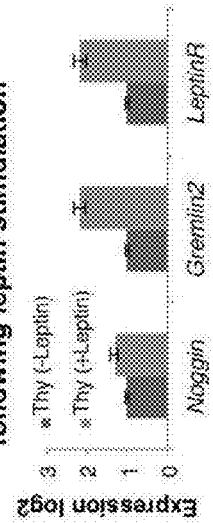
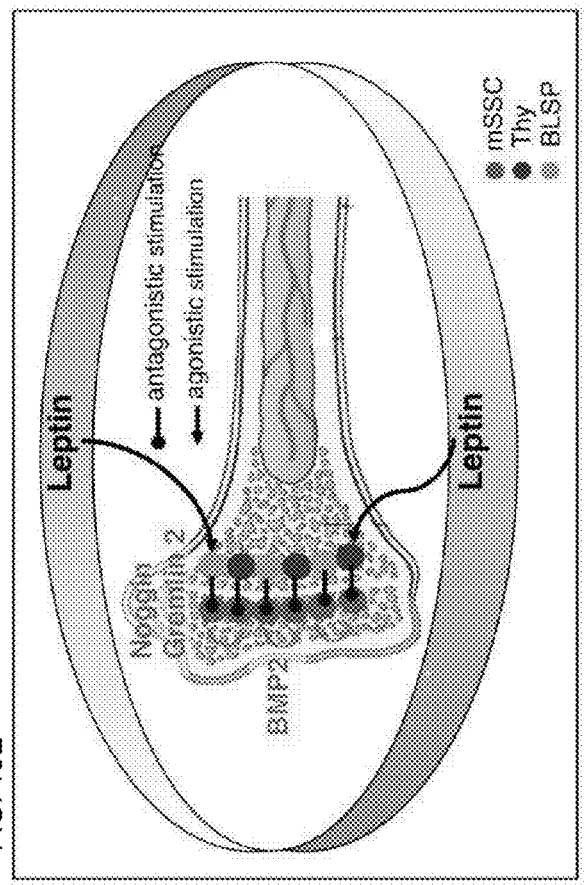

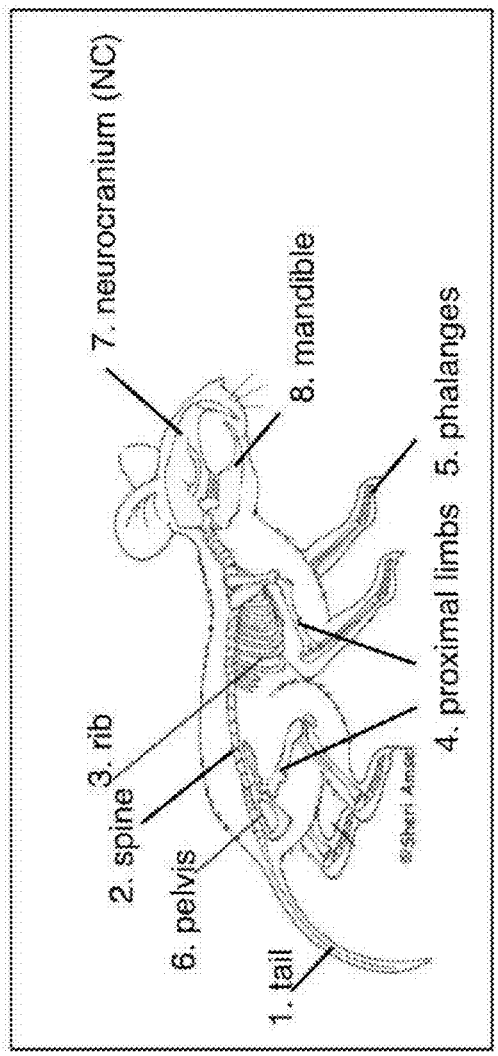
FIG. 14A
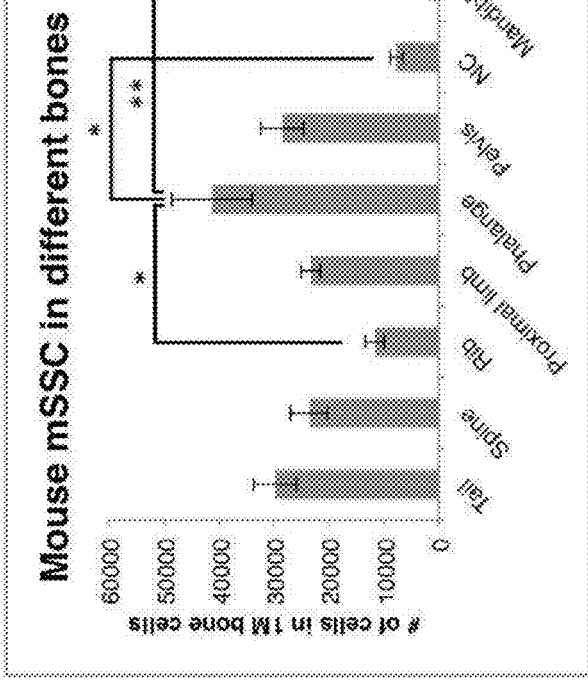
FIG. 14B
FIG. 14C
| Skeletal parts | CFU (in 500) | STDEV (n=8) |
|---|---|---|
| Tail | 10 | ± 1.4 |
| Spine | 25 | ± 1.7 |
| Rib | 19 | ± 2.5 |
| Proximal limbs | 22 | ± 1.7 |
| Phalanges | 26 | ± 3.2 |
| Pelvis | 20 | ± 1.5 |
| NC | 11 | ± 1.5 |
| Mandible | 1 | ± 0.3 |

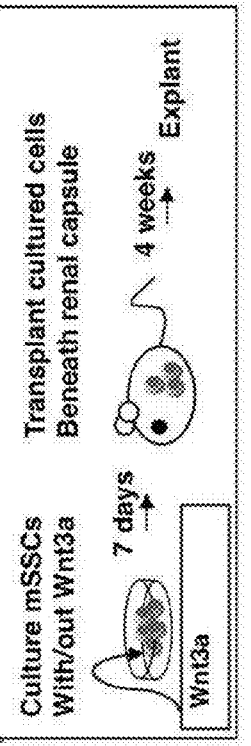
FIG. 15B(i)
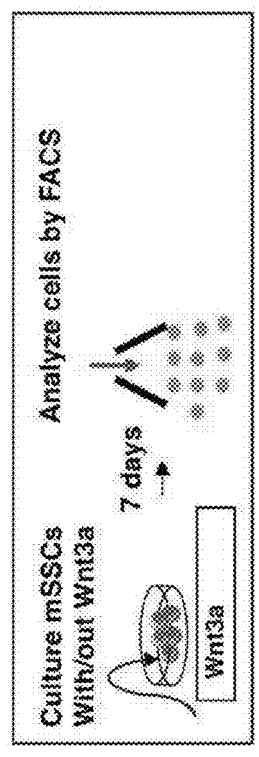
FIG. 15B(ii)
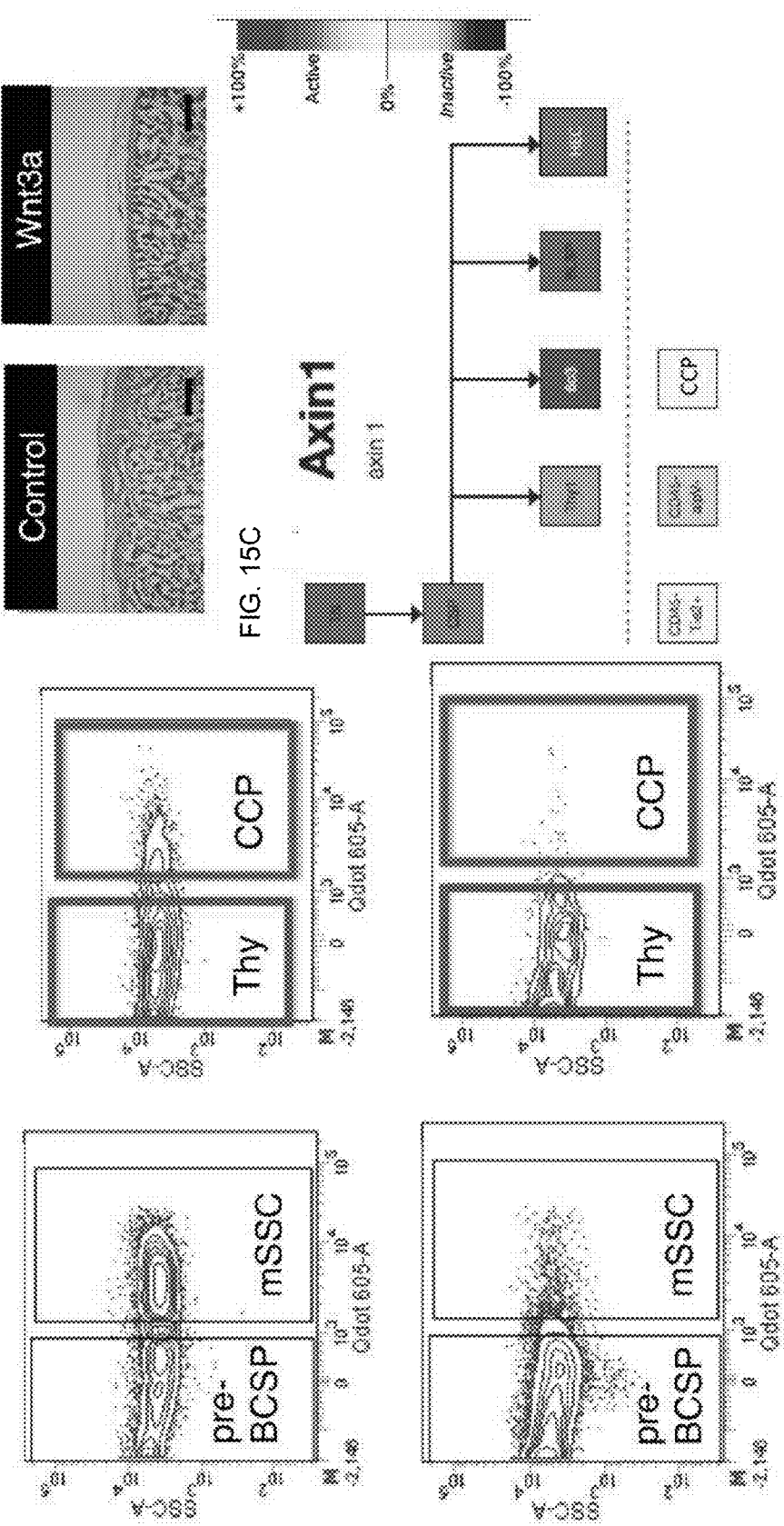
FIG. 15C

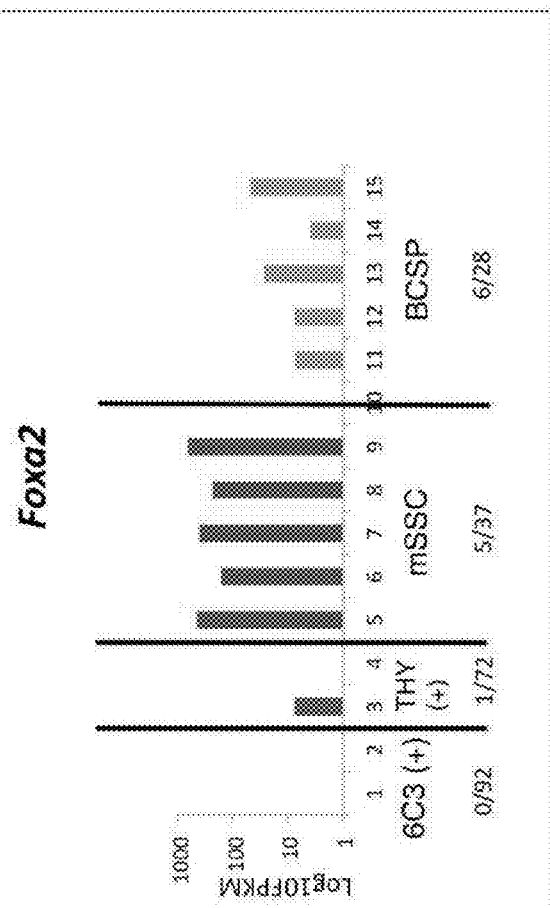
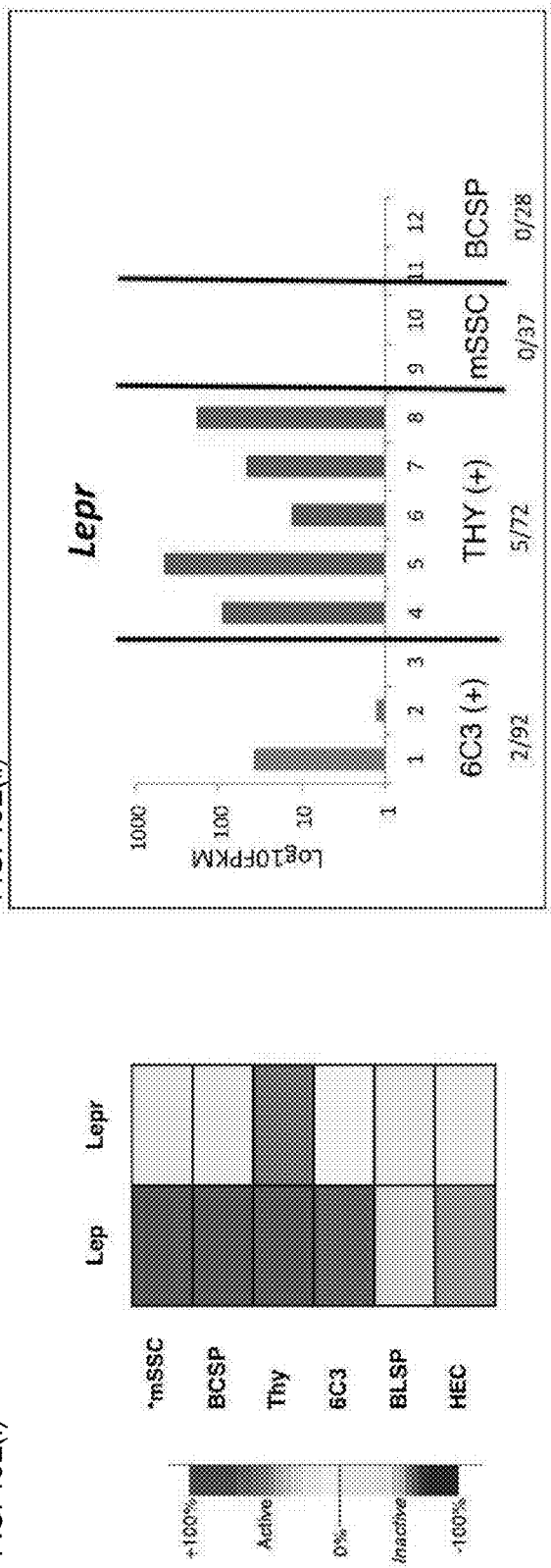
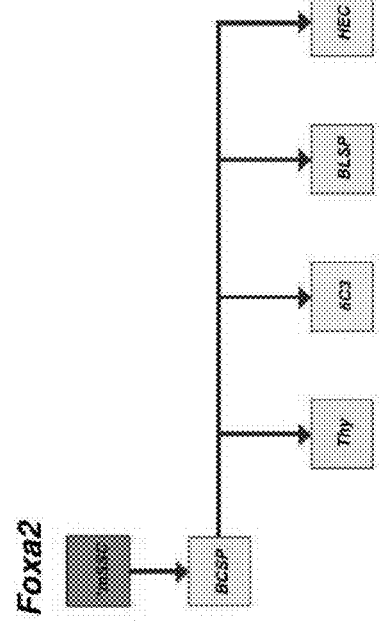
FIG. 15E(ii)
FIG. 15E(i)
FIG. 15F(ii)
FIG. 15F(i)

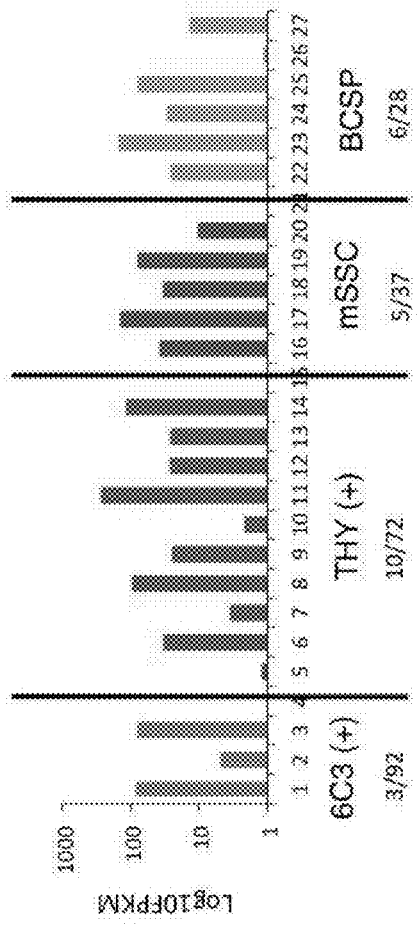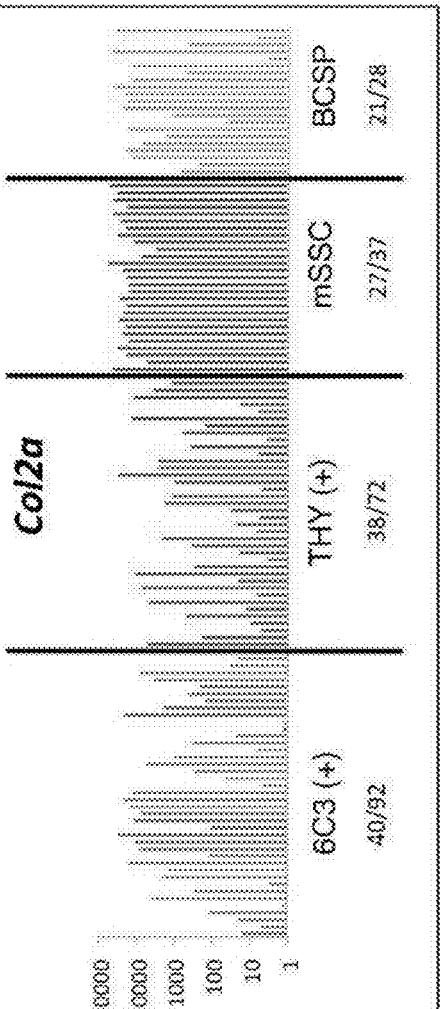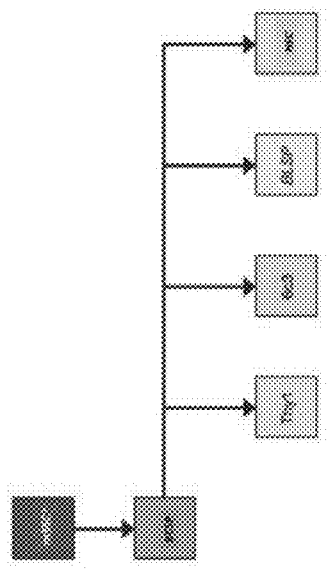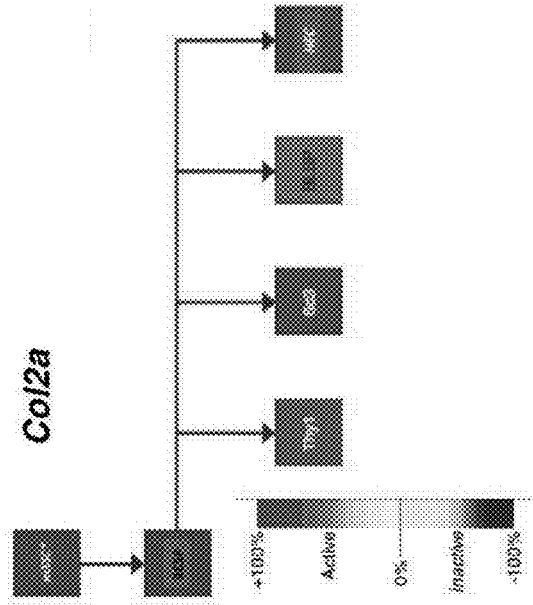
FIG. 15G(i)
FIG. 15G(ii)
FIG. 15H(i)
FIG. 15H(ii)

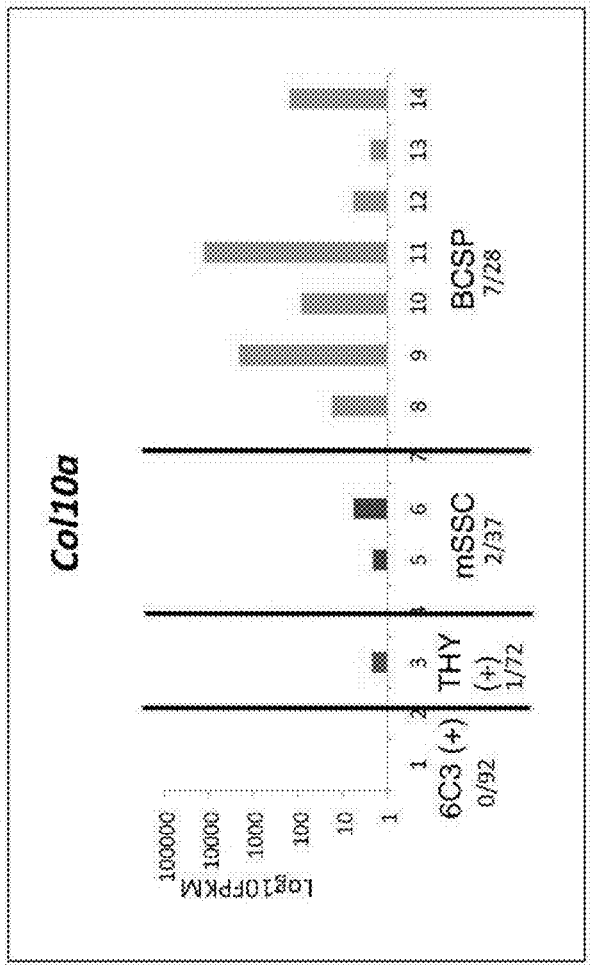
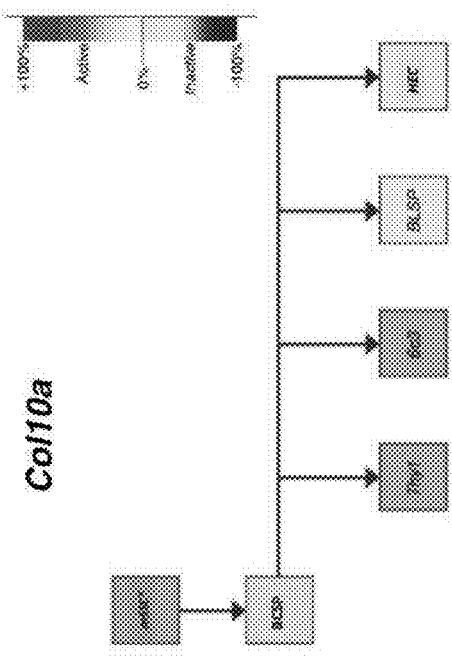
FIG. 15I(i)
FIG. 15I(ii)
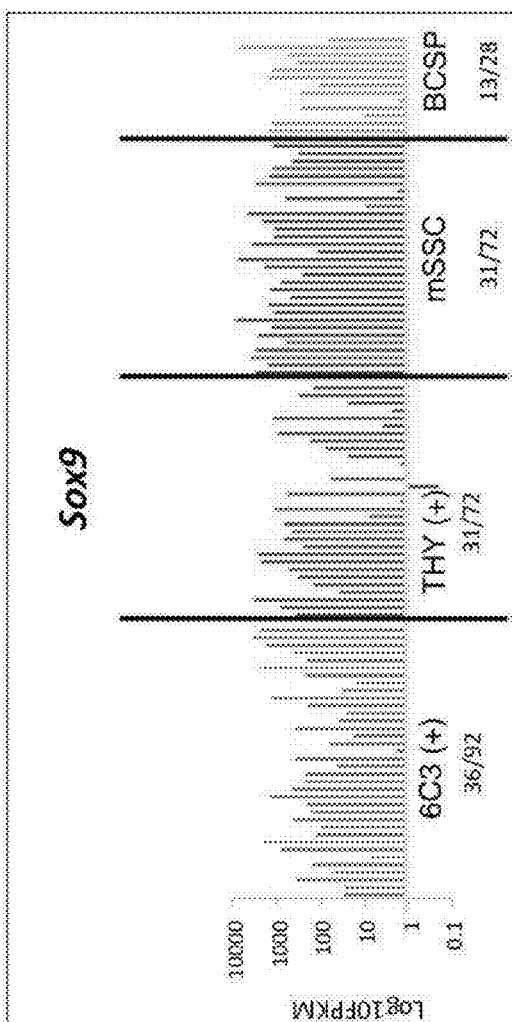
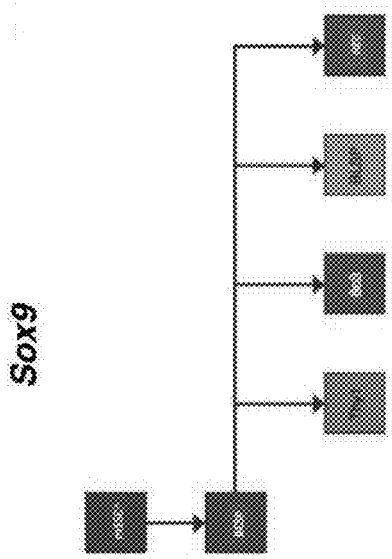
FIG. 15J(i)
FIG. 15J(ii)

FIG. 17A
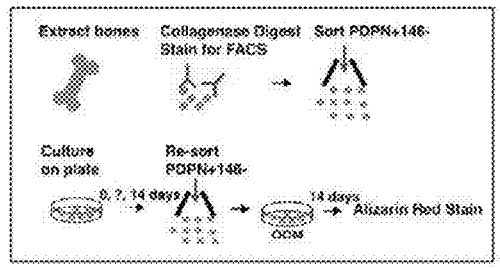
FIG. 17C  FIG. 17D
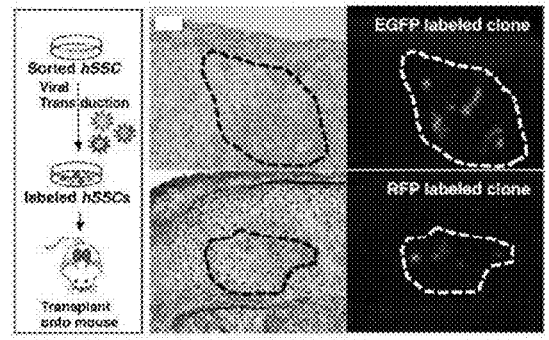
FIG. 17B
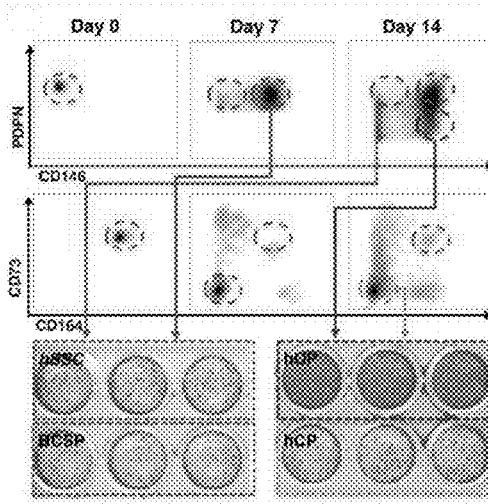
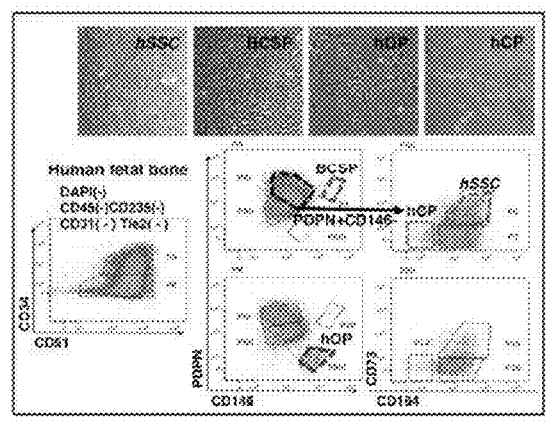
FIG. 17E FIG. 19A
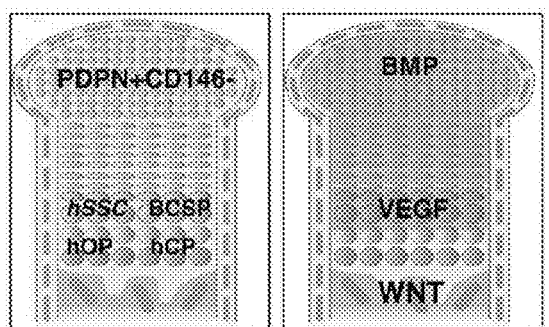
FIG. 19B
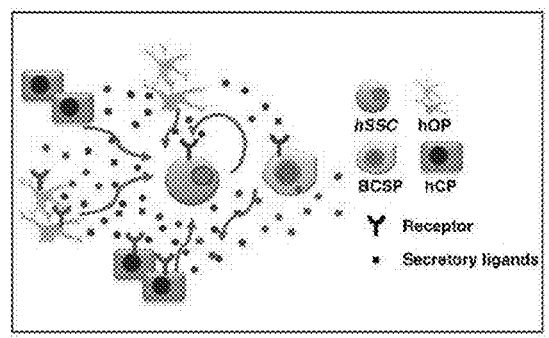
FIG. 19C
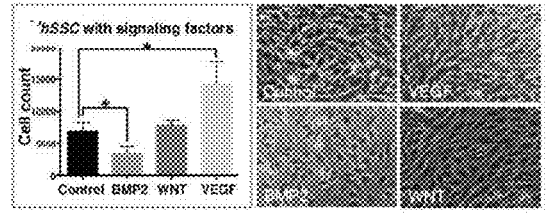
FIG. 19E
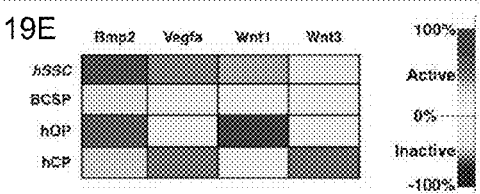
FIG. 19D
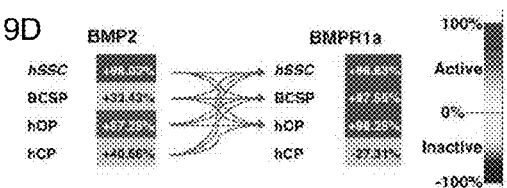
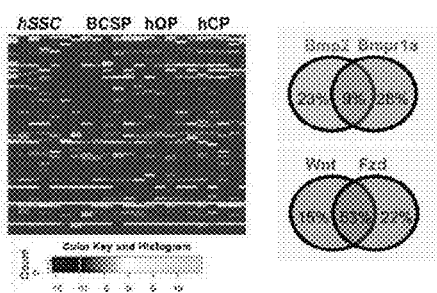
FIG. 19F

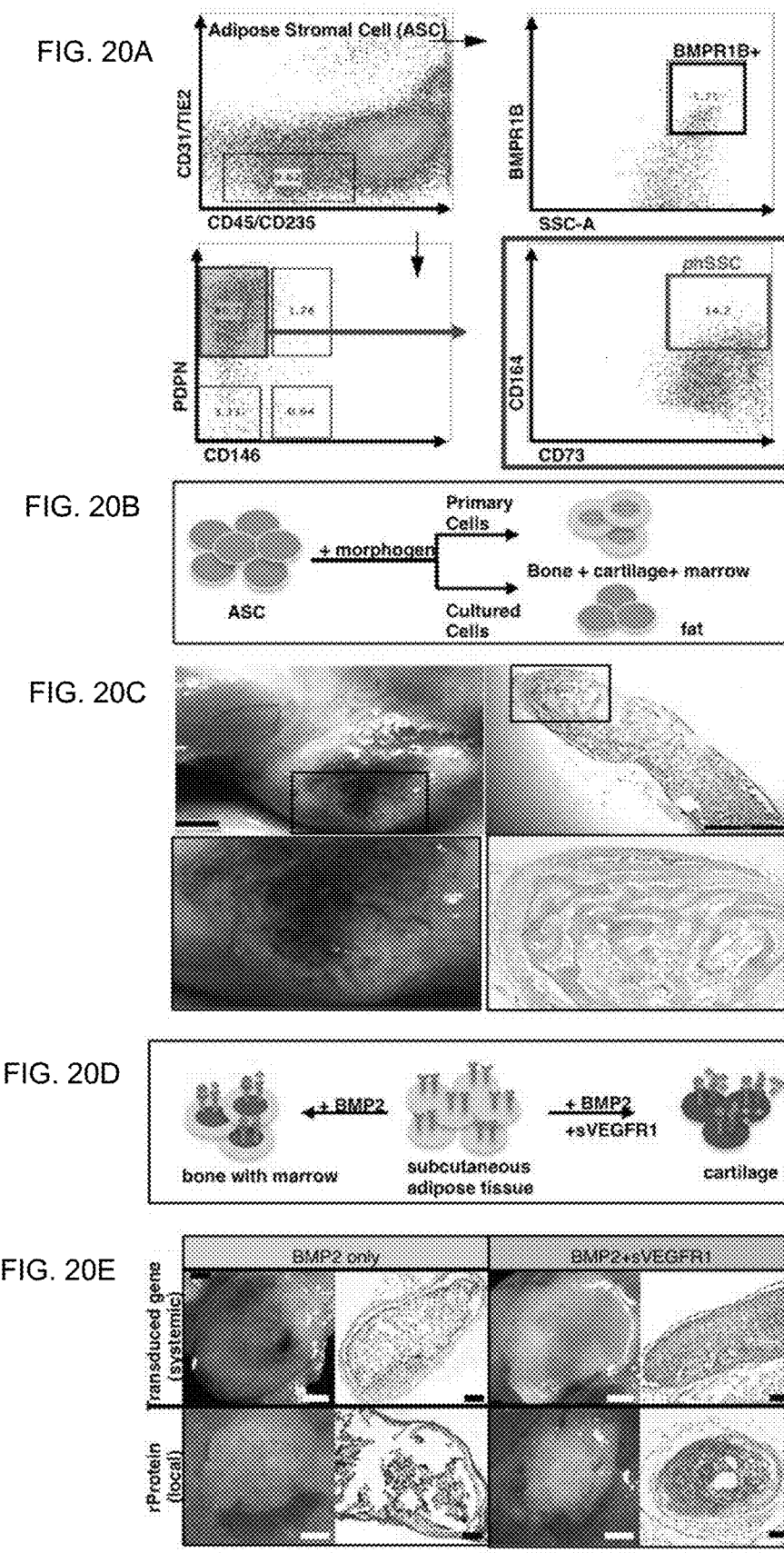

FACTORS AND CELLS THAT PROVIDE FOR INDUCTION OF BONE, BONE MARROW, AND CARTILAGE

CROSS-REFERENCE To RELATED APPLICATIONS

This application is a 371 application and claims the benefit of PCT Application No. PCT/US2016/012347, filed Jan. 6, 2016, which claims benefit of U.S. Provisional Patent Application Ser. No. 62/101,282 filed Jan. 8, 2015, the disclosure of which applications are incorporated herein by reference in their entirety.

GOVERNMENT RIGHTS

This invention was made with Government support under contract HL058770 awarded by the National Institutes of Health. The Government has certain rights in the invention.

BACKGROUND OF THE INVENTION

Almost every family in the United States is affected by diseases involving the skeleton. Myriad etiologies, including degenerative, neoplastic, post-traumatic and post-operative pathology, affect the skeleton. These conditions affect people of all ages, races, ethnicities, and economic strata. The U.S. Health Cost & Utilization Project recently reported that the biomedical burden attributed to diseases of the musculoskeletal system exceeds 47 billion dollars annually, and this figure has continued to increase in recent years at an estimated rate of 8.5% annually. Furthermore, as both the North American and global populations age, a concomitant increase in musculoskeletal disease incidence is expected. This generational change is the most powerful force currently operating in the healthcare system. Alternative approaches to the treatment of skeletal disease must be developed to augment and/or replace contemporary measures.

Bone is unique in that it has an innate capacity for regeneration within specific confines. In addition, the human skeleton is replaced annually in infants and approximately every five to six years in adults, supporting the existence of active stem and progenitor cells in bone tissue that are utilized as sources of new osteogenic cells required for growth, homeostasis and regeneration of postnatal skeletal tissues. Skeletal clinical problems can be addressed by a thorough understanding of how the skeleton develops and is maintained from a stem cell viewpoint.

Tissue-specific adult stem cells inhabit most major organ systems and have been definitively identified in a host of tissues. Stem cell regulation in the skeletal system, as compared to the hematopoietic system, remains relatively unexplored. Pioneering studies by Friedenstein et al. established the presence of colony forming, skeletogenic cells in the bone tissue, but only recently have efforts begun to identify and isolate bone, cartilage, and stromal progenitors for rigorous functional characterization. In addition, the bone marrow is also a favored site of metastasis from prostate and breast cancer and the origin and identity of the bone stroma supporting metastatic stem cell niches is largely uncharacterized. The properties of skeletal progenitors identified by several groups vary depending on the methods of isolation and the types of functional assays that were used. Another important challenge in tissue regeneration is the limited capacity in nature and in the laboratory to (re)generate cartilage, which is deficient in many diseases (e.g., osteoarthritis, connective tissue disorders).

Identification of cells and factors that influence both skeletal and chondrogenic development are of great interest for clinical and research applications. The present invention addresses this issue.

Publications

Publications of interest include Tevlin et al. (2014) J Vis Exp. (93), "Osteoclast derivation from mouse bone marrow"; McCardle et al. (2014) Tissue Eng Part A. 20(21-22): 3031-40, "Positive Selection for Bone Morphogenetic Protein Receptor Type-IB Promotes Differentiation and Specification of Human Adipose-Derived Stromal Cells Toward an Osteogenic Lineage"; Chan et al. (2013) Proc Natl Acad Sci USA.110(31):12643-8, "Clonal precursor of bone, cartilage, and hematopoietic niche stromal cells"; and Levi et al. (2012) Proc Natl Acad Sci USA. 109(50):20379-84, "In vivo directed differentiation of pluripotent stem cells for skeletal regeneration". Chan et al. (2009) Nature January 22; 457(7228):490-4. "Endochondral ossification is required for hematopoietic stem cell niche formation"

SUMMARY OF THE INVENTION

Methods, compositions and kits for producing functional chondrocytes, skeletal cells, bone marrow stromal cells, and progenitor cells thereof are provided. These methods, compositions and kits find use in producing chondrocytes, osteoblasts, stromal cells, and progenitor cells thereof for transplantation, for experimental evaluation, as a source of lineage- and cell-specific products, and the like, for example for use in treating human disorders of the cartilage, bone and hematopoietic system, and in the regeneration of aged or otherwise damaged cartilage and bone.

In some embodiments, compositions and methods are provided for directing differentiation of mammalian of skeletal stem cells, including differentiation into osteogenic, chondrogenic, and stromal lineages. In some embodiments, compositions and methods are provided for directing differentiation of non-skeletal cells, for example pluripotent stem cells, mesenchymal stem cells (MSC), adipose derived stem cells (ASC), etc., into skeletal stem cells.

For in vivo uses, reprogramming factor(s) can be provided systemically or as a localized implant, e.g. in a matrigel or other suitable matrix, and are optionally provided with an effective dose of cells, e.g. ASC, SSC, MSC, committed cartilage progenitor cells (CCP), and the like. Cell culture systems for such methods are also provided. The cells find use in therapeutic methods, e.g. to provide cells for skeletal or chondrogenic replacement therapy; in screening methods, and the like. In some embodiments, the cells are mammalian cells. In some embodiments, the cells are human or mouse cells.

In some embodiments an effective dose of human ASC are delivered in vivo with an effective dose of reprogramming factors, which may include without limitation BMP2, at a site for which regeneration of bone and/or cartilage is desired. The ASC are optionally isolated from the individual that is treated. In other embodiments the ASC are allogeneic, for example they may be cryopreserved in a bank. Also provided is a package (for example a box, a bottle or a bottle and box) that includes an effective dose of such reprogramming factors and a package insert or label that indicates that the factors is to be administered in conjunction with an effective dose of human ASC to a patient for the regeneration of bone and/or cartilage. The packaging optionally further includes suitable reagents for the isolation of human ASC. hASCs can be freshly isolated from lipoaspirate, and are optionally provided with antibodies specific for hematopoietic cells, e.g. CD45, CD235, etc. to deplete hematopoietic cells present in the lipoaspirate.

In other embodiments an effective dose of human SSC are isolated from adult human bone, including without limitation femoral head bone, which SSC can be used in transplantation and other therapeutic purposes as described herein.

In some embodiments, specific combinations of protein factors are identified for reprogramming non-skeletal cells into bones, hematopoietic stroma, and chondrocytes, which may be provided in vitro or in vivo. BMP2 can expand SSCs cells, including in vitro culture expansion. Localized high concentrations of BMP2 trigger activation of a dominant skeletalgenic pathway, resulting in respecification of non-skeletal tissues into SSCs. These reprogrammed SSCs are functionally identical to bone isolated SSCs and are capable of differentiation into bone, cartilage, and stroma.

In some aspects of the invention, methods are provided for treating a subject in need of cell transplantation therapy of skeletal or chondrogenic tissues. In some such embodiments, the subject is contacted with factors and optionally cells using the methods and compositions of the invention. In certain embodiments, the cells are derived from the subject.

In some cell transplantation embodiments, factors and cocktails of factors are provided for directing skeletal stem cells to a chondrogenic fate, which factor(s) may be provided in vitro or in vivo. It is shown that inhibiting VEGF signaling drives SSCs to undergo differentiation into cartilage tissues. It is also shown that inhibition of TGF-$\beta$ signaling can drive SSC to undergo differentiation into cartilage tissues. In some embodiments an effective dose of a VEGF inhibitor is provided to an individual in combination with an effective dose of SSC for regeneration of cartilage. In other embodiments, an effective dose of a VEGF inhibitor is provided to an individual with combination with an effective dose of adipose stem cells and BMP2 for regeneration of cartilage.

In other cell transplantation embodiments, factors and cocktails of factors are provided for directing skeletal stem cells to a osteogenic fate, which factor(s) may be provided in vitro or in vivo. Exposure to wnt proteins, including without limitation Wnt3 and Wnt5 proteins, can enhance SSC differentiation into bone. In some embodiments an effective dose of a Wnt 3 or Wnt 5 agonist, for example including without limitation human Wnt3, human Wnt3a, human Wnt5a, human Wnt5b proteins, or mimetics and derivatives thereof, is provided to an individual in combination with an effective dose of SSC for regeneration of bone. In other embodiments, an effective dose of a Wnt agonist is provided to an individual with combination with an effective dose of adipose stem cells and BMP2 for regeneration of bone.

In some embodiments, an effective dose of an inhibitor of VEGF and/or TGF$\beta$ is provided to an individual for induction of cartilage at a desired site. In some such embodiments, the effective dose is provided in a localized form, e.g. as an implant, including a biodegradable implant, microneedle, depot or other pharmaceutical form as known in the art for localized delivery of an active agent. In some embodiments, an effective dose of a BMP2 agent is co-administered, which dose is effective in driving non-skeletal cells, including without limitation mesenchymal stem cells, into a skeletal fate. The combined formulation allows regeneration of cartilage from endogenous non-skeletal cells. The combination of factors can be delivered with an effective dose of cells, e.g. ASC, SSC, etc. Factors of interest also include factors that drive bone formation, e.g. wnt proteins. Factors of interest also include VEGF.

In further embodiments, an effective dose of a regenerative cell population, including without limitation MSC, such as adipose derived MSC, is also provided as a source of cells for chondrogenesis or skeletogenesis. Such embodiments include, without limitation, implantation in a matrix that serves to localize cells and factors. In some such embodiments the matrix is comprised of a biocompatible and optionally biodedgradable matrix or lattice, e.g. formed from matrigel, polylactic acid, polyglycolic acid, Poly(lactic-co-glycolic acid) (PLGA); collagen, alginate, and the like capable of supporting chondrogenesis in a three dimensional configuration.

In some such embodiments, the factors, optionally in combination with regenerative cells, are introduced into a tissue in need of cartilage repair. Such sites include, without limitation, differentiated cell-related disease states and traumatic injuries including but not limited to: anterior cruciate ligament tears, full-thickness articular cartilage defects, partial-thickness articular cartilage defects.

In some embodiments, compositions and methods are provided relating to mammalian skeletal stem cells (SSC). In some embodiments of the invention, compositions of mammalian skeletal stem cells are provided. In other embodiments, compositions of skeletal lineage committed cells are provided, included cartilage committed cells.

The skeletal stem cells of the invention may be identified, and isolated from cell populations by phenotypic analysis of cell surface markers, or induced from non-skeletal cells. Cell populations of interest for isolation of SSC include bone samples, which generally include bone marrow, and which include without limitation adult bone, e.g. femoral head bone; and sources of mesenchymal stem and progenitor cells that have been induced to differentiate into bone progenitors, e.g. by contacting with an effective dose of BMP2. Sources of such earlier progenitor cells include blood, adipose tissue, bone marrow, and the like.

The progenitor cells of the invention have been characterized in a lineage, as shown in FIG. 2G. Methods and compositions are provided for the separation and characterization of such skeletal lineage cells. The cells may be separated from other cells by expression of these specific cell surface markers. The cells are useful in transplantation, for experimental evaluation, and as a source of lineage and cell specific products, including mRNA species useful in identifying genes specifically expressed in these cells, and as targets for the discovery of factors or molecules that can affect them. Human SSC cell populations are generally negative for expression of CD45, CD235, Tie2, and CD31; and positively express podoplanin (PDPN). A population of cells, e.g. cells isolated from bone tissue, having this combination of markers may be referred to as [PDPN$^+$/146$^-$ cells. The [PDPN$^+$/146$^-$] population can be further subdivided into three populations: a unipotent subset capable of chondrogenesis [PDPN$^+$CD146$^-$CD73$^-$CD164$^-$], a unipotent cellular subpopulation capable of osteogenesis [PDPN$^+$CD146$^-$CD73$^-$CD164$^+$] and a multipotent [PDPN$^+$CD146$^-$CD73$^+$CD164$^+$] cell capable of endochondral (bone and cartilage) ossification.

In mouse tissues, the skeletal lineage is characterized as CD45$^-$, Ter119$^-$, Tie2$^-$, $\alpha_v$ integrin$^+$. The SSC is further characterized as Thy1$^-$ 6C3$^-$ CD105$^-$ CD200$^+$. The committed chondrocyte progenitor is further characterized as Thy1$^+$ 6C3$^-$ CD105$^+$ CD200$^+$.

In vitro and in vivo systems are provided for the growth and analysis, including clonal analysis, of skeletal lineage cells. In particular, it is found that in an in vivo model, the skeletal lineage cells can be localized, e.g. by embedding in a matrix, and will form bone structures. Where the osteochondral progenitors are present the bone will form functional bone marrow niches that support hematopoietic cell function.

Also provided are methods, compositions and kits for screening candidate agents for activity in converting cells into skeletal cells, chondrocytes, and progenitor cells thereof.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1H. Bone and cartilage are derived from clonal, lineage-restricted progenitors. FIG. 1A Tissue micrographs of a 6-week old Rainbow Actin-Cre-ERT mouse femur, following induction with tamoxifen at post-natal day 3. Left: Fluorescent microscopy with higher magnification of the obliquely angled rectangle shown inset denoted by the white square in the centre of the panel which shows clones present at the growth plate of the femur. Middle: Brightfield image of pentachrome-stained mouse femur with higher magnification inset of the obliquely angled rectangle shown inset denoted by the white square in the centre of the panel which shows the growth plate of the femur. Right: Photograph of a coronal section mouse femur. Of note, the broken yellow line depicts the femoral growth plate, the broken purple line depicts the bone matrix, and the broken green line depicts the bone marrow. Scale bar in all figures is equivalent to 500 µM. FIG. 1B FACS plots showing distribution of suspended cells isolated by mechanical and enzymatic digestion from the femoral growth plate (uppermost horizontal panel), flushed bone (middle panel) and bone marrow (bottom horizontal panel). Of the three different parts of the femur, the [AlphaV+] population is most prevalent in the growth plate (uppermost horizontal panel in the middle). DN=double negative, i.e. negative for Thy and 6C3 staining; [CD45-Ter119-Tie2-AlphaV+Thy-6C3-]. FIG. 1C Scheme of experiment: Actin-Cre-ERT transgenic mouse was crossed with rainbow reporter gene mouse. Cre recombination of offspring was induced by tamoxifen injection on embryonic day 15 (E15), post-natal day 3 (P3) and postnatal week 6. Femoral tissue was harvested 6 weeks post induction. FIG. 1D Graphic representation of results illustrating different numbers of clones present, which span the bone and cartilage. After a six week chase period, clonal regions could be determined as uniformly labeled regions of a single color (7 uniquely colored clones were observed, as indicated by "Color 1-7" on the x axis). We do not observe distinct clonal regions capturing bone, cartilage and stromal cells with hematopoietic, adipose or muscle tissue and thus, these have not been represented graphically. FIG. 1E FACS gating strategy for the isolation of eight distinct skeletal tissue subpopulations obtained from the [AlphaV+] subset obtained from the long bones, ribs and sternum of wild-type C57Bl6 mice at postnatal day 3 based on differential expression of four further cell surface markers: Thy, 6C3, CD105, and CD200. Cell populations (a-h) as depicted in the FACS plots correspond to the eight distinct skeletal tissue subpopulations obtained from the [AlphaV+] subset: a=BCSP, b=BLSP, c=603, d=HEC, e=mSSC, f=pre-BCSP, g=CCP, h=Thy. FIG. 1F Histological analysis of a mouse femur at P3 stained with Movat's pentachrome, which contains bone (stains yellow), cartilage (stains blue/green) and bone marrow (stains red). Scale bar equivalent to 200 µM. (Bottom) Histological sections stained with pentachrome of tissue grafts following cell subpopulation transplant beneath the renal capsule: 20,000 highly-purified cells from the eight subpopulations of skeletal tissue in P3 were injected beneath the renal capsule of immunocompromised mice and harvested 30 days after transplantation (Panels 'FIG. 1F(i)' through 'FIG. 1F(viii)' represent the eight cell subpopulations within the [AlphaV+] subset, as illustrated in FACS plot in FIG. 1E). Pentachrome-stained transverse sections of each graft demonstrate bone, cartilage, and bone marrow stroma restricted cell fates of each progenitor cell subpopulation. Populations e [CD45-Ter119-Tie2-AlphaV+Thy-6C3-CD105-CD200+] (mSSC), f [CD45-Ter119-Tie2-AlphaV+CD105-Thy-6C3-CD200-], (pre-BCSP) and a [CD45-Ter119-Tie2-AlphaV+Thy-6C3-CD105+], (BCSP) can reconstruct entire bone environments, consisting of bone, cartilage and a functional marrow cavity. Populations b (BLSP), c (6C3), d (HEC), and h (Thy) formed bone only. Population g (CCP) formed cartilage, in addition to a small amount of bone. Scale bar equivalent to 200 µM. FIG. 1G Graph depicting the percentage tissue composition of each of the explanted grafts ('a' through 'h' represent the eight cell subpopulations within the [AlphaV+] subset, corresponding to FACS plot in FIG. 1E and transplanted tissue in FIG. 1F): percentage of bone is represented by yellow, percentage of marrow is represented by red and percentage of cartilage is represented by blue within the stacked column chart. FIG. 1H Scheme of experiment: 20,000 cells of the eight subpopulations within the [AlphaV+] subset were isolated from the long bones of GFP-labeled mice at P3, following mechanical and enzymatic dissociation. Cells were subsequently fractionated by FACS into the eight cell subpopulations, as detailed above. Purified GFP+ cells were then transplanted beneath the kidney capsules of recipient mice. One-month after transplantation, the grafts were explanted for analysis. FIG. 2A-2G. Identification of the mSSC (mouse Skeletal Stem Cell). FIG. 2A Scheme of experiment: [CD45-Ter119-Tie2-AlphaV+Thy-6C3-CD105-CD200+] (denoted CD200+TN in the schematic, i.e. CD200+ Triple Negative) cells were isolated from femora of GFP+ mice at P3, following mechanical and enzymatic dissociation, antibody staining and FACS fractionation. FIG. 2A(i) Purified [CD45-Ter119-Tie2-AlphaV+Thy-6C3-CD105-CD200+] (mSSC) cells were seeded in a culture plate containing MEMα medium with 10% fetal calf serum. On days 0, 11 and 25 in culture, the cultured cells were harvested for FACS analysis and sorting to determine the constituent cells of the [CD45-Ter119-Tie2-AlphaV+Thy-6C3-CD105-CD200+] (mSSC) cell subpopulation post expansion in culture. On day 25 following re-fractionation of the cells by FACS, 20,000 cells of each subset (mSSC, BCSP, Thy, 6C3) cells were transplanted beneath the kidney capsules of recipient mice. One-month after transplantation, the grafts were explanted for analysis. FIG. 2A(ii) Purified GFP-labeled [CD45-Ter119-Tie2-AlphaV+Thy-6C3-CD105-CD200+] (mSSC) cells were also directly transplanted beneath the kidney capsules of recipient mice (without preceding expansion in culture). One-month after transplantation, the grafts were explanted for, either, analysis by FACS or histology. FIG. 2B(i)-(iii) FACS analysis of cultured [CD45-Ter119-Tie2-AlphaV+Thy-603-CD105-CD200+] (mSSC) on days 0, 11 and 25 in culture FIG. 2B(i), FIG. 2B(ii). At day 25, in vitro cultures were FACS sorted and four subpopulations (mSSC [CD45-Ter119-Tie2-AlphaV+Thy-603-CD105-CD200+], BCSP [CD45-Ter119-Tie2-AlphaV+Thy-603-CD105+], Thy+ [CD45-Ter119-Tie2-AlphaV+Thy+6C3-CD105-] and 6C3+ [CD45-Ter119-Tie2-AlphaV+Thy-6C3+CD105+]) were transplanted beneath the kidney capsule to determine their intrinsic potential. FIG. 2B(iii) mSSC formed bone, cartilage and a marrow cavity (red box). BCSPs (green box), Thy cells (blue box) and 6C3 cells (orange box) formed bone only, without a marrow cavity. Scale bar equivalent to (iii, upper panel) 500 µm, (iii, lower panel) 200 µm. FIG. 2C(i)-(iii) FACS analysis of explanted kidney capsule grafts, one month following implantation, in which highly purified populations of GFP-labeled [CD45-Ter119-Tie2-AlphaV+Thy-6C3-CD105-CD200+] (mSSC) cells were transplanted beneath the kidney capsule. FIG. 2C(i), FIG. 2C(ii) FACS analysis of the explanted grafts revealed that explanted graft consisted of 7 downstream subpopulations (blue, red and orange boxes). Brightfield micrograph of pentachrome-stained explant (FIG. 2C(iii) far left, lower panel) demonstrates that the [CD45-Ter119-Tie2-AlphaV+Thy-6C3-CD105-CD200+] (mSSC) subpopulation is capable of generating bone, cartilage and marrow. A higher magnification fluorescent image of the pentachrome-stained panel on the far left of the lower panel is shown within the purple box extending to the right of the figure. The panels within the purple box show that the mSSC is capable of generating cells that express Thy and 6C3 as observed on immunohistochemistry (FIG. 2C(iii) middle panels; here Thy=red, 6C3=white). Merged panel is at far bottom right (FIG. 2C(iii), bottom right panels). Fluorescent image of GFP+ graft is shown in the lower magnification image on the extreme upper left panel of FIG. 2C(iii). Scale bar equivalent to: (FIG. 2C(iii), upper panel) 500 µm, (FIG. 2C(iii), lower panel) 100 µm, (FIG. 2C(iii), immunofluorescent images) 50 µm. FIG. 2D Scheme of experiment: Cells from the long bones of RFP+ P3 mice were isolated following mechanical and enzymatic dissociation. These cells were not fractionated by FACS and served as feeder cells. Cells from the long bones of P3 GFP+ mice were isolated following mechanical and enzymatic dissociation and [CD45-Ter119-Tie2-AlphaV+Thy-6C3-CD105-CD200+] (mSSC) cells were obtained following FACS. FIG. 2D(i) A single GFP-labeled [CD45-Ter119-Tie2-AlphaV+Thy-6C3-CD105-CD200+] (mSSC) cell was co-transplanted with 5,000 RFP(+) feeder cells beneath the renal capsule of immunodeficient mice FIG. 2D(ii). A single purified GFP-labeled [CD45-Ter119-Tie2-AlphaV+Thy-6C3-CD105-CD200+] (mSSC) cell was plated per well of a 96-well culture dish. Following 14 days in culture, formed colonies were counted, harvested, re-sorted using FACS and a single purified GFP-labeled [CD45-Ter119-Tie2-AlphaV+Thy-6C3-CD105-CD200+] (mSSC) cell was again plated per well of a 96-well culture dish and the assay repeated. FIG. 2E(i)-(iv) In vitro, colony formation assays were performed by plating a single [CD45-Ter119-Tie2-AlphaV+Thy-6C3-CD105-CD200+] (mSSC) cell in each well of a 96-well culture dish. FIG. 2E(i): A representative Phase microscopic image of a primary colony is depicted at 14 days post plating. FIG. 2E(ii): Passaging of primary colonies resulted in the formation of secondary colonies with similar morphology to primary colonies (Phase microscopy). FIG. 2E(iii) Primary colonies stained positive for anti-collagen type 2 (purple), anti-osteocalcin (green), and DAPI (blue) following immunofluorescent staining (Fluorescent microscopy). FIG. 2E(iv) Vertical panel on extreme right depicts FACS analysis of initial [CD45-Ter119-Tie2-AlphaV+Thy-6C3-CD105-CD200+] (mSSC) cells isolated (top), and subsequent primary colony (middle), and secondary colony cell (bottom). Scale bar equivalent to (FIG. 2F(i), FIG. 2F(ii): 500 µm FIG. 2F(iii), 100 µm FIG. 2F(i)-(vii) Microscopy of explanted grafts from beneath the renal capsule (as per FIG. 2D(i)). The extent of the in vivo colony formation from GFP-labeled [CD45-Ter119-Tie2-AlphaV+Thy-6C3-CD105-CD200+] mSSCs is outlined by a yellow broken line in FIG. 2F(i), FIG. 2F(iii), FIG. 2F(v) and black broken line in FIG. 2F(ii), FIG. 2F(iv), FIG. 2F(vi). Clonally expanded, GFP-labeled, [CD45-Ter119-Tie2-AlphaV+Thy-6C3-CD105-CD200+] (mSSC) cells are evident as green cells using fluorescent microscopy in FIG. 2F(i), FIG. 2F(iii), FIG. 2F(iv). Corresponding bright field micrographs are depicted in panels FIG. 2F(ii), FIG. 2F(iv), FIG. 2F(vi). Fluorescent imaging of transverse sections of grafts is depicted in panel FIG. 2F(iii) and FIG. 2F(v). Corresponding bright field micrographs of pentachrome-stained sections demonstrates clonally expanded cells are fated into bone (yellow) and cartilage (blue) (FIG. 2F(iv) and FIG. 2F(vi). Graph in FIG. 2F(vii) is representative of the contribution by the GFP or RFP cells (per cell transplanted) to bone or cartilage formation. Scale bar equivalent to FIG. 2F(i-vi): 200 µm. FIG. 2G Schematic representation of the skeletal stem cell lineage tree. The mSSC occupies the apex of this hierarchal tree and is multipotent, capable of self-renewal, and differentiation into more lineage restricted progenitor cells (pre-BCSP and BCSP). The mSSC, pre-BCSP and BCSP are capable of giving rise to bone, cartilage and hematopoietic supportive stroma. The immunophenotype of each cell is shown adjacent to the cell. Note, we observe that VEGF antagonism results in promotion of a cartilaginous fate (shown in red) while Wnt agonism may promote an osseous fate (shown in green).

FIG. 3A-3L. The mSSC niche is composed of other skeletal-lineage cells. FIG. 3A Scheme of experiment: Long bones of P3 mice were harvested and cells isolated by mechanical and enzymatic dissociation. The cell suspension was sorted by FACS to obtain mSSC; BCSP; Thy (+), which encompasses the CCP, Thy and BLSP subsets; and 6C3 (+), which encompasses 6C3 and HEC. Cell subpopulations were then prepared for single cell RNA sequencing and subsequent analysis. FIG. 3B Hierarchical clustering of single cell RNA sequencing data from four skeletal stem/progenitor subpopulations demonstrate four molecularly distinct patterns of single cell transcriptional expression between the mSSC, BCSP, Thy(+) and 6C3(+). FIG. 3C Percentage transcriptional expression of morphogen, receptor or both on single cell RNA sequencing of the following populations: (order of cells from left to right) mSSC, BCSP, Thy(+), 6C3(+). Order of morphogens and cognate receptors from top to bottom in each row: BMP2/BMPR1a, WNT/FRZ, TGFβ3/TGFβR2. Venn diagrams show the percentage expression of morphogens (left circle in each Venn diagram) and the percentage expression of cognate receptors (right circle in each Venn diagram). Percentage co-expression of morphogen and ligand are shown in the overlapping central portion of the Venn diagram. Note the percentage denotes the percentage of cells within each subset assayed (mSSC, BCSP, Thy(+) and 6C3(+)) which express the relevant gene sequence. The patterns displayed show the potential for autocrine (bottom schematic on left) and paracrine signaling (bottom schematic on right). FIG. 3D Gene expression levels of Wnt-associated genes in skeletal populations as determined using the Gene Expression Commons (GEXC) analysis platform (shown in the following order from top to bottom: mSSC, BCSP, Thy, 6C3, BLSP and HEC). These experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. The range of transcriptional expression, as calculated using GEXC, is illustrated by a color change as depicted on the extreme right of the figure (i.e. dark purple correlates to very high expression, whereas dark blue correlates to minimal expression). This heat map shows high expression of both Wnt-associated ligands (Wnt3a, Wnt4, Wnt5a) and receptors (Fzd5-9), demonstrating that the Wnt signaling pathway may be actively involved in skeletal progenitor function. We also see high expression of SFRP-2 (secreted Fzd related protein 2) throughout the cell populations. Fzd=frizzled receptor. FIG. 3E Ligand-receptor interaction maps. Gene expression analysis of microarray data extracted from skeletal stromal subsets (shown in the following order from top to bottom: mSSC, BCSP, Thy, 6C3, BLSP and HEC) illustrating ligands in the left column and cognate receptors in the right column. As these experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. The two uppermost ligand-receptor interaction maps demonstrate that BMP-2 and BMP-7, important skeletogenic genes, and their cognate receptors are highly expressed in skeletal stromal populations. The bottom three ligand-receptor interaction maps detail the gene expression of TGFβ3, GDF5 and VCAM-1 and corresponding receptors. The ligand-receptor interaction maps demonstrate that the skeletal stromal cells can act as their own niche and signal through each other to promote skeletogenesis. The connecting arrows indicate possible ligand-receptor interaction pathways. Note: GDF=growth and differentiation factor, VCAM-1=vascular cell adhesion molecule-1. FIG. 3F Diagram illustrating potential signaling pathways influencing activity of skeletal stem/progenitor cells. We propose that autocrine and paracrine signaling may occur in the skeletal stem cell niche and regulate cell activity and maintenance. FIG. 3G 5,000 freshly isolated mSSC (obtained from GFP-labeled mice) were co-cultured with various morphogens (BMP2, TGFβ, TNFα). The fluorescent micrographs on the right illustrate the colony morphology post culture with morphogen supplementation, the graph on the left shows the number of mSSC present following culture for 14 days under the different conditions (control or supplementation with BMP2/TGFβ/TNFα). Here, we see that culture of mSSC with rhBMP-2 supplementation was associated with significant amplification of the mSSC populations in vitro (bottom left panel of fluorescent micrographs) in comparison to control, non-supplemented media (top left panel of fluorescent micrographs)(p<0.01, ANOVA). Supplementation with TGFβ or TNFα resulted in an alteration in colony morphology (as shown in right upper and lower panel of fluorescent micrographs). These results show that niche signaling can influence mSSC proliferation. Scale bar equivalent to 200 μm. FIG. 3H The graph on the left of the figure illustrates the effect of recombinant growth factor BMP2 titration on mSSC proliferation in culture. Here, we see that the maximal proliferative effect is seen at a concentration of 50 ng/mL. The effect of BMP-2 was significantly greater than control at each of the following concentrations: 50 ng/mL (p<0.001, ANOVA), 500 ng/mL (p<0.01, ANOVA). The phase images on the right illustrate the colonies of cells derived from the mSSC (indicated by arrowhead in control, 50 pg/mL, 500 pg/mL, 5 ng/mL and by a broken line in 50 ng/mL and 500 ng/mL). Scale bar equivalent to 500 μM. FIG. 3I Gene expression heatmap of Foxa2 illustrates that Foxa2 gene is upregulated in the mSSC. As these experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. FIG. 3J Fluorescence micrograph of the proximal femoral growth plate stained for anti-Foxa2 antibody (red) visualizes the localization of mSSC at the growth plate, which is demarcated by the white broken line. DAPI=blue. Scale bar equivalent to 500 μM. FIG. 3K Intracellular FACS signal illustrating that Foxa2 is present in the mSSC at a protein level. Black peak=mSSC signal, Red peak=isotype signal. FIG. 3L(Left) Fluorescence micrographs of the proximal femur of P3 mice stained for anti-Foxa2 antibody (red) illustrating the presence of mSSC. Anti-6C3 antibody (white) and anti-Thy1 antibody (green) illustrating the presence of 6C3 and Thy cells respectively; and DAPI (blue), which illustrates the mSSC niche. Merged image on right illustrates that mSSC reside mostly at growth plate, with evident niche cells, 6C3 cells (white) and Thy cells (green), surrounding the mSSCs. Scale bar equivalent to 200 μM(extreme left), 500 um (extreme right).

FIG. 4A Scheme of experiment: BCSP were isolated from femora of GFP+ mice at P3 and CCP (committed cartilage progenitor) cells were isolated from ears/sternum of RFP+ adult mice following mechanical and enzymatic digestion, and subsequent fractionation by FACS. Purified GFP+ BCSP and RFP+ CCP were co-transplanted beneath the kidney capsules of immunocompromised recipient mice with and without secreted frizzled-receptor 2, SFRP-2. The transplant of RFP+ CCP alone served as a control. One-month after transplantation, all grafts were removed for analysis. FIG. 4B Microscopy of explanted grafts in which 20,000 RFP-labeled cells of the CCP progenitor subpopulation were transplanted into kidney capsules and explanted one month later (as detailed in FIG. 4A). The white dotted line outlines the extent of the graft formed. Fluorescence micrograph of explanted graft demonstrating the presence of an RFP+ graft (upper left). Corresponding bright field micrograph is shown in upper right panel. Transverse section stained with Movat's Pentachrome (which stains bone yellow, cartilage blue, and bone marrow red) demonstrates that RFP-labeled CCP cells form cartilage, as indicated by blue stain. (Fluorescent micrograph: bottom left, Brightfield micrograph: bottom right) Scale bar equivalent to (upper panel): 500 μm, (lower panel) 200 μm. FIG. 4C Microscopy of explanted grafts in which 20,000 RFP-labeled CCP cells were cotransplanted with 20,000 GFP-labeled BCSPs beneath kidney capsules and explanted one month later (as detailed in FIG. 4A). The grafts, which subsequently formed, are outlined by a white dotted line (indicating RFP+ portion of graft) and a yellow solid line (indicating GFP+ portion of graft) (upper Left). A corresponding bright field micrograph is shown in the upper right panel. A transverse section with Movat's pentachrome stain demonstrates that both RFPlabeled CCPs and GFP-labeled BCSPs form bone, as indicated by the yellow stain. (Fluorescent micrograph: bottom left, Brightfield micrograph: bottom right Scale bar equivalent to (upper panel): 500 μm, (lower panel) 200 μm. FIG. 4D Microscopy of explanted grafts in which 20,000 RFP-labeled CCPs were co-transplanted with 20,000 GFP-labeled BCSPs pre-treated with 108/109 units of adenoviral vectors encoding expression of soluble frizzled-related protein 2 (SFRP-2) beneath the kidney capsule (as detailed in FIG. 4A). The resulting grafts, harvested after one month are shown. Fluorescence micrograph (upper left) outlines the GFP+ population (within the yellow solid line) and the RFP+ population (within the white dotted line). The corresponding bright field micrograph is shown (upper right). Micrographs of transverse sections are shown in the bottom panel. Fluorescence micrograph of transverse section of graft is shown (bottom left) and brightfield micrograph showing staining of this section with Movat's Pentachrome (bottom right) demonstrates that RFP-labeled CCP cells form cartilage, as indicated by the blue stain but GFP-labeled BCSPs form bone, as indicated by the yellow stain. Scale bar equivalent to (upper panel): 500 μm, (lower panel) 200 μm.

FIG. 5A-5F. Cartilage fate in mSSC is promoted in the absence of VEGF/PlGF signaling in the microenvironment. FIG. 5A Scheme of experiment: mSSC were isolated from P3 mice by mechanical and enzymatic dissociation and subsequent fractionation by FACS. Either intact pre-osteogenic femora isolated from E14.5 mice or 20,000 mSSC were then transplanted beneath the kidney capsule of immunodeficient recipient mice with and without systemic inhibition of VEGF/PlGF signaling. To study inhibition of VEGF/PlGF signaling, adenoviral vectors encoding soluble VEGFR1 ectodomain (Ad sVEGFR1) were delivered intravenously to the designated recipient mice 24 hours prior to kidney capsule cell transplantation, leading to systemic release of this potent antagonist of VEGF/PlGF signaling in the circulation. For negative control, Ad Fc encoding an immunoglobulin Fc fragment was used. FIG. 5B Systemic inhibition of VEGF/PlGF signaling leads to chondrogenic differentiation of intact pre-osteogenic fetal bones or mSSC in vivo. Intact fetal bone or mSSC were transplanted beneath the kidney capsule of immunocompromised mice that had been pre-treated with Ad sVEGFR1. The grafts were explanted after one month. Brightfield micrographs of explanted grafts are shown in the first and third row from the top of the panel (control, Ad Fc in left panel and treated, Ad sVEGFR1 in the right panel). Representative sections stained with Movat's pentachrome stain are shown in the second and fourth rows from the top of the panel. (top two rows: intact fetal bone, bottom two rows: mSSC) Inhibition of VEGF/PlGF signaling resulted in the formation of cartilage (blue) (right), with the Ad Fc group forming bone (yellow) (left). Scale bar equivalent to: (Intact fetal bone, top panel): 500 μm; (Intact fetal bone, bottom panel): 100 μm; (mSSC, top panel): 500 μm; (mSSC, bottom panel): 200 μm. FIG. 5C Graphic representation of the fate of the mSSC/fetal bone transplants in the presence of Ad sVEGFR1 (antagonism of VEGF signaling) or Ad Fc control. Here, we see promotion of cartilaginous fate in the presence of systemic VEGF antagonism. FIG. 5D Using GEXC, VEGF signaling pathways were determined in six of the skeletal progenitor subpopulations (as listed from top to bottom: mSSC, BCSP, Thy, 6C3, BLSP and HEC). Gene expression analysis of mSSC and its downstream progeny reveal little expression of traditional VEGF receptors such as Flt1, Kdr, and Flt4 but, contrastingly, high expression of VEGF/PlGF receptor homologues, Nrp1 and Nrp2. Skeletal stem/progenitors do not express VEGFA or VEGFB but do express VEGFC and PlGF Please note that, as these experiments were performed prior to further refinement with CD200, the *mSSC population studied represents the triple negative cell populations [CD45-Ter119-Tie2-AlphaV+Thy-CD105-6C3-] which includes both the CD200+/− cell populations, and thus illustrates the transcriptional expression data of the mSSC/pre-BCSP. FIG. 5E Scheme of experiment: mSSCs were isolated from long bones of P3 C57BL6 wild-type mice. These cells were cultured in the presence of recombinant proteins. There were 4 experimental groups and one control. The experimental groups were treated with the following soluble recombinant proteins for one week prior to transplantation into the subcutaneous fat of the inguinal fat pad: (I) NRP1, (II) PlGF, (III) VEGF and (IV) VEGFR1. The grafts were subsequently explanted at three weeks for histological analysis. FIG. 5F Three weeks following transplantation, the grafts as described in the legend of FIG. 5E were explanted for histological analysis. Samples listed from left to right: control (no treatment), PlGF, sNRP1, VEGFA, sVEGFR1. Photographs of the macroscopic appearance of each of the grafts are shown in the upper panel: note, that each of these grafts have a reddish appearance (Again: samples listed from left to right: control, PlGF, sNRP1, VEGF, sVEGFR1). Brightfield images of the explanted grafts stained with Movat's Pentachrome (Again: samples listed from left to right: control, PlGF, sNRP1, VEGF, sVEGFR1). Here we see that all of the grafts give rise to predominantly bone and marrow. mSSCs pretreated with PlGF, sNRP1, VEGF, sVEGFR1 give rise to bone and marrow, with a small amount of cartilage. Scale bar equivalent to: (upper panel) 1 mm; (bottom panel) 200 μm.

FIG. 6A Collagen sponges containing 3 ug of lyophilized recombinant BMP2 were placed into extraskeletal sites in C57BL6 wild-type mice, either beneath the renal capsule or subcutaneously into the inguinal fat pad. One month later, the graft was explanted for analysis. (Left panels) Brightfield images of explants, with renal capsule transplant shown above and subcutaneous transplant shown below. (Right panels) Transverse sections stained with Movat's Pentachrome demonstrate that induced osseous osteoids were replete with a marrow cavity (as denoted by red staining). Scale bar equivalent to: (left panel) 500 μm; (right panel) 200 μm. FIG. 6B FACS analysis of cells present within the osteoids (bottom horizontal panel), formed by BMP2 induction in extraskeletal sites, reveals high levels of engraftment by circulating SlamF1 positive HSCs (depicted by green population on FACS plot on extreme right), similar to normal frequency of HSC engraftment in a "normal" adult femur in a mouse (depicted by green population on FACS plot on extreme right) (top horizontal panel). FIG. 6C(Left Panels) Following explantation of BMP2-laced collagen sponges at day 10 post placement into extraskeletal sites, FACS analysis of constituent cell populations present within the graft revealed that mSSC (depicted by red box on FACS plot) and BCSP (depicted by green box on FACS plot) are readily detectable in the BMP2 treated explants. (Right Panels) In contrast, FACS-analysis of adipose tissue in the absence of BMP2 does not detect either mSSC (depicted by red box on FACS plot) or BCSP (depicted by green box on FACS plot). Scale bar equivalent to 500 μm. FIG. 6D To determine if the ectopic skeletal progenitors were formed by BMP2-induced skeletal commitment in situ or if BMP2 promoted migration of circulating skeletal progenitors recruited from bone tissue, we implemented a parabiont model to determine the origin of the skeletal progenitors in the BMP2 implants. A GFP-labeled mouse was paired to a non-fluorescent wildtype mouse and subsequently fused surgically. Two weeks after surgery, physiological chimerism was verified by measuring the portion of GFP-labeled peripheral blood cells present in the circulating blood of the wild type mouse. A collagen sponge containing 3 ug of lyophilized recombinant BMP2 was transplanted into the inguinal fat pad of the wild type mouse to induce ectopic bone formation. Ten days after implantation, we explanted the tissue and performed mechanical and chemical dissociation to isolate the constituent cell populations of the ectopic bone tissue. We then assayed the contribution of the GFP-labeled cells to ectopic bone formation in the non-GFP mouse by FACs analysis as shown in the horizontal upper panel depicting the FACS analysis plot (i.e. GFP+=circulating cells, and non-fluorescent=local cells). While we detected abundant GFP-labeled cells in the implant at harvest, the GFP-labeled cells which contributed to the graft were solely CD45(+) hematopoietic cells (extreme left panel, top and bottom), and not consistent of the skeletal progenitor population (horizontal upper panel, mSSC population shown in red box on extreme right). The skeletal progenitor population present in the explanted tissue at harvest was entirely GFP-negative suggesting that circulating skeletal progenitor cells did not contribute to BMP2-induced ectopic bones. [green cells present in the extreme right FACS plot do not represent GFP-labeled cells.] FIG. 6E(Left panel) Diagram of reporter gene mouse model shows that Tie2 expression leads to GFP expression. In result, Tie2+ cells turn green but Tie2-cells remain red. (Right panel) Scheme of experiment: In order to determine the cell types, which could undergo BMP-2 mediated reprogramming to mSSC in extraskeletal sites, we implemented a Tie2Cre x MTMG reporter mouse and placed a collagen sponge containing 3 μg of lyophilized recombinant BMP2 into the subcutaneous fat in the inguinal fat pad. The ossicle was explanted at one month later for histological analysis. FIG. 6F Fluorescence micrograph of sectioned tissue illustrates that BMP-2 derived ossicles (depicted by yellow broken line) clearly incorporate both GFP+ Tie2+ derived osteocytes with visible canaliculi and Tie2-negative RFP-labeled osteocytes, thus suggesting that both Tie2-positive and Tie2-negative lineages could both undergo BMP2-induced skeletal reprogramming. Are denoted by white line is shown at higher magnification in the box on the extreme right, which shows the presence of (GFP+) Tie2+ canaliculi in the presence of (RFP+) Tie2− cells. Scale bar equivalent to 500 μM (left) 50 um (right).

FIG. 7A Scheme of experiment: co-delivery of BMP2 and soluble VEGFR1 to in situ adipocytes. BMP2 in addition to inhibition of VEGF/PlGF signaling leads to chondrogenic differentiation of adipose tissue. BMP2 alone (i.e. with no inhibition of VEGF/PlGF) leads to osteogenic differentiation. FIG. 7B Fate of subcutaneous collagen sponge implants containing BMP2 without VEGFR blockade (left panels) or with VEGF blockade (right panels). One month after placement of collagen sponge containing 3 ug of lyophilized recombinant BMP2 with/without systemic/local VEGFR blockade, the grafts were explanted for analysis. Brightfield images of grafts (left) are shown alongside representative sections stained with Movat's pentachrome (right). The co-delivery of BMP2 and VEGFR resulted in the formation of blue staining cartilage (extreme right panels, top and bottom). The result following systemic VEGF blockade is shown in the top series on the right, while the result of local VEGF blockade is shown in the bottom series on the right. Scale bar equivalent to (panels moving from right to left): (extreme right) 1 mm; (inner right) 200 μm; (inner left) 1 mm; (extreme left) 200 μm. FIG. 7C FACS plot analysis of the constituent cells of the induced cartilage (top horizontal panel) (experimental scheme as shown in FIG. 7A) versus those of freshly isolated cells from ear cartilage of age-matched mice (bottom horizontal panel) demonstrates the majority of both the induced and natural cartilage tissue is within the CCP (committed cartilage progenitor) subpopulation. FIG. 7D Gene expression for ligands and receptors associated with BMP2 and VEGF/PlGF signaling pathway in adipogenic populations (top: ligands, bottom: receptors). (T+P+: CD45(−)Tie2(+)PDGFR((+), T−P+: CD45(−)Tie2(−) PDGFR((+)) FIG. 7E Gene expression for Sox9 (transcription factor of bone morphogenetic protein-2-induced chondrogenesis), Runx2 (a key transcription factor for osteoblastogenesis), Sp7 (bone specific transcription factor required for osteoblast differentiation and bone formation) and Foxa2 genes in adipogenic populations (right). (T+P+: CD45(−)Tie2(+)PDGFR((+), T−P+: CD45(−)Tie2(−)PDGFR((+)).

FIG. 8A-8D(xii): Postnatal clonal expansions are restricted to bone, cartilage and stromal fates. FIG. 8A Rainbow Quantification Scheme: fluorescent image shown of the femoral growth plate of a P3 mouse. Clones (>/=5 congruent cells of a single color) are shown by the white broken line. 5 color combinations are shown, numbered 1-5 in the image. Definition of clone is shown on the lower right. Scale bar equivalent to 100 μM. FIG. 8B Scheme of experiment: Actin-Cre-ERT transgenic mouse was crossed with rainbow reporter gene mouse. Cre recombination of offspring was induced by tamoxifen injection on embryonic day 15 (E15), post-natal day 3 (P3) and postnatal week 6. Femoral tissue was harvested 6 weeks post induction. FIG. 8C(i)-(vi) Fluorescent micrographs of the femoral growth plate following induction at different timepoints (vertical panel on left FIG. 8C(i), FIG. 8C(ii): induction at E15; middle panel FIG. 8C(iii), FIG. 8C(iv): induction at P3; vertical panel on right FIG. 8C(v), FIG. 8C(vi): induction at 6 weeks). Arrowheads demonstrate the clones present. Note the mild reduction in clonal regions following induction at 6 weeks. High magnification insets depicted of the area shown by a broken white rectangle are shown in the insets of the corresponding figure: FIG. 8C(ii), FIG. 8C(vi) and FIG. 8C(iv) as illustrated. Scale bar equivalent to 500 μm. FIG. 8D(i)-(xii)A 6 week old Actin-Cre/rainbow mouse, induced with tamoxifen at post-natal day 3 (P3) and sacrificed at week 6. FIG. 8D(i) Low power view of the proximal segment of a femur, with areas corresponding to (a) growth plate, (b) bone marrow, (c) fat and (d) vasculature. The representative higher magnification panels depict the femoral growth plate FIG. 8D(ii), FIG. 8D(iii); bone marrow FIG. 8D(iv), FIG. 8D(v), FIG. 8D(vi); fat FIG. 8D(vii), FIG. 8D(viii), FIG. 8D(ix); and blood vessel FIG. 8D(x), FIG. 8D(xi), FIG. 8D(xii). Fluorescent micrographs demonstrate clonal regions of cells at only one site—the growth plate FIG. 8D(ii)—with each clone appearing as a stack of cells of the same color. There are no significant clonal regions (which would be depicted as a stack of cells of the same colour) shown at the bone marrow stroma FIG. 8D(iv), fat FIG. 8D(vii), and vasculature FIG. 8D(x). HSCs, blood vessels and fat in tissue sections were immunostained with anti-CD45, anti-CD31, and anti-perilipin A, respectively, as shown in panels FIG. 8D(vi), FIG. 8D(xii) and FIG. 8D(ix). Note: images FIG. 8D(ii), FIG. 8D(iv), FIG. 8D(vii) and FIG. 8D(x): fluorescent microscopy; images FIG. 8D(iii), FIG. 8D(v), FIG. 8D(viii), FIG. 8D(xi): brightfield microscopy of sections following pentachrome staining. Scale bar equivalent to FIG. 8D(i) 500 µm; FIG. 8D(ii-ix) 50 µm, FIG. 8D(x, xi, xii) 200 µm. FIG. 8E(i)-(iii)Actin Cre/Rainbow mouse induced at P3 and harvested 6 weeks later. FIG. 8E(i) Brightfield image of sternum FIG. 8E(ii) Fluorescent micrographs show the sternum with clones again illustrated by a stack of cells of the same colour. FIG. 8E(iii) High magnification inset denoted by white box. Scale bar equivalent to: FIG. 8E(i), FIG. 8E(ii) 500 µm, FIG. 8E(iii) 200 µm. FIG. 8F(i)-(iii) Actin Cre/Rainbow mouse induced at P3 and harvested 6 weeks later. FIG. 8F(i) Brightfield image of ribs FIG. 8F(ii) Fluorescent micrographs show the ribs with clones again illustrated by a stack of cells of the same colour. FIG. 8F(iii) High magnification inset denoted by white box. Scale bar equivalent to: FIG. 8F(i), FIG. 8F(ii) 500 µm, FIG. 8F(iii) 50 µm. FIG. 8G(i)-(iii) Actin Cre/Rainbow mouse induced at P3 and harvested 6 weeks later. FIG. 8G(i) Brightfield image of whole paw FIG. 8G(ii) Fluorescent micrographs show the paw with clones again illustrated by a stack of cells of the same colour. FIG. 8G(iii) High magnification inset of phalanx denoted by white box. Scale bar equivalent to FIG. 8G(i), FIG. 8G(ii) 1 mm; FIG. 8G(iii) 200 µm.

FIG. 9A Scheme of experiment: Stabilized transverse mid-diaphyseal femoral fractures were created in the right lower limb of wild-type mice aged 8 weeks. The femoral callus was subsequently harvested at day 3/week 1/week 3 and constituent cells were isolated by mechanical and enzymatic dissociation. The cells were then stained and fractionated by FACS. Left-sided femurs were not injured and instead, acted as the unfractured control. The mSSC from the uninjured femora and injured femora were then transplanted beneath the kidney capsule of immunodeficient mice and the tissue was explanted 1 month later for histological analysis. FIG. 9B Bar graphs illustrating the number of mSSC present in the uninjured intact femur and femoral callus at different time points. This shows a significant increase in the number of the mSSC seen at week 1, with subsequent return to baseline mSSC number in the fracture callus in the later stages of fracture healing (week 3). This observation supports vigorous proliferation of mSSC occurring in response to bony injury. ($p<0.01$, t-test). Number of mSSC per 100,000 cells analyzed of each sample denoted beneath the x-axis. FIG. 9C(Left panel) 20,000 mSSC were freshly isolated from a callus at one-week post fracture (top) and from an uninjured femur (bottom). The cells were cultured in the presence of osteogenic differentiation media for 2 weeks and then subjected to Alizarin red staining. Here, we see significantly greater Alizarin red staining of the mSSC obtained from the fracture microenvironment in comparison to those isolated from the uninjured femur, suggesting enhanced osteogenic potential of the mSSC post injury ($p<0.01$, t-test). (Right panel) Brightfield image of the explanted grafts: (top) tissue obtained from transplantation of mSSC isolated from the fracture callus, (bottom) tissue obtained from transplantation of mSSC isolated from the uninjured femur. Scale bar equivalent to: (left panel, in vitro) 500 µm; (right panel, in vivo) 1 mm. FIG. 9D Bar graphs illustrating the number of mSSC present in the following samples: (i) nonirradiated femur one week post fracture, (ii) irradiated femur one week post fracture, (iii) nonirradiated, uninjured femur, (iv) irradiated, uninjured femur. This shows a significant decrease in the number of the mSSC seen at week 1 post fracture following irradiation in comparison to the non-irradiated control ($p<0.01$, t-test). This also shows a significant decrease in the number of mSSC in an uninjured femur following irradiation in comparison to the non-irradiated control ($p<0.01$, t-test). This shows that irradiation reduces the expansion of the mSSC.

FIG. 10A-10E: mSSC progeny translate systemic signals for parental mSSC. FIG. 10A Ligand-receptor interaction maps showing gene expression levels of the BMP antagonists gremlin-2 and Noggin (right top and bottom respectively), which are found to be expressed on progenitor subpopulations downstream of the mSSC, specifically the Thy and BLSP subpopulations. We also note that there is increased gene expression of the receptors for the systemic hormones leptin and thyroid stimulating hormone (TSH) on the same subpopulations of downstream progenitors, Thy and BLSP (left top and bottom panels), which are seen to express antagonists of the BMP2 pathway. Viewing the left and right panels in unison, the ligand-cognate receptor interaction graph demonstrates that signaling through the systemic hormones leptin and TSH receptors may produce inhibitory signals for mSSC expansion by BMP2 antagonism (via gremlin 2, noggin) and subsequent osteogenesis in skeletal stromal populations. Arrows illustrate the potential receptor-ligand interactions. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. FIG. 10B 10,000 mSSC were cultured in a number of various conditions: regular media (control), conditioned media (CM) from Thy subpopulations treated with or without recombinant leptin protein (Thy CM+leptin/Thy CM−leptin) and CM from BLSP populations treated with and without recombinant leptin protein (BLSP CM+leptin/BLSP CM−leptin). Here, we note that CM from both Thy and BLSP cultured without leptin reduce the expansion of mSSC in comparison to control. However, CM from both Thy and BLSP cultured with leptin further reduce the expansion of mSSC in comparison to control or Thy/BLSP subpopulation CM from cells not treated with leptin. Thus, leptin signaling reduces the growth potential of mSSC in vitro. FIG. 10C Gene expression levels of leptin (left) and its receptor (right) in skeletal stromal populations. Negative expression of ligand but high expression of receptor implies that leptin is provided extrinsically Please note that, as these experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. FIG. 10D(i)-(iii) 10,000 freshly isolated Thy cells were cultured in serum-free media supplemented with or without recombinant leptin (1 µg/mL) in vitro and cells were subsequently harvested for qRTPCR at 14 days post plating. FIG. 10D(i) Relative gene expression levels for Noggin, Gremlin 2 and Leptin receptor in the Thy subset treated with or without recombinant leptin are shown in the graph. The graph demonstrates that the Thy subset cultured in the presence of leptin results in upregulation of transcriptional expression of Noggin, Gremlin2 and Leptin receptor, thus strengthening our hypothesis that a connection may exist between the systemic circulation and the skeletal progenitor subpopulations. FIG. 10D(ii) Immunohistochemistry of Thy cells cultured without leptin supplementation. Red stain illustrates Gremlin 2 expression. FIG. 10D(iii) Immunohistochemistry of Thy cells cultured with leptin supplementation. Red stain illustrates Gremlin 2 expression. Here, we can see increased expression of Gremlin 2 following supplementation of culture medium with leptin (1 µg/mL). Scale bar equivalent to 100 µm. FIG. 10E Schematic of proposed pathways influencing mSSC function. Leptin, a circulating systemic factor, activates leptin receptor present on Thy and BLSP cells, which leads to expression of Gremlin 2 and Noggin by Thy and BLSP cells (see FIG. 3D), which antagonizes BMP-2 signaling and subsequent BMP2-induced mSSC proliferation. By contrast, mSSC proliferation is promoted through BMP-2.

FIG. 11A Scheme of experiment: mSSCs were isolated from long bones of P3 C57BL6 wild-type mice. These cells were cultured in the presence of recombinant proteins. There were 2 experimental groups and one control. The experimental groups were treated with the following soluble recombinant proteins for one week prior to transplantation into the subcutaneous fat of the inguinal fat pad: (I) TGF β, (II) TGF βR. The grafts were subsequently explanted at three weeks for histological analysis. FIG. 11B (Left panels) mSSCs pre-treated with TGFβ. Above, we see the photograph of the graft at explantation. Below: we see the pentachrome stained histological specimen, which does not show gross bone or cartilage formation. (Right panels) mSSCs pre-treated with TGFβR. Above, we see the photograph of the graft at explantation. Below: we see the brightfield images of explanted tissue stained with pentachrome, which shows the explanted graft consistent of mostly cartilage (blue) with little bone formation. Scale bar equivalent to: (upper panels) 1 mm; lower panels) 200 µm.

FIG. 12AC-Kit, IL-3 and IL-9 ligands, which are essential for supporting hematopoiesis, are expressed on skeletal stromal subsets. Graph demonstrates the ligand-cognate receptor interaction between skeletal stroma and hematopoietic cells. (Note MEP=megakaryocyte erythroid progenitor, GMP=granulocyte macrophage progenitor, CLP=common lymphoid progenitor). Please note that, as these experiments were performed prior to further refinement with CD200, the *mSSC population studied represents the triple negative cell populations [CD45-Ter119-Tie2-AlphaV+Thy-CD105-6C3-], which includes both the CD200+/− cell populations, and thus illustrates the transcriptional expression data of the mSSC/pre-BCSP. FIG. 12B Diagram of the proposed interaction between skeletal niche and hematopoietic niche illustrates that skeletal stroma cells secrete regulatory molecules and cytokines to local niche and hematopoietic niche, respectively. Those signaling molecules are involved in the proliferation and differentiation of both mSSC and HSC.

FIG. 13B The FACS gating strategy illustrates that mSSC are present in the Mx1-Cre-expressing cells. This demonstrates that Mx1-labeled cells are a non-specific marker for mesenchymal progenitors cells. Mx1 expressing cells (GFP+) are identified within the CD45+, Tie2+, and [AlphaV+] subsets. 12.6% of the cells of the [CD45(−)Ter119(−)Tie2(−)AlphaV(+)Thy(−)6C3(−)] population (which includes the mSSC) were Mx1-CRE positive, which is demonstrated in the bottom panel in the second FACS plot from the extreme right of the figure.

FIG. 14A-14F: mSSC heterogeneity reflects difference in skeletal structure. FIG. 14A Diagram of mouse skeletal anatomy illustrates different shapes and sizes in bones. Each of the numbered bones were harvested, mechanically and enzymatically dissociated and stained for FACS analysis to identify the number of mSSC present in 1 million cells isolated from each bone subset. FIG. 14B Bar graphs demonstrate the numbers of mSSC present in 1 million cells from each isolated bone. The relative numbers of mSSC are not uniform across all bone subtypes and are more likely to increase in the distal components of the appendicular skeleton. FIG. 14C Table shows the count of colony forming unit (CFU) of mSSC isolated from different mouse bones. 500 double-sorted mSSC from each bone subset were plated on a 10 cm tissue culture dish containing MEMα medium with 10% FBS and CFU were counted at 14 days later. Here, we again see heterogenous capacity for colony formation across the different bone subtypes. FIG. 14D Phase microscopic images of formed colonies shown at 40× after 14 days in culture. There is gross heterogeneity evident in the morphology of the colonies formed by different bones. Scale bar equivalent to 200 µm. FIG. 14E After CFU were counted at 14 days post plating, the cells were stained and analyzed by FACS to determine the constituent cells present in the colonies. Analysis of the formed colonies from each bone subset demonstrates heterogeneity in differential potentials for the mSSC, dependent on the type of bone from which it was isolated. FIG. 14F Cell counts of four sub-populations (AlphaV+, Thy, 6C3 and Double Negative (DN)=Thy-6C3-) from each bone subset at two time points imply that proliferation rate of each subpopulation also varies depending on the origin of the cells.

FIG. 15A-15J(ii): Proposed signaling pathways affecting mSSC and progeny FIG. 15A Phase microscopic images of mSSC one week post culture (10,000 mSSC initially plated post FACS), under three different experimental conditions (BMP2 (0.1 µg/mL)/Noggin (1 µg/mL)/Gremlin 2 (1 µg/mL) supplementation of normal media) or control (normal media: (MEM, 10% FBS, 1% Penicillin-Streptomycin). Under these conditions, we note the following: Noggin and Gremlin 2 supplementation of culture media result in decreased proliferation of hypertropic chondrocytes (white arrow) typical of untreated mSSC cultures in vitro in comparison to control or BMP2 supplementation (expansion of hypertropic chondrocyte regions). Scale bar equivalent to 500 µm. FIG. 15B(i) 10,000 mSSCs were freshly sorted and cultured in regular media (upper row of FACS plots) or in regular media with supplementation (2 µg/mL) of Wnt3a (lower row of FACS plots). One week later, the cells were re-isolated, stained with antibodies and underwent FACS fractionation. Here, we noted an increase in the Thy subpopulation (shown in red box), which is pro-osteogenic. FIG. 15B(ii) Pentachrome stained sections of ossicles formed from 5000 cells wnttreated vs non-wnt treated SSCs transplanted to renal capsule for one month. Treatment with Wnt appeared to inhibit endochondral ossification by SSC as evidenced by reduced marrow cavity formation in the Wnt treated samples. Scale bar equivalent to 200 µm. FIG. 15C Gene expression data of Axin1 expression by the mSSC and the downstream progenitors (BCSP, Thy, 6C3, BLSP, CCP). Here, we see reduced expression of Axin 1 by CCP in comparison to other stem/progenitor cells. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FIG. 15D To ensure that the [CD45+Ter 119+] or [Tie2+] subpopulations did not contain high-frequency subpopulations of skeletogenic cells, we isolated the [CD45+Ter 119+] and [Tie2+] cell populations (which we had previously excluded on FACS fractionation) from the long bones of P3 GFP-labeled mice by mechanical and enzymatic digestion and subsequent FACS fractionation. We then transplanted 20,000 cells of each of the subsets beneath the renal capsule of immunodeficient RAG-2/gamma(c)KO mice to assess their intrinsic skeletogenic potential. Unlike the eight subpopulations of the [AlphaV+] fraction, the CD45/Ter119+ and Tie2+ subsets were not found to form bone, cartilage or stroma four weeks after transplantation. Brightfield micrographs of the tissue present 4 weeks post transplantation are shown in the panel on the left, with fluorescent images shown on the right. Populations transplanted are shown in the following order (from top to bottom) in both rows: top [CD45+Ter119+AlphaV-], middle [Tie2-AlphaV+], bottom [Tie2+AlphaV-]. Yellow broken line represents the auto fluorescent sponge scaffold, green broken line represents true GFP+ tissue. Following transplantation of [CD45+ Ter119+AlphaV-] transplanted cells, there is no true green fluorescence and thus, no true tissue engraftment, however there is autofluorescence (yellow broken line) present in the sponge. Following transplantation of [Tie2-AlphaV+] population (red box), we see there is bone tissue formation, represented by the green broken line. Following transplantation of the Tie2+AlphaV-population, there is some green fluorescent tissue present, however, this was not consistent with bone tissue, instead forming a fibrous tissue (high magnification inset), with tubular structures present (likely representing blood vessels, depicted by white arrows in the high magnification inset). Left, right panels: scale bar equivalent to 1 mm. FIG. 15E(i) Gene expression levels of leptin (left) and its receptor (right) in skeletal stromal populations. Negative expression of ligand but high expression of receptor in Thy subset implies that leptin is provided extrinsically. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FPKM: Fragments Per Kilobase of transcript per Million mapped reads FIG. 15E(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of Leptin Receptor by the mSSC and downstream progeny. This illustrates that there is no expression of Leptin Receptor by mSSC (green) and BCSP (turquoise) populations, in comparison to downstream progeny (6C3–purple, Thy–red). FIG. 15F(i) Gene expression levels of FoxA2 in skeletal stromal populations. Here, we see marked expression of FoxA2 in the mSSC in comparison to downstream progeny. Please note that, as these experiments were performed prior to further refinement with CD200, the *mSSC population studied represents the triple negative cell populations [CD45-Ter119-Tie2-AlphaV+Thy-CD105-603-], which includes both the CD200+/– cell populations, and thus illustrates the transcriptional expression data of the mSSC/pre-BCSP. FIG. 15F(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of FoxA2 at a single cell level. Consistent with FIG. 15F(i), we observed that Foxa2 is significantly upregulated on the mSSC, at much lower levels in CSPs, and almost non-existent on downstream progeny. FIG. 15G(i) Gene expression levels of Runx2 in skeletal stromal populations. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FIG. 15G(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of Runx2. FIG. 15H(i) Gene expression levels of Collagen 2A in skeletal stromal populations. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FIG. 15H(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of Collagen 2A. FIG. 15I(*i*) Gene expression levels of Collagen 10A in skeletal stromal populations. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FIG. 15I(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of Collagen 10A. FIG. 15J(i) Gene expression levels of Sox9 in skeletal stromal populations. Please note that, as these experiments were performed prior to further refinement with CD200, the *mSSC population studied represents the triple negative cell populations [CD45-Ter119-Tie2-AlphaV+Thy-CD105-6C3-], which includes both the CD200+/– cell populations, and thus illustrates the transcriptional expression data of the mSSC/pre-BCSP. FIG. 15J(ii) Single cell RNA sequencing of the following cell populations: 6C3(+) (encompassing the 6C3 and HEC subpopulations), Thy (+) (encompassing the CCP, Thy and BLSP subpopulations), mSSC and BCSP. The graph illustrates the expression of Sox9.

FIG. 16A A 17-week-old human fetal femur cross section stained with Movat's Pentachrome showing cartilage (blue), and bone (yellow) regions. Inset picture shows growth plate region where we find high SSC frequency. FIG. 16B Experimental scheme for prospective isolation of human skeletal stem/progenitor cells and secondary phenotypic characterization in vivo. FIG. 16C FACS gating strategy of human skeletal stem/progenitor subsets from 17-week human fetal femur, indicating defined populations that give rise to cartilage, bone with cartilage, or bone with marrow. Colored arrows indicate Pentachrome stained sections of explanted human progenitor-derived tissues in kidney (blue=cartilage; green=bone+cartilage; yellow=bone). FIG. 16D Diagram indicating femoral head region and picture of adult femoral head region where human skeletal stem/progenitor subsets can be isolated. FIG. 16E FACS gating strategy of human skeletal stem/progenitor subsets isolated from adult femoral head tissue.

FIG. 17A-17E. FIG. 17A Scheme for in vitro analysis of lineage progression by hSSC and human skeletal progenitor subsets. FIG. 17B (Top and middle panels) Differentiation of cultured hSSC into lineage restricted subsets as assayed by FACS. (Bottom panel) Differing osteogenic capacity of individual human skeletal progenitor subsets as determined by alizarin red staining (hSSC=human skeletal stem cell; BCSP=bone, cartilage and stromal progenitor cell; hCP=human-chondrogenic progenitor; hOP=human osteogenic progenitor). The strongest Alizarin Red is shown in hOP. FIG. 17C Experimental scheme of RGB viral labeling and in vivo clonal expansion of lentivirally-labeled human skeletal stem cell (hSSC) FIG. 17D Clones of lentivirally-labeled EGFP and RFP hSSC differentiate into bone (yellow) and cartilage (blue) in vivo as shown in Pentachrome stained sections of hSSC derived kidney grafts. FIG. 17E (Upper panel) Micrograph of the colonies derived from cultures of hSSC, BCSP, hOP, and hCP, respectively. (Bottom panel) FACS plots of four human skeletal stem/progenitor subsets.

FIG. 19A-19F. FIG. 19A (Left panel) Diagram showing localization of human skeletal progenitors subsets in developing bones alongside (right panel) diagram depicting range of skeletal niche factors (hSSC=human skeletal stem cell; BCSP=bone, cartilage and stromal progenitor cell; hCP=human chondrogenic progenitor; hOP=human osteogenic progenitor). FIG. 19B Diagram of hSSC niche interactions. FIG. 19 ChSSC expansion from treatment with representative mSSC niche factor. FIG. 19D Prediction of niche factor/cognate receptor interactions among human skeletal populations by GEXC algorithm. FIG. 19E Normalized expression of representative SSC niche factors BMP2, VEGF, WNT1, WNT3 in human skeletal progenitors subsets. FIG. 19F (Left panel) Heat maps of four human skeletal progenitors from single-cell mRNA seq. (Right panels) Venn diagram illustrating co-expression of BMP2 or WNT ligands and receptors at single cell level.

FIG. 20A-20E. FIG. 20A (Top FACS plots) hASCs show expression of BMPR1B indicating responsiveness to BMP signaling. (Bottom FACS plots) Induction of hSSC formation from hASC by BMP2. FIG. 20B Scheme for co-delivery of hASCs with reprogramming BMP2. FIG. 20C (Left panels) Gross photo of subcutaneously induced ossicle derived from co-delivery of hASCs with BMP2. The bottom panel illustrates 3× magnified images of the rectangle in the upper panel. (Right panels) Micrograph of induced ossicle section stained with Movat's Pentachrome (bone=yellow; cartilage=greenish blue). FIG. 20D Diagram of in situ induction of bone, or cartilage formation from mouse adipose tissue using combinations of BMP2 and soluble VEGF receptor. FIG. 20E VEGF signaling can switch BMP2 induced mSSC towards bone (left) or cartilage fates (right).

DETAILED DESCRIPTION OF THE EMBODIMENTS OF THE INVENTION

Figure 2G:
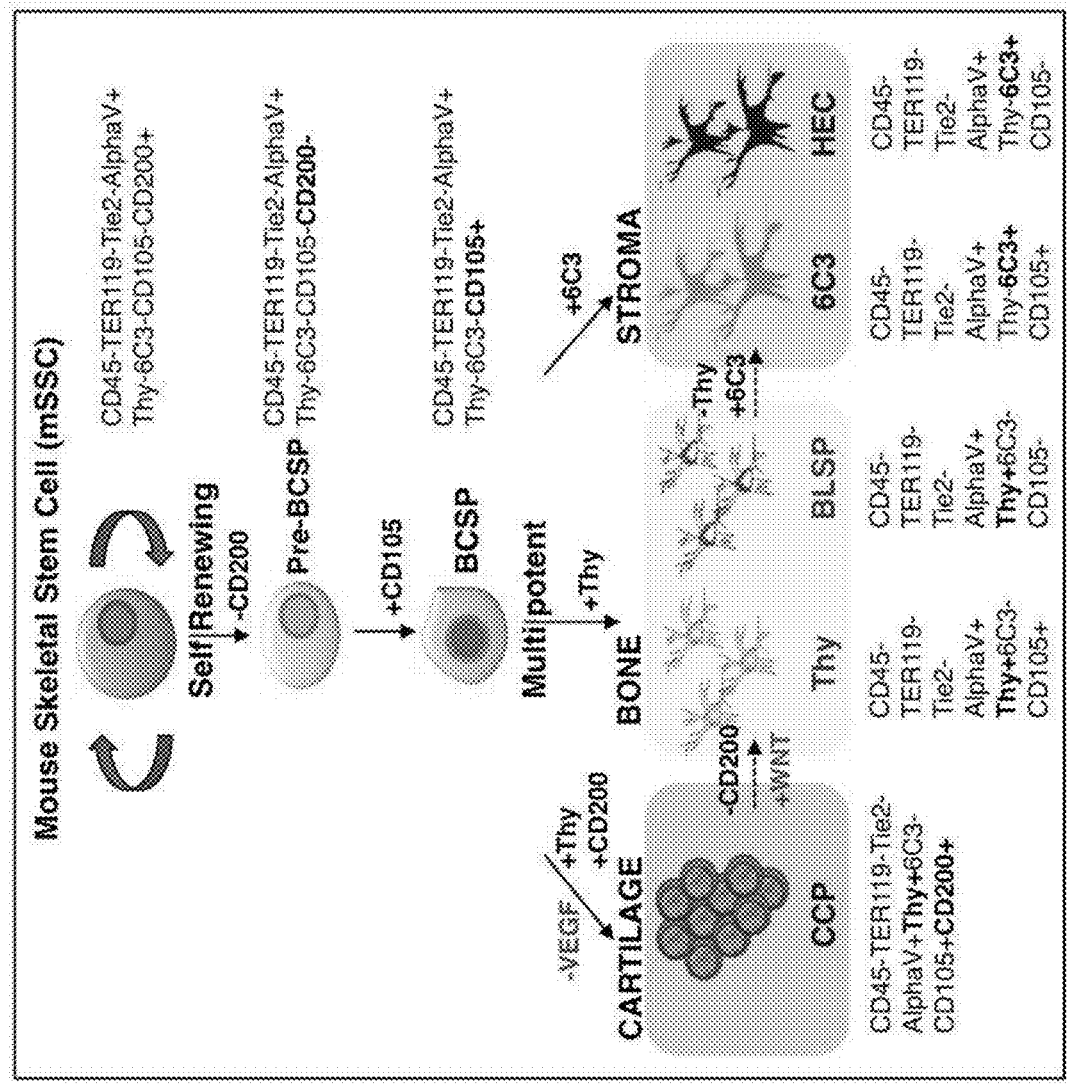

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Methods, compositions and kits for producing functional chondrocytes, skeletal cells, bone marrow stromal cells, and progenitor cells thereof are provided. These methods, compositions and kits find use in producing chondrocytes, osteoblasts, stromal cells, and progenitor cells thereof for transplantation, for experimental evaluation, as a source of lineage- and cell-specific products, and the like, for example for use in treating human disorders of the cartilage, bone and hematopoietic system. Also provided are methods, compositions and kits for screening candidate agents for activity in converting cells into skeletal cells, astrocytes, oligodendrocytes, and progenitor cells thereof.

In some embodiments, compositions and methods are provided for directing differentiation of mammalian of skeletal stem cells, including differentiation into osteogenic, chondrogenic, and stromal lineages. In some embodiments, compositions and methods are provided for directing differentiation of non-skeletal cells, for example pluripotent stem cells, mesenchymal stem cells (MSC), etc., into skeletal stem cells. For in vivo uses, reprogramming factor(s) can be provided systemically or as a localized implant, and are optionally provided with an effective dose of cells, e.g. SSC, MSC, committed cartilage progenitor cells (CCP), and the like. Cell culture systems for such methods are also provided. The cells find use in therapeutic methods, e.g. to provide cells for skeletal or chondrogenic replacement therapy; in screening methods, and the like. In some embodiments, the cells are mammalian cells. In some embodiments, the cells are human or mouse cells.

These and other objects, advantages, and features of the invention will become apparent to those persons skilled in the art upon reading the details of the subject methods and compositions as more fully described below.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

By "proliferate" it is meant to divide by mitosis, i.e. undergo mitosis. An "expanded population" is a population of cells that has proliferated, i.e. undergone mitosis, such that the expanded population has an increase in cell number, that is, a greater number of cells, than the population at the outset.

The term "explant" refers to a portion of an organ or tissue therein taken from the body and cultured in an artificial medium. Cells that are grown "ex vivo" are cells that are taken from the body in this manner, temporarily cultured in vitro, and returned to the body.

The term "primary culture" denotes a mixed cell population of cells from an organ or tissue within an organ. The word "primary" takes its usual meaning in the art of tissue culture.

The term "tissue" refers to a group or layer of similarly specialized cells which together perform certain special functions.

The term "organ" refers to two or more adjacent layers of tissue, which layers of tissue maintain some form of cell-cell and/or cell-matrix interaction to form a microarchitecture.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning. The methods of the invention also include the use of factor combinations that consist, or consist essentially of the desired factors.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

Cartilage is a hyperhydrated structure with water comprising 70% to 80% of its weight. The remaining 20% to 30% comprises type II collagen and proteoglycan. Collagen usually accounts for 70% of the dry weight of cartilage. Proteoglycans are composed of a central protein core from which long chains of polysaccharides extend. These polysaccharides, called glycosaminoglycans, include: chondroitin-4-sulfate, chondroitin-6-sulfate, and keratan sulfate. Cartilage has a characteristic structural organization consisting of chondrogenic cells dispersed within an endogenously produced and secreted extracellular matrix. The cavities in the matrix which contain the chondrocytes are called cartilage lacunae. Unlike bone, cartilage is neither innervated nor penetrated by either the vascular or lymphatic systems.

Three types of cartilage are present in mammals and include: hyaline cartilage; fibrocartilage and elastic cartilage. Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the annulus fibrosis of the invertebral disc, tendinous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage prevents direct contact of the opposing bone surfaces and permits the near frictionless movement of the articulating bones relative to one another. Two types of articular cartilage defects are commonly observed in mammals and include full-thickness and partial-thickness defects. The two-types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

The term "skeletal stem cell" refers to a multipotent and self-renewing cell capable of generating bone marrow stromal cells, skeletal cells, and chondrogenic cells. By self-renewing, it is meant that when they undergo mitosis, they produce at least one daughter cell that is a skeletal stem cell. By multipotent it is meant that it is capable of giving rise to progenitor cell (skeletal progenitors) that give rise to all cell types of the skeletal system. They are not pluripotent, that is, they are not capable of giving rise to cells of other organs in vivo.

Skeletal stem cells are also reprogrammed from non-skeletal cells, including without limitation mesenchymal stem cells, and adipose tissue containing such cells. Reprogrammed cells may be referred to as induced skeletal stem cells, or iSSC. "iSSC" arise from a non-skeletal cell by experimental manipulation. Induced skeletal cells have characteristics of functional SSCs derived from nature, that is, they can give rise to the same lineages.

Human SSC cell populations are negative for expression of CD45, CD235, Tie2, and CD31; and positively express podoplanin (PDPN). A population of cells, e.g. cells isolated from bone tissue, having this combination of markers may be referred to as [PDPN$^+$/146$^-$] cells. The [PDPN$^+$/146$^-$] population can be further subdivided into three populations: a unipotent subset capable of chondrogenesis [PDPN$^+$CD146$^-$CD73$^-$CD164$^+$], a unipotent cellular subpopulation capable of osteogenesis [PDPN$^+$CD146$^-$CD73$^-$CD164$^+$] and a multipotent [PDPN$^+$CD146$^-$CD73$^+$CD164$^+$] cell capable of endochondral (bone and cartilage) ossification. A population of cells of interest for use in the methods of the invention may be isolated from bone with respect to CD45, CD235, Tie2, and CD31 and PDPN. Other cell populations of interest are [PDPN$^+$CD146$^-$CD73$^-$CD164$^-$] cells; [PDPN$^+$CD146$^-$CD73$^-$CD164$^+$] cells; and [PDPN$^+$CD146$^-$CD73$^+$CD164$^+$] cells.

The mouse skeletal lineage is characterized as CD45-, Ter119-, Tie2-, αv integrin+. The SSC is further characterized as Thy1-6C3-CD105-CD200+.

Adipose-Derived Stem Cells. Adipose-derived stem cells or "adipose-derived stromal cells" refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may be provided as a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention.

Adipose tissue offers many practical advantages for tissue engineering applications. It is abundant and accessible to harvest methods with minimal risk to the patient. It is estimated that there are more than 10.sup.4 stem cells per gram of adipose tissue (Sen et al 2001, Journal of Cellular Biochemistry 81:312-319), which cells can be used immediately or cryopreserved for future autologous or allogeneic applications.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells may be obtained from minced human adipose tissue by collagenase digestion and differential centrifugation [Halvorsen et al 2001, Metabolism 50:407-413; Hauner et al 1989, J Clin Invest 84:1663-1670; Rodbell et al 1966. J Biol Chem 241:130-139].

Adipose tissue derived stem cells have been reported to express markers including: CD13, CD29, CD44, CD63, CD73, CD90, CD166, aldehyde dehydrogenase (ALDH), and ABCG2. The adipose tissue derived stem cells may be a population of purified mononuclear cells extracted from adipose tissue capable of proliferating in culture for more than 1 month.

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The cell population may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The adipose cells may be cultured in vitro under various culture conditions. Culture medium may be liquid or semisolid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. In one embodiment of the invention, the adipose cells are maintained in culture in the absence of feeder layer cells, i.e. in the absence of serum, etc. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The terms "efficiency of reprogramming", "reprogramming efficiency", "efficiency of conversion", or "conversion efficiency" are used interchangeably herein to refer to the ability of cells of one cell lineage to give rise to an induced cell of another cell lineage when contacted with the appropriate reprogramming system, for example, the ability of adipose tissue cells to give rise to iSSC when contacted with high doses of BMP2. In other words, the cells produce about 1.5-fold, about 2-fold, about 3-fold, about 4-fold, about 6-fold, about 8-fold, about 10-fold, about 20-fold, about 30-fold, about 50-fold, about 100-fold, about 200-fold the number of induced cells (e.g. iSSC) as the uncontacted population, or more.

In addition to reprogramming, cells may be directed to differentiate along a specific path. For example, in the absence of intervention SSC in vivo give rise to very few chondrocytes, but can be directed to chondrogenesis by differentiation factors, which may be referred to herein as chondrogenesis factors.

As used herein, the term "BMP-2" refers to the family of bone morphogenetic proteins of the type 2, derived from any species, and may include mimetics and variants thereof. Reference to BMP-2 herein is understood to be a reference to any one of the currently identified forms, including BMP-2A and BMP-2B, as well as to BMP-2 species identified in the future. The term "BMP-2" also includes polypeptides derived from the sequence of any known BMP-2 whose mature sequence is at least about 75% homologous with the sequence of a mature human BMP-, which reference sequence may be found in Genbank, accession number NP_001191.

BMP-2 signals via two types of receptors (BRI and BRII) that are expressed at the cell surface as homomeric as well as heteromeric complexes. Prior to ligand binding, a low but measurable level of BMP-receptors is found in preformed hetero-oligomeric complexes. The major fraction of the receptors is recruited into hetero-oligomeric complexes only after ligand addition. For this, BMP-2 binds first to the high affinity receptor BRI and then recruits BRII into the signaling complex. However, ligand binding to the preformed complex composed of BRII and BRI is still required for signaling, suggesting that it may mediate activating conformational changes. Signals induced by binding of BMP-2 to preformed receptor complexes activate the Smad pathway, whereas BMP-2-induced recruitment of receptors activates a different, Smad-independent pathway resulting in the induction of alkaline phosphatase activity via p38 MAPK.

In some embodiments, a dose of BMP2 is provided in an implant, e.g. a matrix or scaffold for localized delivery of the factor, where the BMP2 is provided as a BMP2 protein or active fragment thereof. The effective dose may be determined based on the specific tissue, rate of release from the implant, size of the implant, and the like. and may be empirically determined by one of skill in the art. The dose may provide for biological activity equivalent to 1 µg BMP2 protein, 10 µg, 100 µg, 1 mg, 5 mg, 10 mg, 25 mg, 50 mg, 75 mg, 100 mg, 250 mg, 500 mg, 750 mg, 1 g of BMP2 protein. The dose may be administered at a single time point, e.g. as a single implant; or may be fractionated, e.g. delivered in a microneedle configuration. The dose may be administered, once, two, three time, 4 times, 5 times, 10 times, or mare as required to achieve the desired effect, and administration may be daily, every 2 days, every 3 days, every 4 days, weekly, bi-weekly, monthly, or more.

"BMP2 mimetics" include molecules that function similarly to BMP2 by binding and activating its receptors as described above. Molecules useful as BMP2 mimetics include derivatives, variants, and biologically active fragments of naturally occurring BMP2. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural BMP2 protein.

Fragments of the soluble BMP2, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to BMP2. A fragment "at least 20 aa in length," for example, is intended to include 20 or more contiguous amino acids from, for example, the polypeptide encoded by a cDNA for BMP2. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods.

A "fusion" polypeptide is a polypeptide comprising a polypeptide or portion (e.g., one or more domains) thereof fused or bonded to heterologous polypeptide. A fusion BMP2 protein, for example, will share at least one biological property in common with a native BMP2 polypeptide. Examples of fusion polypeptides include immunoadhesins, as described above, which combine a portion of the BMP2 polypeptide with an immunoglobulin sequence, and epitope tagged polypeptides, which comprise a BMP2 polypeptide or portion thereof fused to a "tag polypeptide". The tag polypeptide has enough residues to provide an epitope against which an antibody can be made, yet is short enough such that it does not interfere with biological activity of the BMP2 polypeptide. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. Derivatives and fusion of soluble BMP2 find use as BMP2 mimetic molecules.

Stable plasma proteins are proteins typically having about from 30 to 2,000 residues, which exhibit in their native environment an extended half-life in the circulation, i.e. greater than about 20 hours. Examples of suitable stable plasma proteins are immunoglobulins, albumin, lipoproteins, apolipoproteins and transferrin. The extracellular region of BMP2 is typically fused to the plasma protein at the N-terminus of the plasma protein or fragment thereof which is capable of conferring an extended half-life upon the soluble BMP2. Increases of greater than about 100% on the plasma half-life of the soluble BMP2 are satisfactory.

Suitable BMP2 mimetics and/or fusion proteins may be identified by compound screening by detecting the ability of an agent to mimic the biological activity of BMP2, for example in increasing the number of skeletal stem cells in a population on non-skeletal cells, e.g. by at least 10%, 20%, 30%, 405, 50%, 60%, 70%, 80%, 90%, 2-fold, 3-fold, 4-fold, 5-fold, 10-fold, 100-fold or more.

VEGF is a dimeric, disulfide-linked 46-kDa glycoprotein related to Platelet-Derived Growth Factor ("PDGF"). It is produced by normal cell lines and tumor cell lines; is an endothelial cell-selective mitogen; shows angiogenic activity in in vivo test systems (e.g., rabbit cornea); is chemotactic for endothelial cells and monocytes; and induces plasminogen activators in endothelial cells, which are involved in the proteolytic degradation of the extracellular matrix during the formation of capillaries. A number of isoforms of VEGF are known, which while they show comparable biological activity, differ in the type of cells that secrete them and in their heparin-binding capacity. In addition, there are other members of the VEGF family, such as Placenta Growth Factor ("PGF") and VEGF-C.

The cellular receptors of VEGFs (VEGFRs) are transmembranous receptor tyrosine kinases. They are characterized by an extracellular domain with seven immunoglobulin-like domains and an intracellular tyrosine kinase domain. Various types of VEGF receptor have been characterized, including VEGFR-1 (also known as flt-1), VEGFR-2 (also known as KDR), and VEGFR-3.

"VEGF inhibitor" as used herein is any substance that decreases signaling by the VEGF-VEGFR pathway. VEGF inhibitors can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signaling pathway. Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what it would be in the same circumstance in the absence of the inhibitor.

In some embodiments, a dose of VEGF inhibitor is provided in an implant, e.g. a matrix or scaffold for localized delivery of the facto. The effective dose may be determined based on the specific tissue, rate of release from the implant, size of the implant, and the like. and may be empirically determined by one of skill in the art. The dose may provide for biological activity equivalent to 1 μg soluble VEGF receptor, 10 μg, 100 μg, 1 mg, 5 mg, 10 mg, 25 mg, 50 mg, 75 mg, 100 mg, 250 mg, 500 mg, 750 mg, 1 g of soluble VEGF receptor. The dose may be administered at a single time point, e.g. as a single implant; or may be fractionated, e.g. delivered in a microneedle configuration. The dose may be administered, once, two, three time, 4 times, 5 times, 10 times, or mare as required to achieve the desired effect, and administration may be daily, every 2 days, every 3 days, every 4 days, weekly, bi-weekly, monthly, or more.

A great many VEGF inhibitors have been described in the literature. In addition to those described in further detail below, VEGF inhibitors are described in the following patent documents: US 2003/0105091, US2006/0241115, U.S. Pat. Nos. 5,521,184, 5,770,599, 5,990,141, 6,235,764, 6,258,812, 6,515,004, 6,630,500, 6,713,485, WO2005/070891, WO 01/32651, WO 02/68406, WO 02/66470, WO 02/55501, WO 04/05279, WO 04/07481, WO 04/07458, WO 04/09784, WO 02/59110, WO 99/450029, WO 00/59509, WO 99/61422, WO 00/12089, WO 00/02871, and WO 01/37820, particularly in parts pertinent to VEGF inhibitors.

The following are among specific VEGF inhibitors: ABT-869 (Abbott) including formulations for oral administration and closely related VEGF inhibitors; AEE-788 (Novartis) (also called AE-788 and NVP-AEE-788, among others) including formulations for oral administration and closely related VEGF inhibitors; AG-13736 (Pfizer) (also called AG-013736) including formulations for oral administration and closely related VEGF inhibitors; AG-028262 (Pfizer) and closely related VEGF inhibitors; Angiostatin (EntreMed) (also called CAS Registry Number 86090-08-6, K1-4, and rhuAngiostatin, among others) and closely related inhibitors as described in, among others, U.S. Pat. Nos. 5,792,825 and 6,025,688, particularly in parts pertaining to Angiostatin and closely related VEGF inhibitors, their structures and properties, and methods for making and using them; Avastin™ (Genentech) (also called bevacizumab, R-435, rhuMAB-VEGF, and CAS Registry Number 216974-75-3, among others) and closely related VEGF inhibitors; AVE-8062 (Ajinomoto Co. and Sanofi-aventis) (also called AC-7700 and combretastatin A4 analog, among others), and closely related VEGF inhibitors; AZD-2171 (AstraZeneca) and closely related VEGF inhibitors; Nexavar® (Bayer AG and Onyx) (also called CAS Registry Number 284461-73-0, BAY-43-9006, raf kinase inhibitor, sorafenib, sorafenib analogs, and IDDBCP150446, among others) and closely related VEGF inhibitors; BMS-387032 (Sunesis and Bristol-Myers Squibb) (also called SNS-032 and CAS Registry Number 345627-80-7, among others) and closely related VEGF inhibitors; CEP-7055 (Cephalon and Sanofi-aventis) (also called CEP-11981 and SSR-106462, among others) and closely related VEGF inhibitors; CHIR-258 (Chiron) (also called CAS Registry Number 405169-16-6, GFKI, and GFKI-258, among others) and closely related VEGF inhibitors; CP-547632 (OSI Pharmaceuticals and Pfizer) (also called CAS Registry Number 252003-65-9, among others) and closely related VEGF inhibitors such as, for instance, CP-564959; E-7080 (Eisai Co.) (also called CAS Registry Number 417716-92-8 and ER-203492-00, among others) and closely related VEGF inhibitors; 786034 (GlaxoSmithKline) and closely related VEGF inhibitors; GW-654652 (GlaxoSmithKline) and closely related indazolylpyrimidine Kdr inhibitors; IMC-1C11 (ImClone) (also called DC-101 and c-p1C11, among others) and closely related VEGF inhibitors; KRN-951 (Kirin Brewery Co.) and other closely related quinoline-urea VEGF inhibitors; PKC-412 (Novartis) (also called CAS Registry Number 120685-11-2, benzoylstaurosporine, CGP-41251, midostaurin, and STI-412, among others) and closely related VEGF inhibitors; PTK-787 (Novartis and Schering) (also called CAS Registry Numbers 212141-54-3 and 212142-18-2, PTK/ZK, PTK-787/ZK-222584, ZK-22584, VEGF-TKI, VEGF-RKI, PTK-787A, DE-00268, CGP-79787, CGP-79787D, vatalanib, ZK-222584, among others) and closely related anilinophthalazine derivative VEGF inhibitors; SU11248 (Sugen and Pfizer) (also called SU-11248, SU-011248, SU-11248J, Sutent®, and sunitinib malate, among others) and closely related VEGF inhibitors; SU-5416 (Sugen and Pfizer/Pharmacia) (also called CAS Registry Number 194413-58-6, semaxanib, 204005-46-9, among others) and closely related VEGF inhibitors; SU-6668 (Sugen and Taiho) (also called CAS Registry Number 252916-29-3, SU-006668, and TSU-68, among others) and closely related VEGF inhibitors as described in, among others, WO-09948868, WO-09961422, and WO-00038519, particularly in parts pertaining to SU-6668 and closely related VEGF inhibitors, their structures and properties, and methods for making and using them; VEGF Trap (Regeneron and Sanofi-aventis) (also called AVE-0005 and Systemic VEGF Trap, among others) and closely related VEGF inhibitors as described in, among others, WO-2004110490, particularly in parts pertaining to VEGF Trap and closely related VEGF inhibitors, their structures and properties, and methods for making and using them; Thalidomide (Celgene) (also called CAS Registry Number 50-35-1, Synovir, Thalidomide Pharmion, and Thalomid, among others) and closely related VEGF inhibitors; XL-647 (Exelixis) (also called EXEL-7647, among others) and closely related VEGF inhibitors; XL-999 (Exelixis) (also called EXEL-0999, among others) and closely related VEGF inhibitors; XL-880 (Exelixis) (also called EXEL-2880, among others) and closely related VEGF inhibitors; ZD-6474 (AstraZeneca) (also called CAS Registry Number 443913-73-3, Zactima, and AZD-6474, among others) and closely related anilinoquinazoline VEGF inhibitors; and ZK-304709 (Schering) (also called CDK inhibitors (indirubin derivatives), ZK-CDK, MTGI, and multi-target tumor growth inhibitor, among others) and other closely related compounds including the indirubin derivative VEGF inhibitors described in WO-00234717, WO-02074742, WO-02100401, WO-00244148, WO-02096888, WO-03029223, WO-02092079, and WO-02094814, particularly in parts pertinent to these and closely related VEGF inhibitors, their structures and properties, and methods for making and using them.

VEGF inhibitors may be delivered in a manner appropriate to the nature of the inhibitor, e.g. as a protein, small molecule, nucleic acid, etc., including without limitation appropriate vehicles and vectors as required.

Transforming growth factor-beta (TGF-β) denotes a family of proteins, TGF-β1, TGF-β2, and TGF-β3, which are pleiotropic modulators of cell growth and differentiation, embryonic and bone development, extracellular matrix formation, hematopoiesis, immune and inflammatory responses (Roberts and Sporn *Handbook of Experimental Pharmacology* (1990) 95:419-58; Massague et al. *Ann Rev Cell Biol* (1990) 6:597-646). TGF-13 initiates intracellular signaling pathways leading ultimately to the expression of genes that regulate the cell cycle, control proliferative responses, or relate to extracellular matrix proteins that mediate outside-in cell signaling, cell adhesion, migration and intercellular communication.

TGF-β exerts its biological activities through a receptor system including the type I and type II single transmembrane TGF-13 receptors (also referred to as receptor subunits) with intracellular serine-threonine kinase domains, that signal through the Smad family of transcriptional regulators. Binding of TGF-β to the extracellular domain of the type II receptor induces phosphorylation and activation of the type I receptor (TGFβ-R1) by the type II receptor (TGFβ-R2).

A TGFβ inhibitor refers to a molecule, e.g. a decoy receptor, antibody or derivative thereof, a nonpeptide small molecule, etc. specifically binding to a TGFβ-R1 receptor having the ability to inhibit the biological function of a native TGF-13 molecule.

Wnt proteins form a family of highly conserved secreted signaling molecules that regulate cell-to-cell interactions during embryogenesis. The terms "Wnts" or "Wnt gene product" or "Wnt protein" or "Wnt polypeptide" are used interchangeable and encompass native sequence Wnt polypeptides, Wnt polypeptide variants, Wnt polypeptide fragments and chimeric Wnt polypeptides. These polypeptides are wnt agonists, which term also include small molecule, mimetics, e.g. peptidomimetics, agonist antibodies, and proteins that agonize wnt function, as known in the art. A "native sequence" polypeptide is one that has the same amino acid sequence as a Wnt polypeptide derived from nature, regardless of the method used for its production. Such native sequence polypeptides can be isolated from cells producing endogenous Wnt protein or can be produced by recombinant or synthetic means. Thus, a native sequence polypeptide can have the amino acid sequence of, e.g.

naturally occurring human polypeptide, murine polypeptide, or polypeptide from any other mammalian species, or from non-mammalian species, e.g. *Drosophila, C. elegans*, and the like.

Suitable Wnt polypeptides (i.e., Wnt proteins) include, but are in no way limited to human Wnt polypeptides. Human Wnt proteins of interest in the present application include the following (accession numbers are for mRNAs encoding the associated Wnt protein): Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-10A (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15). Other Wnt polypeptides of interest in the present invention include orthologs of the above from any mammal, including domestic and farm animals, and zoo, laboratory or pet animals, dogs, cats, cattle, horses, sheep, pigs, goats, rabbits, rats, mice, frogs, zebra fish, fruit fly, worm, etc.

The term "native sequence Wnt polypeptide" includes, without limitation, human and murine Wnt polypeptides. Human Wnt proteins include the following: Wnt1, Genbank reference NP005421.1; Wnt2, Genbank reference NP003382.1, which is expressed in brain in the thalamus, in fetal and adult lung and in placenta; two isoforms of Wnt2B, Genbank references NP004176.2 and NP078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP11 0380.1 and X56842 (Swiss-Prot P56704), respectively.

The native human Wnt3A amino acid sequence has Genbank reference NP_149122.1. Wnt 4 has the Genbank reference NP11 0388.2. Wnt 5A and Wnt 5B have the Genbank references NP003383.1 and AK013218. Wnt 6 has the Genbank reference NP006513.1; Wnt 7A has the Genbank reference NP004616.2. Wnt 7B has the Genbank reference NP478679.1. Wnt 8A has two alternative transcripts, Genbank references NP114139.1 and NP490645.1. Wnt 8B has the Genbank reference NP003384.1. Wnt 10A has the Genbank reference NP079492.2. Wnt 10B has the Genbank reference NP003385.2. Wnt 11 has the Genbank reference NP004617 .2. Wnt 14 has the Genbank reference NP003386.1. Wnt 15 has the Genbank reference NP003387.1. Wnt 16 has two isoforms, Wnt-16a and Wnt-16b, produced by alternative splicing, Genbank references are NP057171.2 and NP476509.1. All GenBank, SwissProt and other database sequences listed are expressly incorporated by reference herein.

The effective dose of the Wnt protein may vary depending on the source, purity, preparation method, etc. For the purposes of the present invention, Wnt proteins of interest include human Wnt3 and Wnt5 proteins for the enhancement of osteogenesis by skeletal stem cells. Where the Wnt protein is Wnt3, Wnt3A, Wnt5A, Wnt5B, e.g. the human counterpart of these proteins, the effective dose is usually at least 0.1 µg/ml, at least 0.5 µg/ml, at least 1 µg/ml, at least 2.5 µg/ml, at least 5 µg/ml, at least 7.5 µg/ml, at least 10 µg/ml, at least 15 µg/ml, and may be at least 25 µg/ml, at least 50 µg/ml, or at least 100 µg/ml.

A Wnt agonist is any molecule (e.g., a chemical compound; a non-coding nucleic acid, e.g., a non-coding RNA; a polypeptide; a nucleic acid encoding a polypeptide, etc.) that results in increased output (i.e., increased target gene expression) from the Wnt signaling pathway. For example, a Wnt agonist can function by stabilizing, enhancing the expression of, or enhancing the function of a positive regulatory component of the pathway or by destabilizing, decreasing the expression of, or inhibiting the function of a negative regulatory component of the pathway. Thus, a Wnt agonist can be a positive regulatory component of the pathway (e.g., a Wnt protein), or a nucleic acid encoding one or more positive regulatory components of the pathway. A Wnt agonist can also be a small molecule or nucleic acid that stabilizes a positive regulatory component of the pathway either at the level of mRNA or protein.

In some embodiments, a Wnt agonist functions by stabilizing β-Catenin, thus allowing nuclear levels of β-Catenin to rise. β-Catenin can be stabilized in multiple different ways. As multiple different negative regulatory components of the Wnt signaling pathway function by facilitating the degradation of β-Catenin, a Wnt agonist can be a small molecule or nucleic acid inhibitor (e.g., microRNA, shRNA, etc.)(functioning at the level of mRNA or protein) of a negative regulatory component of the pathway. For example, in some embodiments, the Wnt agonist is an inhibitor of GSK-3β. In some such embodiments, the inhibitor of GSK-3β is a small molecule chemical compound (e.g., TWS119, BIO, CHIR-99021, SB 216763, SB 415286, CHIR-98014 and the like).

TWS119: 3-(6-(3-aminophenyl)-7H-pyrrolo[2,3-d]pyrimidin-4-yloxy)phenol is described by Ding et. al, Proc Natl Acad Sci USA. 2003 Jun. 24; 100(13):7632-7. BIO: 6-bromo-3-[(3E)-1,3-dihydro-3-(hydroxyimino)-2H-indol-2-ylidene]-1,3-dihydro-(3Z)-2H-indol-2-one or (2'Z,3'E)-6-Bromoindirubin-3'-oxime is described by Meijer et. al, Chem Biol. 2003 December; 10(12):1255-66. CHIR-99021: 6-[[2-[[4-(2,4-dichlorophenyl)-5-(5-methyl-1H-imidazol-2-yl)-2-pyrimidinyl]amino]ethyl]amino]-3-pyridinecarbonitrile is described by Bennett et al., J Biol Chem. 2002 Aug. 23; 277(34):30998-1004. SB 216763: 3-(2,4-dichlorophenyl)-4-(1-methyl-1H-indol-3-yl)-1H-pyrrole-2,5-dione is described by Cross et al., J Neurochem. 2001 April; 77(1): 94-102. SB 415286: 3-(3-chloro-4-hydroxyphenylamino)-4-(2-nitrophenyl)-1H-pyrrole-2,5-dione is described by Cross et al., J Neurochem. 2001 April; 77(1):94-102. CHIR-98014: N2-(2-(4-(2,4-dichlorophenyl)-5-(1H-imidazol-1-yl) pyrimidin-2-ylamino)ethyl)-5 nitropyridine-2,6-diamine is described by Ring et al., Diabetes. 2003 March; 52(3):588-95. Each reference is herein specifically incorporated by reference.

The effective dose of a Wnt agonist can be at least 0.1 µM, at least 1 µM, at least 2.5 µM, at least 5 µM, and usually not more than 500 µM, not more than 250 µM, not more than 100 µM, or not more than 50 µM.

Tissue engineering is the use of a combination of cells, engineering and materials methods, and suitable biochemical and physico-chemical factors to improve or replace biological functions. Cells may be implanted or 'seeded' into an artificial structure capable of supporting three-dimensional tissue formation. These structures, referred to herein as a matrix or scaffold, allow cell attachment and migration, deliver and retain cells and biochemical factors, enable diffusion of vital cell nutrients and expressed products. A high porosity and an adequate pore size are necessary to facilitate cell seeding and diffusion throughout the whole structure of both cells and nutrients. Biodegradability is often a factor since scaffolds may be absorbed by the surrounding tissues without the necessity of a surgical removal. The rate at which degradation occurs has to coincide as much as possible with the rate of tissue formation: this means that while cells are fabricating their own natural matrix structure around themselves, the scaffold is able to provide structural integrity within the body and eventually it will break down leaving the neotissue, newly formed tissue which will take over the mechanical load. Injectability is also important for clinical uses.

Many different materials (natural and synthetic, biodegradable and permanent) have been investigated, e.g. Puramatrix, polylactic acid (PLA), polyglycolic acid (PGA) and polycaprolactone (PCL), and combinations thereof. Scaffolds may also be constructed from natural materials, e.g. proteins such as collagen, fibrin, etc; polysaccharidic materials, such as chitosan; alginate, glycosaminoglycans (GAGs) such as hyaluronic acid, etc. Functionalized groups of scaffolds may be useful in the delivery of small molecules (drugs) to specific tissues. Another form of scaffold under investigation is decellularised tissue extracts whereby the remaining cellular remnants/extracellular matrices act as the scaffold.

A system for pharmaceutical use, i.e. a scaffold or implant with cells and/or factors, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the NR pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical composition, i.e. combinations of factors and/or cells, can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxin, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g. murine, lagomorpha, etc. may be used for experimental investigations.

More particularly, the present invention finds use in the treatment of subjects, such as human patients, in need of bone or cartilage replacement therapy. Examples of such subjects would be subjects suffering from conditions associated with the loss of cartilage from osteoarthritis, genetic defects, disease, etc. Patients having diseases and disorders characterized by such conditions will benefit greatly by a treatment protocol of the pending claimed invention.

An effective amount of a pharmaceutical composition of the invention is the amount that will result in an increase the number of chondrocytes, skeletal cells, cartilage or bone mass at the site of implant, and/or will result in measurable reduction in the rate of disease progression in vivo. For example, an effective amount of a pharmaceutical composition will increase bone or cartilage mass by at least about 5%, at least about 10%, at least about 20%, preferably from about 20% to about 50%, and even more preferably, by greater than 50% (e.g., from about 50% to about 100%) as compared to the appropriate control, the control typically being a subject not treated with the composition.

The methods of the present invention also find use in combined therapies, e.g. in with therapies that are already known in the art to provide relief from symptoms associated with the aforementioned diseases, disorders and conditions. The combined use of a pharmaceutical composition of the present invention and these other agents may have the advantages that the required dosages for the individual drugs is lower, and the effect of the different drugs complementary.

In some embodiments an effective dose of adipose stromal cells, preferably adipose derived stem cells, are provided in an implant or scaffold for the regeneration of skeletal or cartilaginous tissue. An effective cell dose may depend on the purity of the population. In some embodiments an effective dose delivers a dose of adipose derived stem cells of at least about $10^2$, about $10^3$, about $10^4$, about $10^5$, about $10^6$, about $10^7$, about $10^8$, about $10^9$ or more cells, which stem cells may be present in the cell population at a concentration of about 1%, about 5%, about 10%, about 20%, about 30%, about 40%, about 50%, about 60%, about 70%, about 80%, about 90% or more.

The present invention provides methods and a composition for the differentiation of non-skeletal cells, including adipose tissue derived stromal cells, into chondrocytes. The cells produced by the methods of invention are useful in providing a source of fully differentiated and functional cells for research, transplantation, and development of tissue engineering products for the treatment of human disease and traumatic injury repair.

"Chondrocytes (cartilage cells)" refers to cells that are capable of expressing characteristic biochemical markers of chondrocytes, including but not limited to collagen type II, chondroitin sulfate, keratin sulfate and characteristic morphologic markers of smooth muscle, including but not limited to the rounded morphology observed in culture, and able to secrete collagen type II, including but not limited to the generation of tissue or matrices with hemodynamic properties of cartilage in vitro.

Methods of the Invention

The subject invention is directed, in part, to methods of reprogramming and directing differentiation of a cell to a desired skeletal lineage cell. Specific embodiments include the skewing of differentiation from a skeletal stem cell to a chondrocyte; and the reprogramming of an adipose tissue cell, including without limitation an adipose tissue stromal cell, or an adipose tissue derived stem cell, into a skeletal stem cell. In some embodiments the two methods are combined to provide a source of cartilage. In some embodiments a non-skeletal cell population is included with the reprogramming and/or chondrogenic factors.

In some embodiments the following description focuses on reprogramming, i.e. converting, non-skeletal somatic cells into SSC by contacting them with an effective dose of BMP2 or a variant or mimetic thereof. In other embodiments the description includes methods of skewing the SSC to differentiate into cartilage by contacting with an effective dose of one or both of a VEGF inhibitor and a TGFβ inhibitor; and the use thereof in tissue repair. Other examples of skeletal cells that may be generated by the methods of the invention include skeletal stem cell (SSC), pre-bone cartilage and stromal progenitor (pre-BCSP), BCSP, committed cartilage progenitor (CCP), bone progenitor, B-cell lymphocyte stromal progenitors (BLSP); 6C3 stroma, hepatic leukemia factor expressing stromal cell (HEC); and progeny thereof.

If provided as polypeptides, the factors for inducing chondrogenesis and reprogramming may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Other methods of preparing polypeptides in a cell-free system include, for example, those methods taught in U.S. Application Ser. No. 61/271,000, which is incorporated herein by reference.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. Polypeptides may be produced recombinantly not only directly, but also as a fusion polypeptide with a heterologous polypeptide, e.g. a polypeptide having a specific cleavage site at the N-terminus of the mature protein or polypeptide.

In other embodiments, the factors for reprogramming or inducing chondrogenesis are provided as nucleic acids encoding the polypeptides. Vectors used for providing such nucleic acids to the subject cells will typically comprise suitable promoters for driving the expression, that is, transcriptional activation, of the nucleic acids. This may include ubiquitously acting promoters, for example, the CMV-13-actin promoter, or inducible promoters, such as promoters that are active in particular cell populations or that respond to the presence of drugs such as tetracycline. By transcriptional activation, it is intended that transcription will be increased above basal levels in the target cell by at least about 10-fold, by at least about 100-fold, more usually by at least about 1000-fold. The nucleic acids may be provided directly or in a vector, e.g. a virus, e.g. a lentivirus, retrovirus, adenovirus, adeno associated virus, etc., as known in the art.

When more than one factor is provided, for example when an effective dose of BMP2 is combined with an effective dose of a VEGF inhibitor, a wnt polypeptide, etc. the factors may be provided individually or as a single composition, that is, as a premixed composition, of factors. The factors may be added to the subject cells simultaneously or sequentially at different times. The factors may be provided at the same molar ratio or at different molar ratios. The factors may be provided once or multiple times in the course of treatment. For example, an implant comprising cells and factors may be provided to an individual, and additional factors and/or cells provided during the course of treatment.

The subject progenitor cells and/or combinations of factors may be provided for in vivo use in a cellular solution, in which a hydrating solutions, suspensions, or other fluids that contain bone progenitor cells or factors that are capable of differentiating into bone or cartilage.

Bone or cartilage graft devices and compositions may be provided that are optimized in terms of one or more of composition, bioactivity, porosity, pore size, protein binding potential, degradability or strength for use in both load bearing and non-load bearing cartilage or bone grafting applications. Preferably, graft materials are formulated so that they promote one or more processes involved in bone or cartilage healing which can occur with the application of a single graft material: chondrogenesis, osteogenesis, osteoinduction, and osteoconduction. Chondrogenesis is the formation of new cartilaginous structures. Osteogenesis is the formation of new bone by the cells contained within the graft. Osteoinduction is a chemical process in which molecules contained within the graft (for example, bone morphogenetic proteins and TGF-.beta.) convert the patient's or other bone progenitor cells into cells that are capable of forming bone. Osteoconduction is a physical effect by which the matrix of the graft forms a scaffold on which bone forming cells in the recipient are able to form new bone.

Inclusion of the factors and/or cells of the invention can be used to facilitate the replacement and filling of cartilage or bone material in and around pre-existing structures. In some embodiments, the cells produce chondrocytes first, followed by deposition of extra cellular matrix and bone formation. The bone grafts can provide an osteoconductive scaffold comprising calcium phosphate ceramics which provide a framework for the implanted progenitor cells and local osteocytes to differentiate into bone forming cells and deposit new bone. The use of calcium phosphate ceramics can provide for a slow degradation of the ceramic, which results in a local source of calcium and phosphate for bone formation. Therefore, new bone can be formed without calcium and phosphate loss from the host bone surrounding the defect site. Calcium phosphate ceramics are chemically compatible to that of the mineral component of bone tissues. Examples of such calcium phosphate ceramics include calcium phosphate compounds and salts, and combinations thereof.

In some embodiments, the cells and/or factors are prepared as an injectable paste. A cellular suspension can be added to one or more powdered precursor cells to form an injectable hydrated paste. The paste can be injected into the implant site. In some embodiments, the paste can be prepared prior to implantation and/or store the paste in the syringe at sub-ambient temperatures until needed. In some embodiments, application of the composite by injection can resemble a bone cement that can be used to join and hold bone fragments in place or to improve adhesion of, for example, a hip prosthesis, for replacement of damaged cartilage in joints, and the like. Implantation in a non-open surgical setting can also be performed.

In other embodiments the cells and/or factors are prepared as formable putty. A cellular suspension can be added to one or more powdered minerals to form a putty-like hydrated graft composite. The hydrated graft putty can be prepared and molded to approximate any implant shape. The putty can then be pressed into place to fill a void in the cartilage, bone, tooth socket or other site. In some embodiments, graft putty can be used to repair defects in non-union bone or in other situations where the fracture, hole or void to be filled is large and requires a degree of mechanical integrity in the implant material to both fill the gap and retain its shape.

The present invention provides methods of treating a cartilage or bone lesion, or injury, in a human or other animal subject, comprising applying to the site a composition comprising cells and/or factors of the invention, which may be provided in combinations with cements, factors, gels, etc. As referred to herein such lesions include any condition involving skeletal, including cartilaginous, tissue which is inadequate for physiological or cosmetic purposes. Such defects include those that are congenital, the result from disease or trauma, and consequent to surgical or other medical procedures. Such defects include for example, a bone defect resulting from injury, defect brought about during the course of surgery, osteoarthritis, osteoporosis, infection, malignancy, developmental malformation, and bone breakages such as simple, compound, transverse, pathological, avulsion, greenstick and communuted fractures. In some embodiments, a bone defect is a void in the bone that requires filling with a bone progenitor composition.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express a bone morphogenic protein, such as BMP-2 or BMP-4. See WO 99/39724. Production of these or other growth factors at the site of administration may enhance the beneficial effect of the administered cell, or increase proliferation or activity of host cells neighboring the treatment site.

In Vitro Methods of Conversion, and Uses for Cells Converted In Vitro

In some embodiments, the cells, for example adipose tissue stem cells, hematopoietic stem cells, induced pluripotent stem cells, and the like, or any of the skeletal stem and progenitor cells defined herein, are contacted in vitro with the reprogramming and/or chondrogenic factors. The subject cells may be from any mammal, including humans, primates, domestic and farm animals, and zoo, laboratory or pet animals, such as dogs, cats, cattle, horses, sheep, pigs, goats, rabbits, rats, mice etc. They may be established cell lines or they may be primary cells, where "primary cells", "primary cell lines", and "primary cultures" are used interchangeably herein to refer to cells and cells cultures that have been derived from a subject and allowed to grow in vitro for a limited number of passages.

The subject cells may be isolated from fresh or frozen cells, which may be from a neonate, a juvenile or an adult, and from tissues including skin, muscle, bone marrow, peripheral blood, umbilical cord blood, spleen, liver, pancreas, lung, intestine, stomach, adipose, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−190° C.) indefinitely. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Cells contacted in vitro with the factors defined herein, i.e. the factors that promote reprogramming and/or promote the growth and/or differentiation of chondrocytes, and the like, may be incubated in the presence of the reagent(s) for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

After contacting the cells with the factors, the contacted cells may be cultured so as to promote the survival and differentiation of skeletal stem cells, chondrocytes, or progenitor cell populations defined herein. Methods and reagents for culturing cells are well known in the art, any of which may be used in the present invention to grow and isolate the cells. For example, the cells (either pre- or post-contacting with the factors) may be plated on Matrigel or other substrate as known in the art. The cells may be cultured in media, supplemented with factors. Alternatively, the contacted cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with skeletal survival and differentiation.

Induced skeletal or chondrogenic cells produced by the above in vitro methods may be used in cell replacement or cell transplantation therapy to treat diseases. Specifically, the cells may be transferred to subjects suffering from a wide range of diseases or disorders with a skeletal or cartilaginous component.

In some cases, the cells or a sub-population of cells of interest may be purified or isolated from the rest of the cell culture prior to transferring to the subject. In other words, one or more steps may be executed to enrich for the cells or a subpopulation of cells, i.e. to provide an enriched population of cells or subpopulation of cells. In some cases, one or more antibodies specific for a marker of cells of the skeletal/chondrogenic lineage or a marker of a sub-population of cells of the skeletal lineage are incubated with the cell population and those bound cells are isolated. In other cases, the cells or a sub-population of the cells express a marker that is a reporter gene, e.g. EGFP, dsRED, lacz, and the like, that is under the control of a specific promoter, which is then used to purify or isolate the cells or a subpopulation thereof.

By a marker it is meant that, in cultures comprising cells that have been reprogrammed to become skeletal/chondrogenic cells, the marker is expressed only by the cells of the culture that will develop, are developing, and/or have developed into skeletal/chondrogenic cells. It will be understood by those of skill in the art that the stated expression levels reflect detectable amounts of the marker protein on or in the cell. A cell that is negative for staining (the level of binding of a marker-specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

Cells of interest, i.e. cells expressing the marker of choice, may be enriched for, that is, separated from the rest of the cell population, by a number of methods that are well known in the art. For example, flow cytometry, e.g. fluorescence activated cell sorting (FACS), may be used to separate the cell population based on the intrinsic fluorescence of the marker, or the binding of the marker to a specific fluorescent reagent, e.g. a fluorophor-conjugated antibody, as well as other parameters such as cell size and light scatter. In other words, selection of the cells may be effected by flow cytometry Although the absolute level of staining may differ with a particular fluorochrome and reagent preparation, the data can be normalized to a control. To normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but are not as intense as the most brightly staining cells normally found in the population. An alternative control may utilize a substrate having a defined density of marker on its surface, for example a fabricated bead or cell line, which provides the positive control for intensity.

Other methods of separation, i.e. methods by which selection of cells may be effected, based upon markers include, for example, magnetic activated cell sorting (MACS), immunopanning, and laser capture microdissection.

Enrichment of the cell population may be performed about 3 days or more after contacting the cells with the factors of the invention, e.g. 3 days, 4 days, 5 days, 6 days, 7 days, 10 days, 14 days, or 21 days after contacting the somatic cells with the factors. Populations that are enriched by selecting for the expression of one or more markers will usually have at least about 80% cells of the selected phenotype, more usually at least 90% cells and may be 95% of the cells, or more, of the selected phenotype.

In addition to the transplantation methods described above, cells isolated from tissue, or induced by the methods described above in vitro may be used as a basic research or drug discovery tool, for example to evaluate the phenotype of a genetic disease, e.g. to better understand the etiology of the disease, to identify target proteins for therapeutic treatment, to identify candidate agents with disease-modifying activity, e.g. to identify an agent that will be efficacious in treating the subject. For example, a candidate agent may be added to a cell culture comprising iSSC derived from the subject's non-skeletal cells, or any of the skeletal and chondrogenic progenitor cells described herein, and the effect of the candidate agent assessed by monitoring output parameters such as survival, the ability to form bone or cartilage, and the like, by methods described herein and in the art.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The methods described herein also provide a useful system for screening candidate agents for activity in modulating cell conversion into cells of a skeletal or chondrogenic lineage, e.g. chondrocytes, osteoblasts, or progenitor cells thereof. In screening assays for biologically active agents, cells, usually cultures of cells, are contacted with a candidate agent of interest in the presence of the cell reprogramming or differentiation system or an incomplete cell reprogramming or differenaitation system, and the effect of the candidate agent is assessed by monitoring output parameters such as the level of expression of genes specific for the desired cell type, as is known in the art, or the ability of the cells that are induced to function like the desired cell type; etc. as is known in the art.

Isolation of Bone/Chondrogenin/Stromal Progenitor Cells

The subject bone progenitor cells of the invention are separated from a complex mixture of cells by techniques that enrich for cells having the characteristics as described. The progenitor cells of the invention have been characterized in a lineage, as set forth in FIG. 2G. While the initial characterization was performed on mouse cells, human cells may be characterized with the functional homologs of the markers, e.g. CD200, 6C3, PDPN, CD105, CD90, CD45, Tie2 and $\alpha_v$ integrin. Methods and compositions are provided for the separation and characterization of such bone progenitor cells. The cells may be separated from other cells by expression of these specific cell surface markers.

For isolation of cells from tissue, an appropriate solution may be used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The tissue may be enzymatically and/or mechanically dissociated. In some embodiments the bone tissue is treated with a gentle protease, e.g. dispase, etc., for a period of time sufficient to dissociate the cells, then is gently mechanically dissociated.

An initial separation may select for cells by various methods known in the art, including elutriation, Ficoll-Hypaque or flow cytometry using the parameters of forward and obtuse scatter.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. Of particular interest is the use of antibodies as affinity reagents. The details of the preparation of antibodies and their suitability for use as specific binding members are well known to those skilled in the art. Depending on the specific population of cells to be selected, antibodies having specificity for CD105 and CD90 are contacted with the starting population of cells. Optionally, reagents specific for CD45, Tie2 and $\alpha_v$ integrin are also included.

As is known in the art, the antibodies will be selected to have specificity for the relevant species, i.e. antibodies specific for human markers are used for selection of human cells; antibodies specific for mouse markers are used in the selection of mouse cells, and the like.

Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for bone progenitor activity are achieved in this manner. The subject population will be at or about 50% or more of the cell composition, and usually at or about 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or stromal cells for proliferation and differentiation.

The present methods are useful in the development of an in vitro or in vivo model for bone function and are also useful in experimentation on gene therapy and for artificial organ construction. The developing bones serve as a valuable source of novel growth factors and pharmaceuticals and for the production of viruses or vaccines, for in vitro toxicity and metabolism testing of drugs and industrial compounds, for gene therapy experimentation, for the construction of artificial transplantable bones, and for bone mutagenesis and carcinogenesis The features and advantages of the present invention will be more clearly understood by reference to the following examples, which are not to be construed as limiting the invention.

EXPERIMENTAL

Example 1

Interchangeable Fates of Osteogenic and Chondrogenic Progenitors Revealed by Comprehensive Lineage-Mapping of Multipotent Skeletal Stem Cells Bone, cartilage, and bone marrow stroma are the primary components of the skeleton but the origins of postnatal skeletal tissues remain unclear. Here, we map bone and cartilage development from a population of highly pure, post-natal skeletal stem cells (mouse Skeletal Stem Cell, mSSC) and its downstream distinct progenitors of bone, cartilage and stromal tissue. We then determined the mSSC lineage relationships to its progeny. We investigated the transcriptome of the stem/progenitor cells for unique gene expression patterns that would indicate potential intrinsic and extrinsic regulators of mSSC lineage commitment. These analyses reveal that supportive stroma generated from the mSSC reflexively regulates differentiation of the mSSC and also regulates hematopoiesis. We demonstrate that some mSSC niche factors can be potent inducers of skeletal regeneration, and several specific combinations of recombinant mSSC niche factors can activate mSSC genetic programs in situ, even in non-skeletal tissues, resulting in de-novo formation of cartilage or bone and bone marrow stroma.

By implementing a "Rainbow Mouse" system, we systematically isolated non-hematopoietic stromal cells from clonogenic regions of bone tissue and assayed their ability to differentiate into skeletal tissues in vivo in a heterotopic transplant setting. We then identified eight subpopulations of progenitor cells by FACS fractionation and transcriptional analysis. Among these subpopulations we found a mouse skeletal stem cell (mSSC) capable of generating bone, cartilage, and bone marrow. Subsequently, we identified the lineal relationship among this mSSC and the other seven subpopulations to develop a lineage map of skeletogenic progenitors. We next turned our attention to the mechanisms and/or factors in the niche that regulate mSSC proliferation and differentiation toward specific lineages, especially towards the development of cartilage. By manipulation of identified morphogens, important in maintaining the skeletal niche microenvironment, we could induce ectopic osteogenesis in adipose tissue. We could also skew lineage determination from osseous to chondrogenic tissue by further manipulation of identified niche factors that are instrumental in determining skeletal stem and progenitor cell fate. We, thus, demonstrate the utility of this lineage map, and the identified relationships between the mSSC and its progeny, by distinguishing specific skeletogenic niche factors that could be translated for therapeutic skeletal regeneration.

Identification of the skeletal stem cell, its progeny, and their lineage relationships Bone and cartilage are derived from clonal, lineage-restricted progenitors. A primary challenge in purifying novel tissue progenitors is identifying molecular markers that can accurately distinguish these rare cells from their environment. Studies indicate that select populations of skeletogenic progenitor cells can be genetically traced in transgenic mice engineered to express GFP, or Cre-Recombinase, under the regulatory control of promoters driving expression of specific genes such as Nestin or Mx1. However, since Nestin and Mx1 are broadly expressed in a variety of tissues and cell types, expression of these markers in different cells may not necessarily imply that they share a common lineage. Thus, we used a "Rainbow mouse" model to evaluate clonal-lineage relationships in vivo to determine whether mesenchymal tissues in bone—including stroma, fat, bone, cartilage, and muscle—share a common progenitor.

Figure 8A:
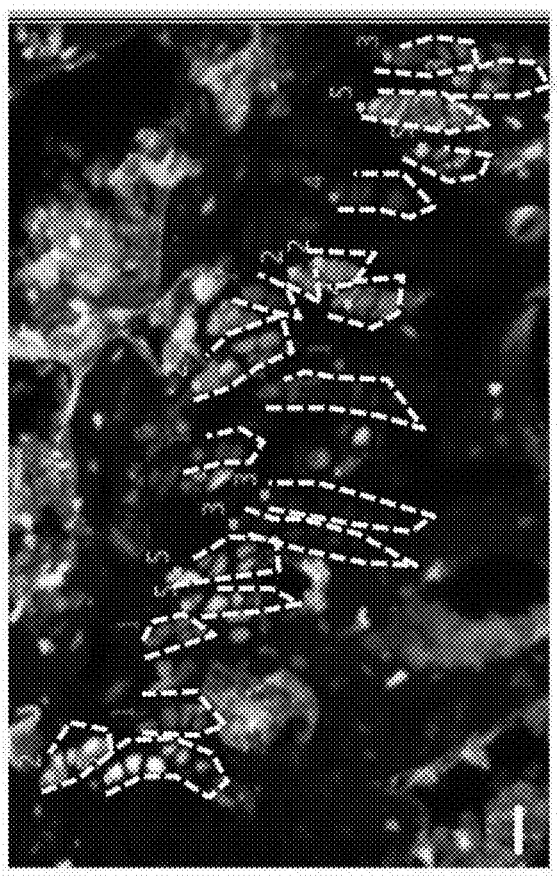
Figure 8B:
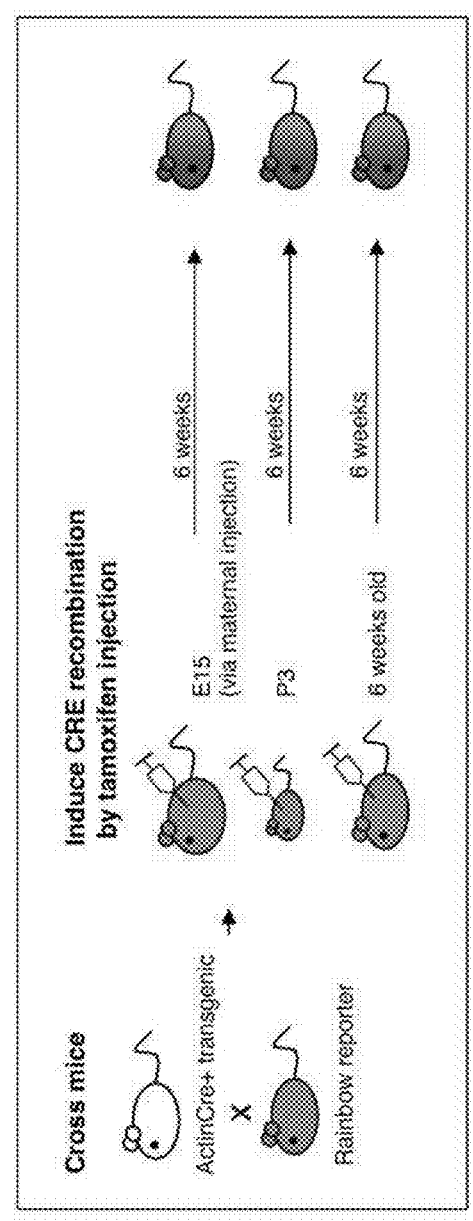

The Rainbow mouse system is a multi-color Cre-dependent marker system that harbors a four color reporter construct (red, yellow, green, blue: see Experimental Methods Section). To visualize clonal patterns within all tissues, we crossed 'Rainbow' mice with mice harboring a tamoxifen-inducible ubiquitously expressed Cre under the promoter of the actin gene (Actin-Cre-ERT) (FIG. 10). We then induced Cre expression in the progeny by tamoxifen injection at distinct developmental timepoints, including embryonic day 15 (E15), postnatal day 3 (P3) and at 6 weeks (young adults) (FIG. 10). The induction of Cre-recombinase activity triggers constitutive expression of up to 16 distinct random arrangements of RFP, GFP, CFP, and YFP in all cells, including stem cells. Six weeks after this recombinase activation, clonal regions could be detected as uniformly labeled areas of a distinct color (FIG. 8A, B).

Using this system, we observe clonal regions in the bone, particularly at the growth plate, that encompass bone, cartilage, and stromal tissue, but not hematopoietic, adipose, or muscle tissue at all time-points (induction at E15, P3 and postnatal week 6) (FIG. 1A, C, D, FIG. 8D). These data indicate that bone, cartilage, and stromal tissue are clonally derived in vivo from lineage-restricted stem and progenitor cells that do not also give rise to muscle and fat, at least at the time-points examined (from E15 to postnatal week 6) (FIG. 8D).

There is a mild reduction in skeletal clonal activity in the femoral growth plate of the mice induced at the postnatal week 6, which likely reflects the gradual postnatal decline in growth (FIG. 8C, arrowhead illustrating clonal regions in the insets of (ii)-(iv)). We also observe clonal regions in the metacarpals and metatarsals and in the bones of the axial skeleton, namely the sternum and ribs (FIG. 8E-G). Purified cartilage, bone and stromal progenitors cells are heterogeneous and lineage restricted.

After determining that bone, cartilage, and stromal tissue are clonally derived from lineage restricted stem and progenitor cells in vivo, we sought to purify specific clonal skeletogenic populations by prospective isolation using fluorescence-activated cell sorting (FACS). Because we had observed a high frequency of clonal regions in the growth plate during our 'Rainbow mouse' clonal analysis, we isolated cells from the growth plates of femora by enzymatic and mechanical dissociation and analyzed them by FACS for differential expression of CD45, Ter119, Tie2, and AlphaV integrin. These surface markers correspond to those present on hematopoietic (CD45, Ter119), vascular and hematopoietic (Tie2), and osteoblastic (AlphaV integrin) cells.

We found that the growth plate had a high frequency of cells that were CD45-Ter119-Tie2-AlphaV+, hereafter referred to as [AlphaV+] cells. Based on a subsequent microarray analysis of the [AlphaV+] population showing differential expression of CD105, Thy, 6C3, and CD200, we fractionated this population into eight sub-populations (FIGS. 1B and E). To evaluate the intrinsic ability of the eight sub-populations to give rise to skeletal tissue, we isolated 20,000 cells of each subpopulation from the long bones (femora, tibiae, humeri, radii), the ribs and the sternum of GFP+ mice (FIG. 1E) and transplanted them beneath the renal capsule of immunocompromised RAG-2/gamma (c)KO mice (FIG. 1H).

We had previously determined that the subcapsular location in the kidney is an ideal extra-skeletal site for engraftment of transplanted skeletogenic cells. Four weeks after transplantation, we explanted the GFP-labeled kidney grafts and processed the tissues for histological analysis to determine their developmental outcome (FIG. 1F). The eight subpopulations exhibited different developmental fates (FIG. 1F-G): three followed a pattern of endochondral ossification, giving rise to grafts consisting of bone, cartilage and marrow (FIG. 1F-G: populations a, e, f); four gave rise to primarily bone with minimal cartilage and no marrow (FIG. 1F-G: populations b, c, d, h); and one gave rise to predominantly cartilaginous tissue with minimal bone and no marrow (FIG. 1F-G: population g). These results indicate that the skeletogenic progenitors are diverse, with distinct cell surface marker profiles and skeletal tissue fates, similar to the diverse hematopoietic progenitor cells that generate various terminally differentiated blood cells. To ensure that the [CD45+Ter 119+] or [Tie2+] subpopulations did not contain subpopulations of skeletogenic cells, we isolated the [CD45+Ter 119+] and [Tie2+] cell populations (which we had previously excluded on FACS fractionation) from the long bones of P3 GFP-labeled mice by mechanical and enzymatic digestion and subsequent FACS fractionation.

We then transplanted 20,000 cells of each of the subsets beneath the renal capsule of immunodeficient RAG-2/gamma(c)KO mice to assess their intrinsic skeletogenic potential. Unlike the eight subpopulations of the [AlphaV+] fraction, the CD45/Ter119+ and Tie2+ subsets were not found to form bone, cartilage or stroma four weeks after transplantation (FIG. 15D), further emphasizing the existence of distinct progenitors of bone, cartilage and stromal tissue in the mouse skeleton.

Identification of a post-natal skeletal stem cell. We hypothesized that skeletogenesis may proceed through a developmental hierarchy of lineage-restricted progenitors as seen in hematopoiesis, the system of organogenesis that has been most thoroughly enumerated. Thus, we again isolated the eight cell subpopulations from the femoral growth plate, based on differential expression of CD105, CD200, Thy, and 6C3 cell surface markers in the [AlphaV+] population.

We next attempted to determine the differentiation capacity of each subpopulation and to identify lineage relationships that might be present among the subpopulations. We observed that the [CD45-Ter119-Tie2-AlphaV+Thy-6C3-CD105-CD200+] subpopulation lineally generates all of the other (seven) subpopulations through a sequence of stages both in vitro and in vivo, beginning with generation of two multipotent progenitor cell types: firstly, the [CD45-Ter119-Tie2-AlphaV+Thy-603-CD105-CD200-] cell population, hereafter referred to as the pre-BCSP (for pre-bone cartilage and stromal progenitor); and the [CD45-Ter119-Tie2-AlphaV+Thy-6C3-CD105+] cell population which we previously described as the BCSP; for bone, cartilage, and stromal progenitor.

The [CD45-Ter119-Tie2-AlphaV+Thy-6C3-CD105-CD200+] subpopulation generates in vitro and in vivo all of the other (seven) subpopulations in a lineal fashion. In vitro, the freshly sorted cells were cultured for a period of 25 days, at which point they were re-fractionated by FACS (FIG. 2A(i), FIG. 2B(i), (ii)), and subsequently transplanted beneath the renal capsule (FIG. 2A(i), FIG. 2B(iii)). In vivo, the purified cells were transplanted beneath the renal capsule and explanted one month later for dissociation and FACS analysis (FIG. 2A(ii), FIG. 2C(i), (ii)) or immunohistochemistry (FIG. 2C(iii)).

These data demonstrate that the [CD45-Ter119-Tie2-AlphaV+Thy-603-CD105-CD200+] subpopulation generates all of the other (seven) subpopulations in a linear fashion both in vitro and in vivo. Single sorted cells from the [CD45-Ter119-AlphaV+Thy-603-CD105-CD200+] subpopulation also generated all of the other subpopulations in a linear fashion both in vitro and in vivo (FIG. 2D, FIG. 2E).

In vitro: Individual [CD45-Ter119-Tie2-AlphaV+Thy-6C3-CD105-CD200+] cells were plated and cultured for 14 days (FIG. 2D(ii)). FACS analysis of the resultant primary colonies indicated that they contained clones of the original cell and all other (seven) subpopulations of the [AlphaV+] population (FIG. 2E(iv): middle panel FACS plot). These colonies contained both collagen 2(+) cartilage and osteocalcin (+) bone tissue when examined by immunohistochemistry (FIG. 2E (iii)). Furthermore, when a single freshly-sorted [CD45-Ter119-Tie2-AlphaV+Thy-6C3-CD105-CD200+] cell isolated from the primary colony was again plated and cultured for 14 days, the resultant secondary colony contained clones of the original cell and again all other subpopulations (FIG. 2E(ii)) on FACS analysis (FIG. 2E(iv): bottom panel FACS plot). These results demonstrate that the in vitro self-renewal of a single [CD45-Ter119-Tie2-AlphaV+Thy-6C3-CD105-CD200+] cell maintained the skeletogenic properties of freshly-isolated [CD45-Ter119-Tie2-AlphaV+Thy-6C3-CD105-CD200+] cells.

Figure 9A:
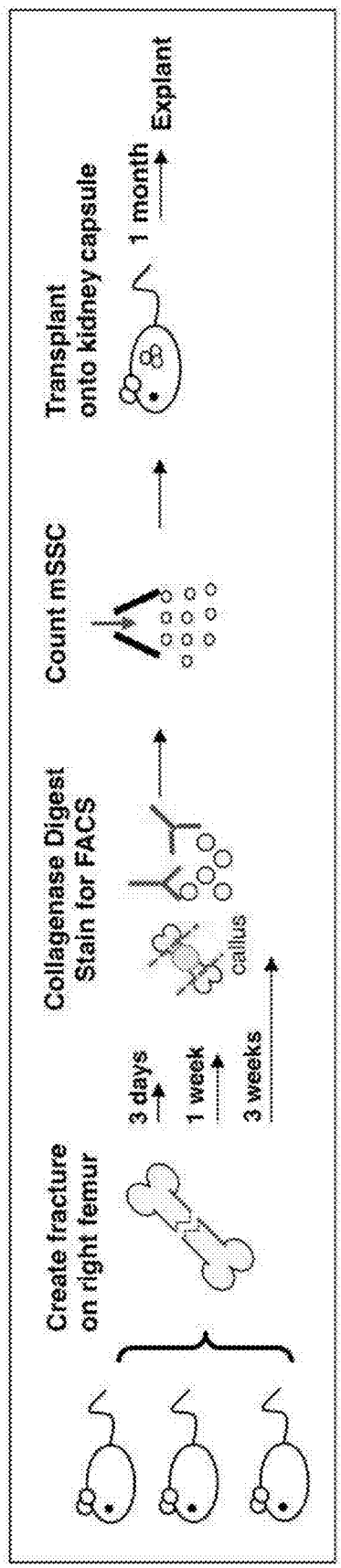
FIG. 9A-9D: Injury induces local mSSC expansion.
Figure 9C:
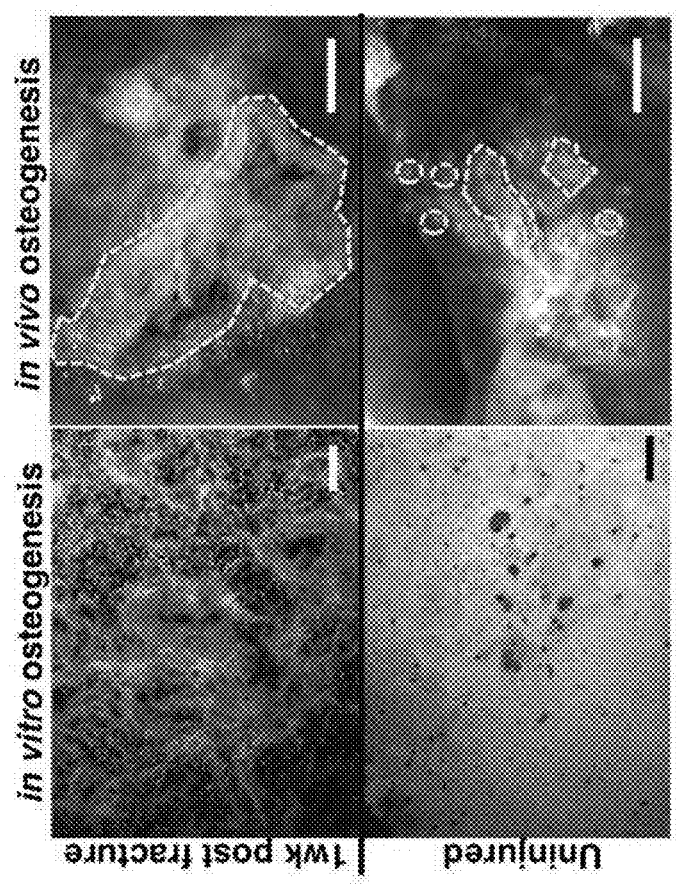
Figure 9B:
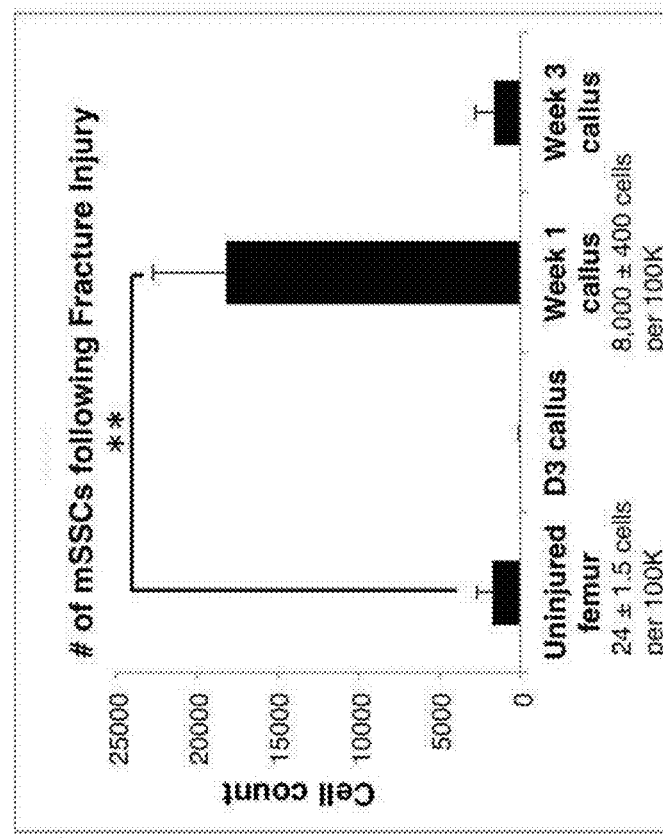

In vivo: When transplanted individually, [CD45-Ter119-Tie2-AlphaV+Thy-6C3-CD105-CD200+] cells did not engraft efficiently beneath the renal capsule, perhaps reflecting their need for a supportive microenvironment—i.e., a skeletal stem cell niche. Therefore, we co-transplanted individual GFP-labeled [CD45-Ter119-Tie2-AlphaV+Thy-6C3-CD105-CD200+] cells with five-thousand unsorted, RFP-labeled cells isolated from the long bones of P3 mice to simulate a skeletal stem cell niche (FIG. 2D(i)). Two-weeks after transplantation, we explanted the grafts for serial sectioning and immunohistochemical analysis. The GFP-labeled transplanted cells differentiated into both alcian blue stained chondrocytes and saffron-stained osteocytes in vivo (FIG. 2F(iv), (vi)), consistent with their in vitro properties (FIG. 2E(iii)). These data indicate that the [CD45-Ter119-Tie2-AlphaV+Thy-6C3-CD105-CD200+] population possesses definitive stem cell-like characteristics of self-renewal and multipotency. We therefore conclude that the [CD45-Ter119-Tie2-AlphaV+Thy-6C3-CD105-CD200+] cell population represents a mouse Skeletal Stem Cell (mSSC) population in post-natal skeletal tissues (FIG. 2G), and that the seven other subpopulations of the [AlphaV+] population are mSSC progeny.

mSSCs identified by these criteria were also detected in other regions of the skeleton, including the tail, spine, ribs, pelvis, neural cranium, mandible and phalanges, which indicates that mSSC is also important for postnatal maintenance of these bones. (FIG. 14) Highlighting the potential regenerative capabilities of the mSSC, we have evinced that the number of mSSCs is significantly higher in the callus of a fractured femur than in the contralateral uninjured femur; this difference was greatest 7 days after a fracture (FIG. 9A-B).

Figure 9D:
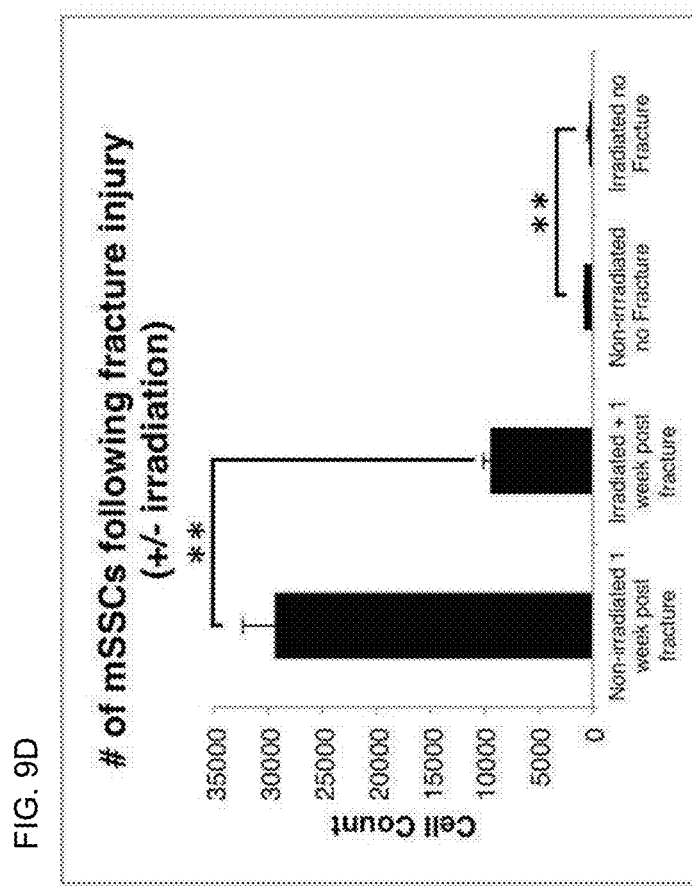
Figure 11A:
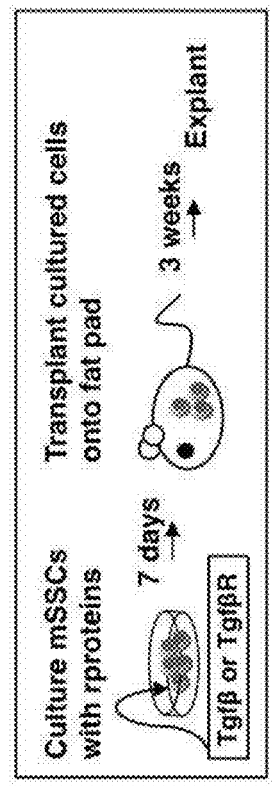
FIG. 11A-11B: Tgfβ antagonism promoted cartilage formation in mSSCs.
Figure 11B:
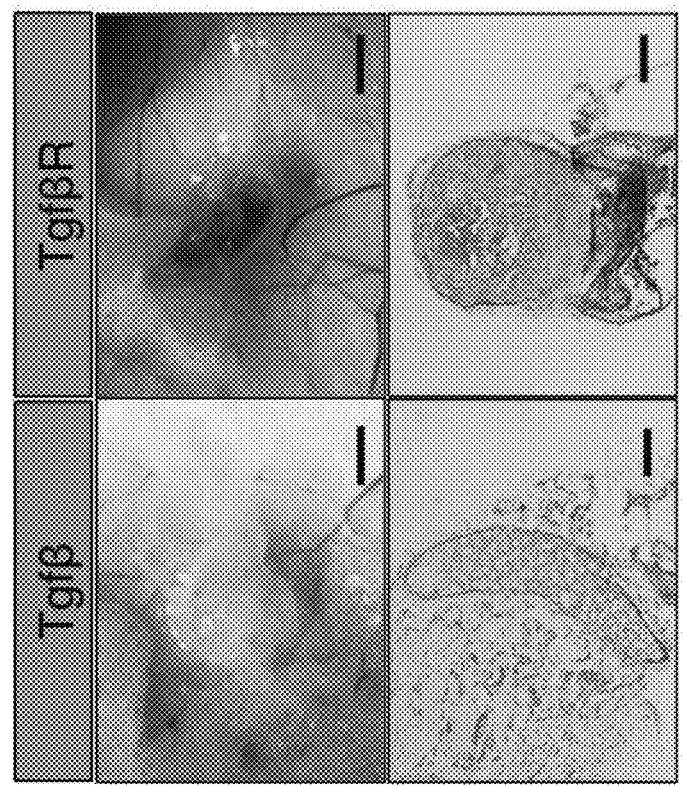

In addition, we have seen three further phenomena, which emphasize the role of the mSSC in regeneration post injury. Firstly, we observe that mSSC isolated from a fracture callus have enhanced osteogenic capacity (in comparison to those cells isolated from an uninjured femur) when cultured in vitro in osteogenic differentiation medium, demonstrating significantly greater uptake of Alizarin Red stain in comparison to mSSC isolated from an uninjured femur (FIG. 9C left panel). Secondly, when we transplanted 10,000 mSSC, isolated from either a fracture callus or uninjured bone, beneath the renal capsule and explanted the grafts one month later, we saw that while both groups of cells produced grafts consistent of bone and marrow, the grafts produced by mSSC obtained from the fracture environment resulted in markedly larger grafts than those produced by mSSC isolated from the uninjured bone, highlighting the intrinsic alteration of the activity of the mSSC in the presence of injury (FIG. 9C: right panel). Finally, as is well known that irradiation results in osteopenia and reduced fracture healing, we next examined the mSSC activity in response to injury following irradiation. Here, we see that when we irradiated the mice 12 hours prior to fracture induction, we found that there was a significant reduction in mSSC expansion at one week following fracture in comparison to non-irradiated femora 1-week post fracture (FIG. 9D).

Figure 12A:
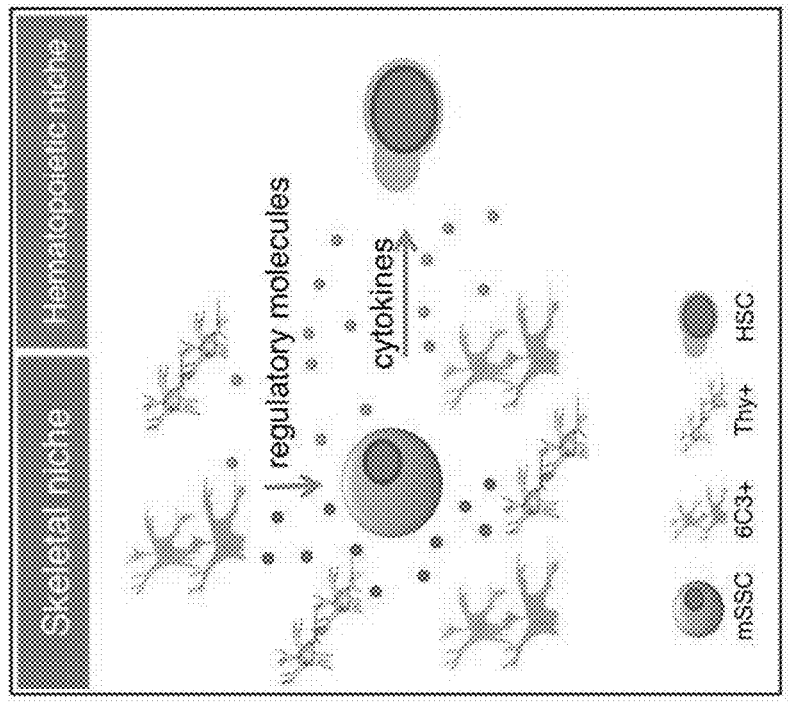
FIG. 12A-12B: Heatmap of gene expression on skeletal subsets.
Figure 12B:
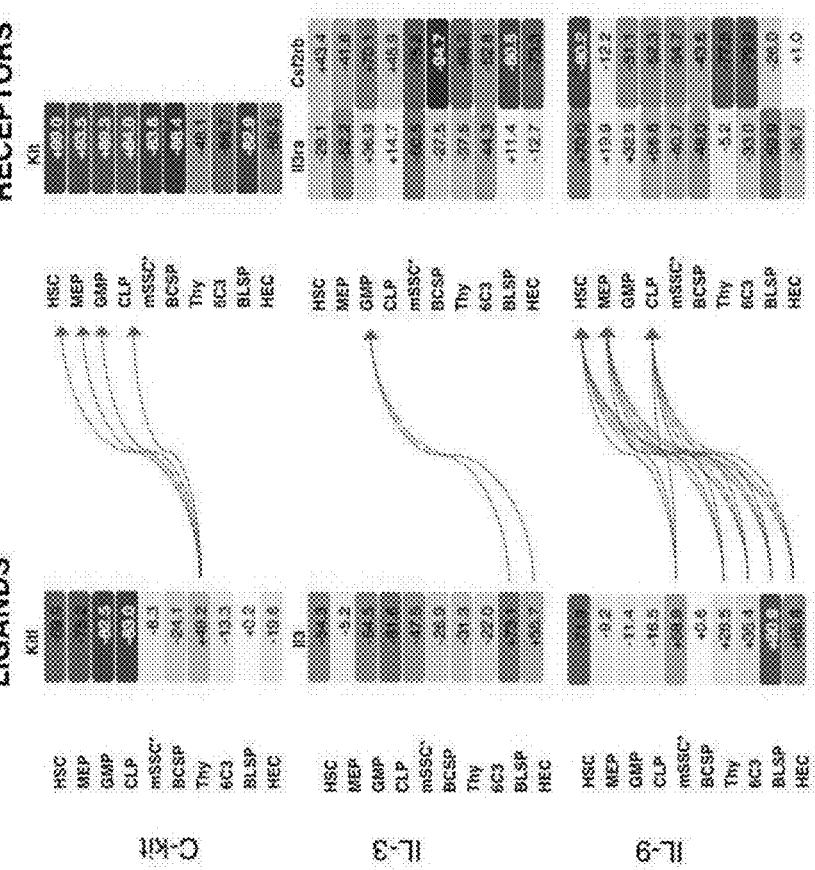
Figure 13A:
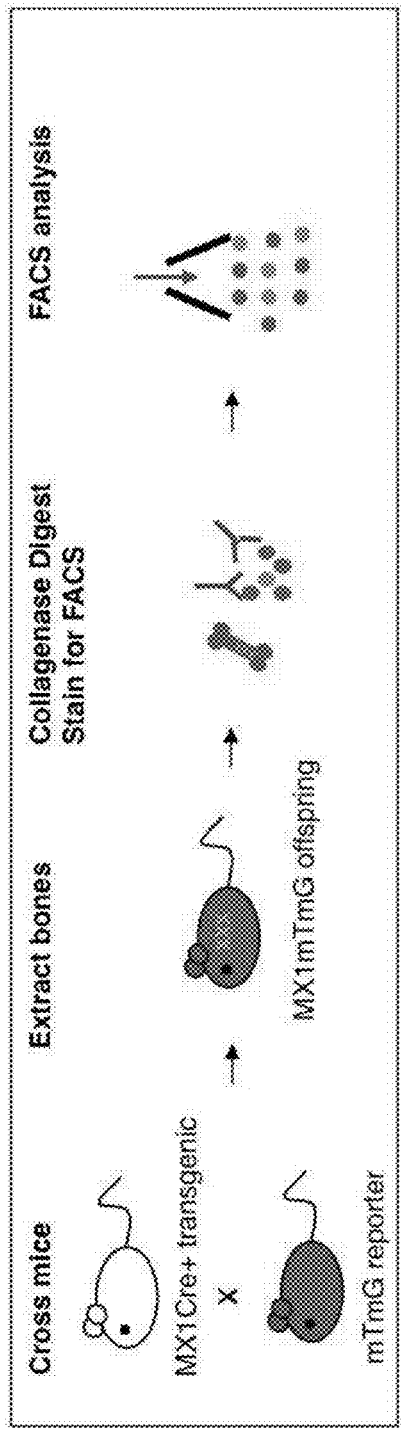
FIG. 13A-13B: Mx1 Cre-labeled cells encompass the mSSC population FIG. 13A Scheme of experiment: Mx1-Cre-ERT mice were induced at E15. On P3, the femora were harvested and cells were isolated following mechanical and enzymatic dissociation and subsequent FACS fractionation.
Figure 13B:
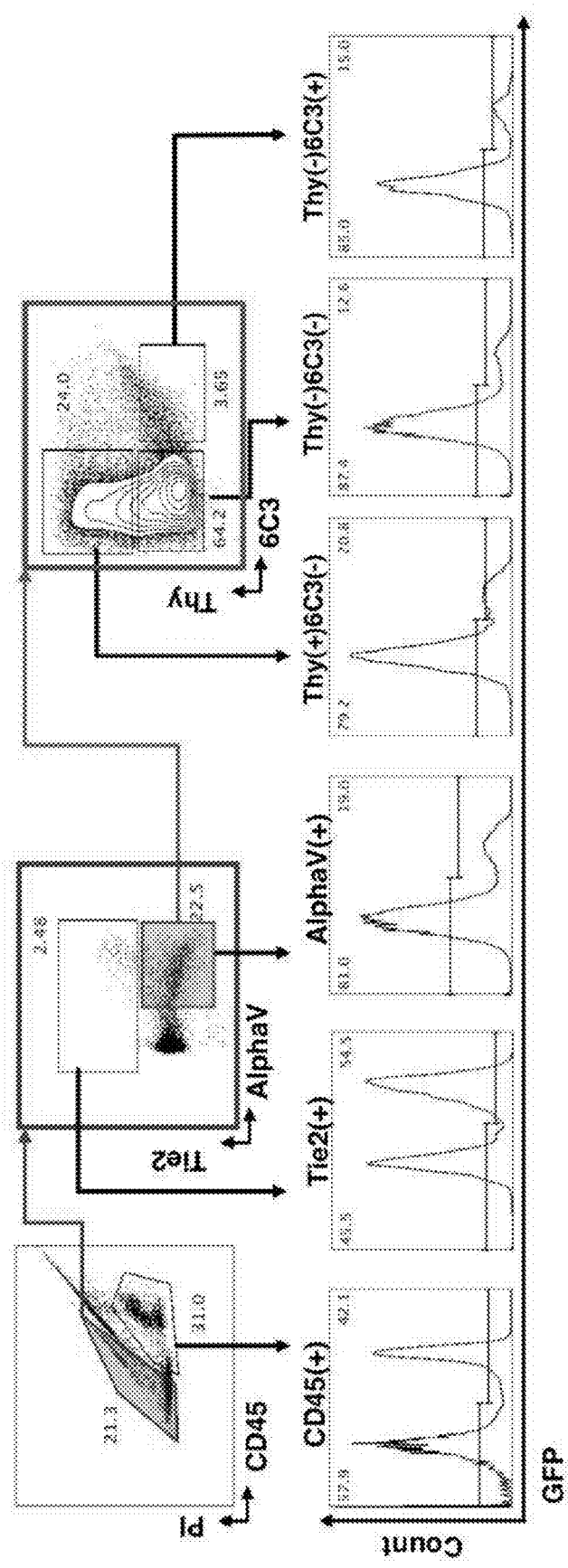

These data thus highlight the functional regenerative capacity of the mSSC. Based on the analyses described above, we defined a lineage tree of skeletal stem/progenitor cells (FIG. 2G). The mSSC initiates skeletogenesis by producing a hierarchy of increasingly fate-limited progenitors, similar to that of the HSC. The multipotent and self-renewing mSSC first gives rise to multipotent progenitors, pre-bone cartilage stromal progenitor cells (pre-BCSPs) and bone cartilage stromal progenitor cells (BCSPs). Both of these cell types then produce the following oligolineage progenitors: committed cartilage progenitors (CCPs) [CD45-Ter119-Tie2-AlphaV+Thy+6C3-CD105+CD200+]; the Thy subpopulation, [CD45-Ter119-Tie2-AlphaV+Thy+6C3-CD105+] hereafter referred to as Thy; B-cell lymphocyte stromal progenitors, BLSPs [CD45-Ter119-AlphaV+Thy+6C3-CD105-]; the 6C3 subpopulation, [CD45-Ter119-AlphaV+Thy− 6C3+CD105-] hereafter referred to as 6C3; and the hepatic leukemia factor expressing cell, HEC [CD45-Ter119-AlphaV+Thy-6C3+CD105-] (FIG. 2G). mSSC-derived lineages include cell types that we have previously characterized such as the Thy, BLSP, and the 6C3 subpopulations, which possess distinct hematopoietic supportive capabilities (FIG. 12A, B).

Identification of Factors that Regulate Skeletal Stem and Progenitor Cell Activity and Differentiation. The mSSC niche is composed of other skeletal-lineage cells that regulate mSSC activity. In initial experiments, we noted that the earliest skeletogenic population from fetal limbs were triple negative for Thy, 6C3, and CD105 ([CD45-Ter119-Tie2-AlphaV+Thy-6C3-CD105-], hereafter, collectively denoted as TN, Triple Negative cells). The TN cell gave rise to CD105+, Thy+ and 603+/− cells in vitro and in vivo, and the TN cells were also able to self renew in vitro. Thus the TN cells were our earliest version of a population that was enriched for the mSSCs. This is the same population that we used when we performed our microarray analysis (described as *mSSC; FIG. 3).

The microarray analysis of the *mSSC population revealed a set of markers that could potentially enrich for mSSCs even further. Amongst several possible candidates we observed that CD200 appears to significantly enhance the colony-forming unit activity of the TN cell. Thus, all of the subsequent experiments including the recent single cell RNA sequencing were performed on the mSSC with the described immunophenotype in FIG. 2G ([CD45-Ter119-Tie2-AlphaV+Thy-6C3-CD105-CD200+]). Similarly, the immunophenotype of the committed cartilage progenitor (CCP) was further refined with the observation of the importance of CD200 in further subfractionation of the skeletogenic stem/progenitor cells (FIG. 2G).

Once we had isolated the mSSC, we turned our attention to identifying the cell types that make up the mSSC niche (the microenvironment that supports and regulates stem cell activity). We first conducted microarray gene expression analyses of a freshly-sorted pure population of mSSCs and five of its progenitor populations: (I) BCSP; (ii) Thy; (iii) 603; (iv) BLSP; and (v) HEC. The purpose of these gene expression analyses was to identify receptors to signaling pathways that may regulate the activity of the mSSC and its progeny (FIG. 3D-E).

To interpret the gene expression profiles of these cells, we used the Gene Expression Commons, a platform that normalizes microarray data against a large collection (n=11, 939) of publicly available microarray data from the National Center for Biotechnology Information Gene Expression Omnibus (NCBI GEO). Thus, we generated heat maps representing fold-change of gene expression and performed pathway statistical analysis with the Ingenuity Pathway Analysis Software (QIAGEN Redwood City).

Figure 3A:
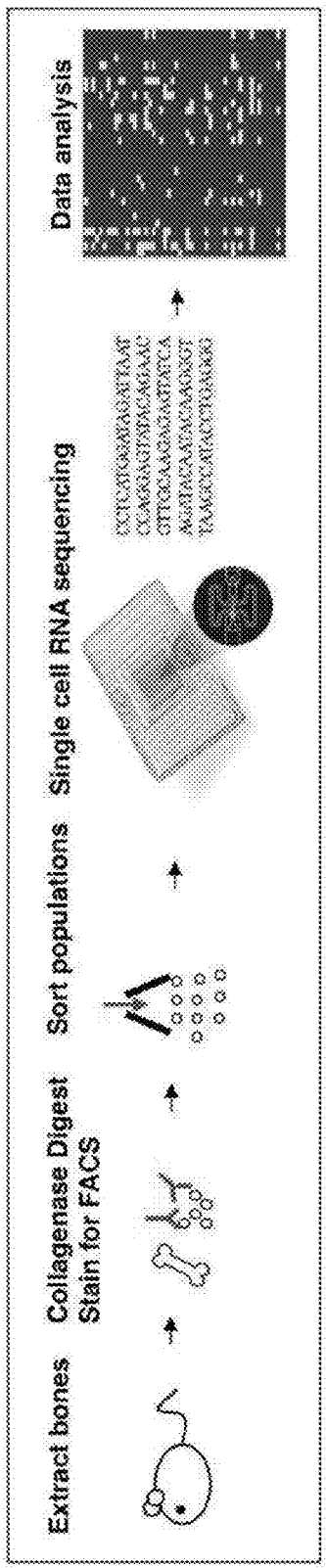
Figure 3B:
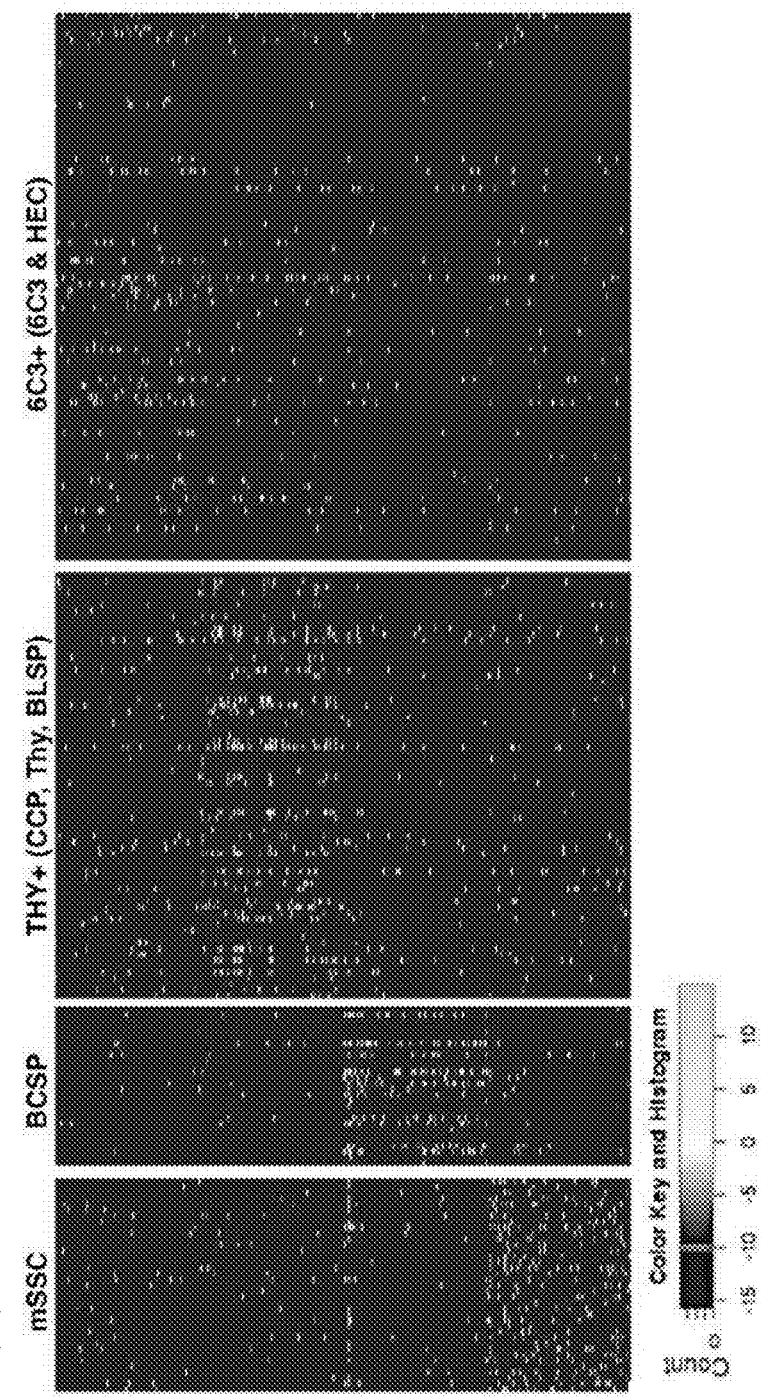
Figure 3C:
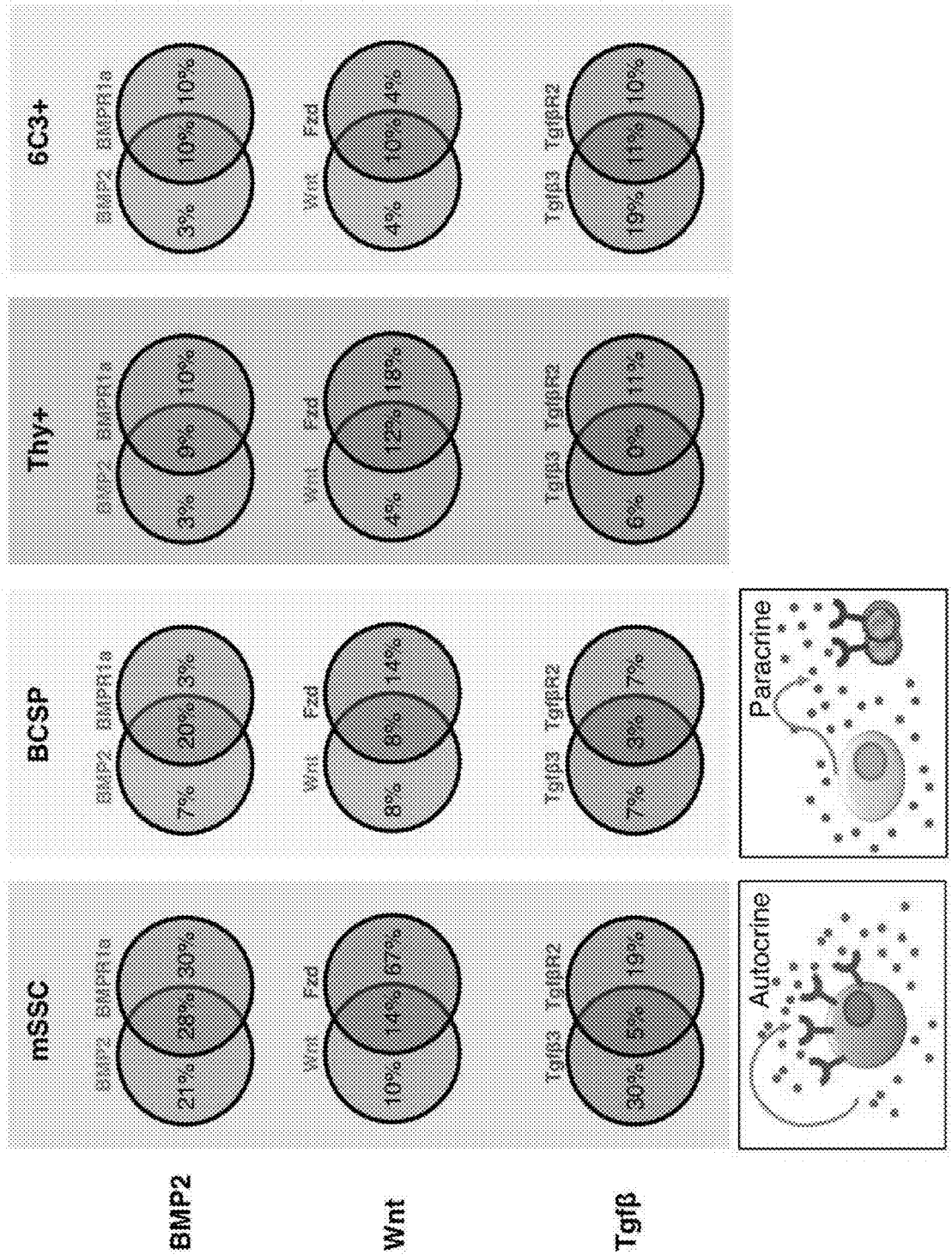
Figure 3D:
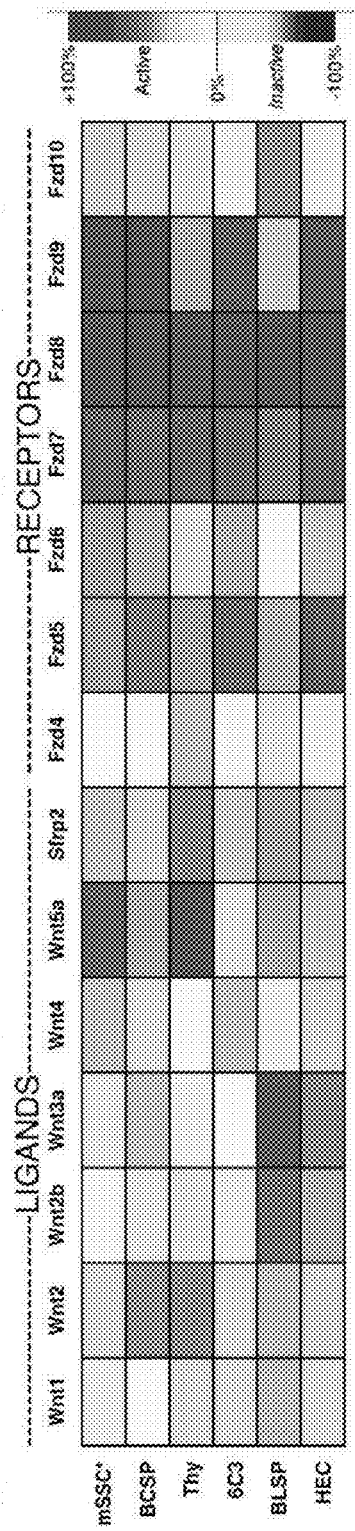
Figure 3F:
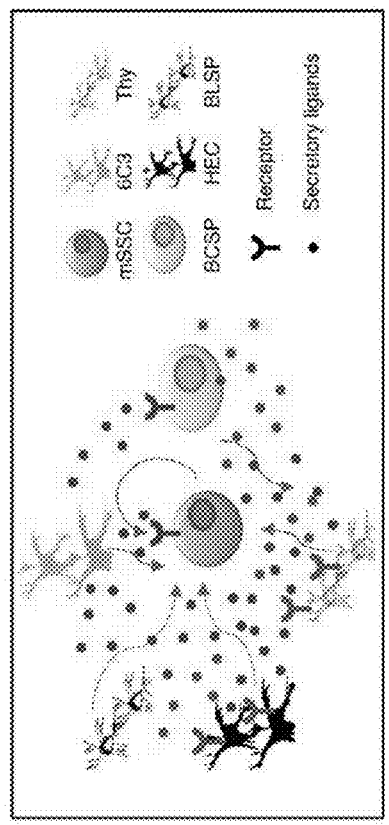
Figure 3G:
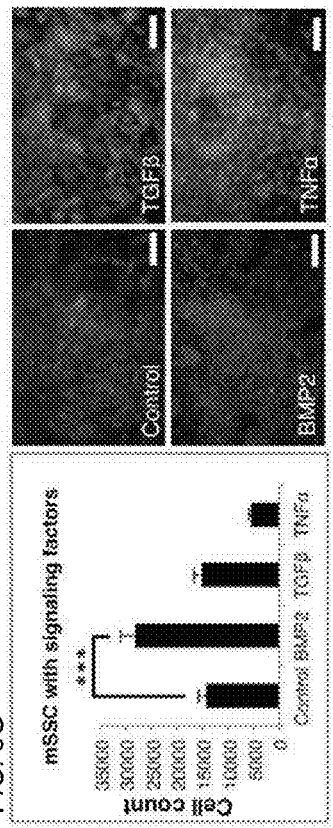
Figure 3E:
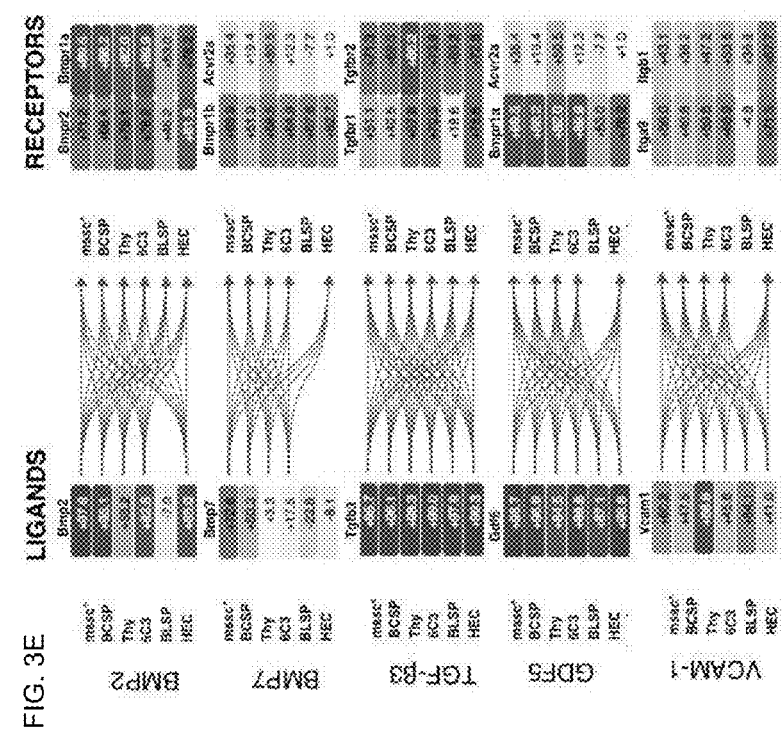
Figure 3L:
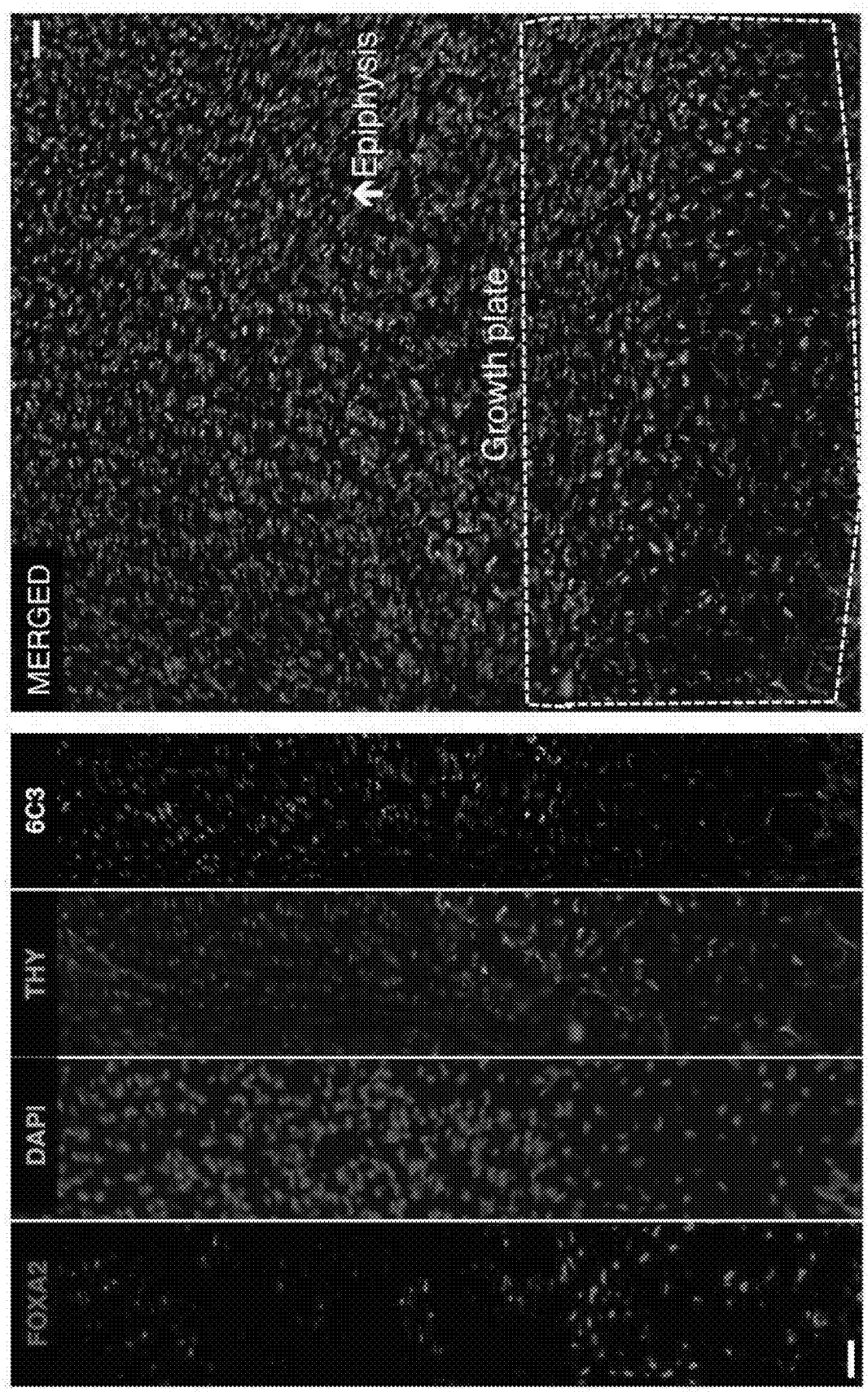

The *mSSC and its progeny differentially express many receptors involved in transforming growth factor (TGF) beta (specifically bone morphogenetic protein (BMP)) and WNT signaling pathways, and cognate morphogens of these pathways, including BMP2, TGF-β3 and Wnt3a (FIG. 3D-E). These results suggest that autocrine and/or paracrine signaling among mSSCs* and their progeny may positively regulate their own expansion (FIG. 3F). Furthermore, single cell RNA sequencing revealed co-expression of BMP2 and its receptor (BMPR1a) (FIG. 3A-C) in the mSSC, illustrating the potential for autocrine signaling in the mSSCs.

Figure 15A:
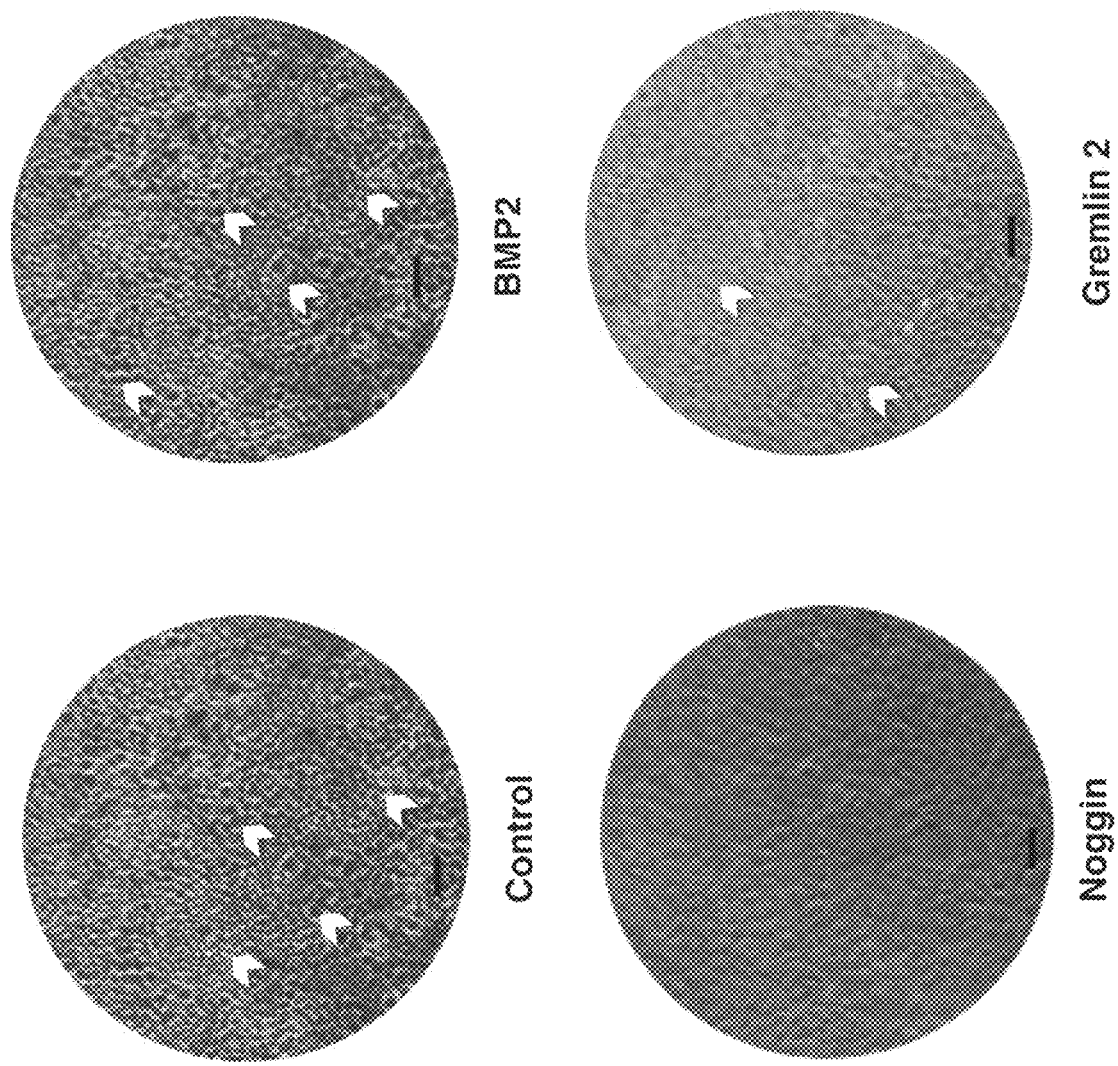
Figure 15D:
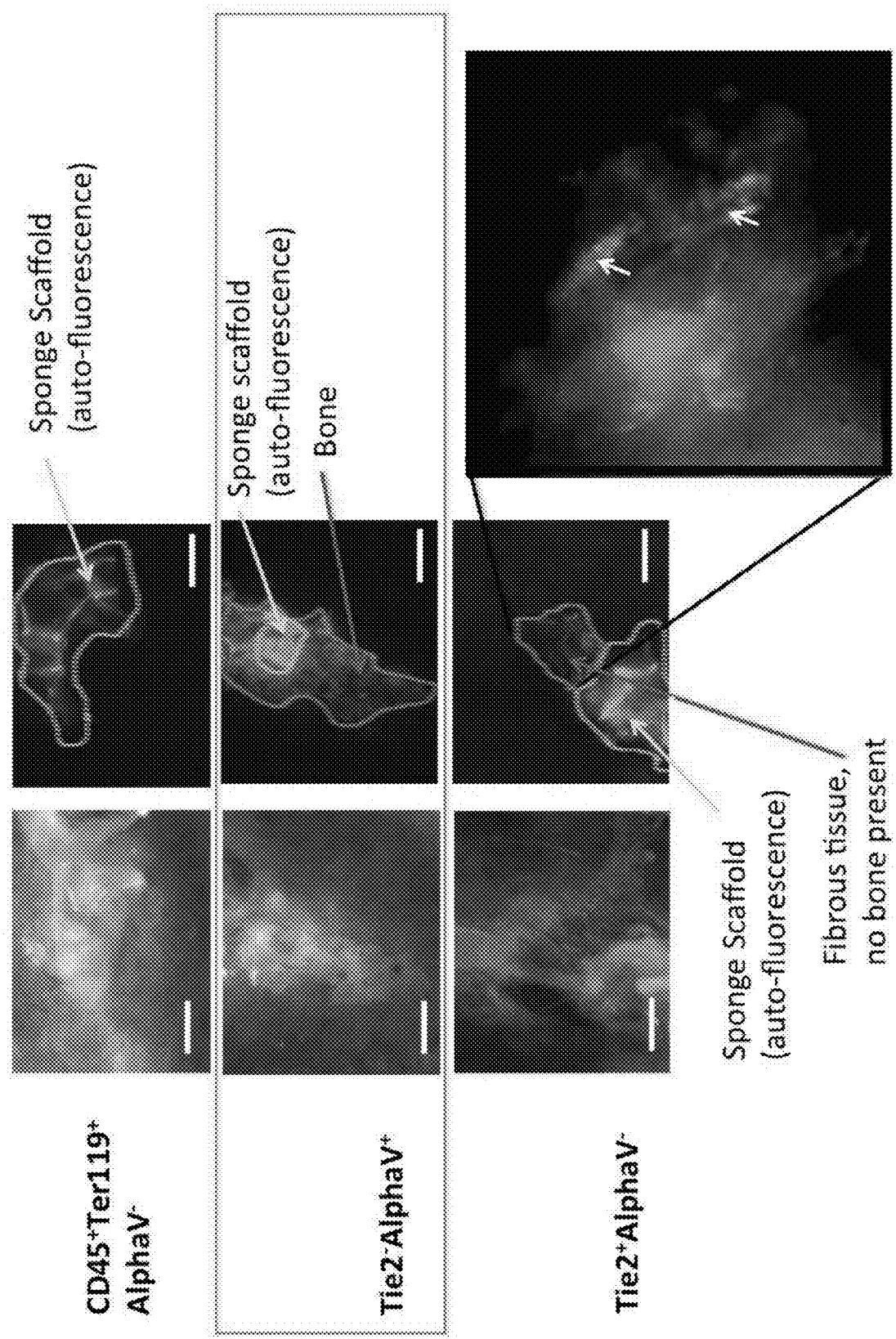

In support of the transcriptional data, the addition of exogenous recombinant BMP2 to culture media rapidly induced expansion of isolated mSSC, while supplementation of media with either exogenous recombinant TGFβ or TNFα did not (FIG. 3G, 3H). In addition, proliferation of mSSC in vitro was markedly inhibited by addition to the culture media of recombinant gremlin 2 protein, an antagonist of BMP2 signaling, in contrast to the control (FIG. 15A). Progeny of the mSSC express antagonists of the BMP2 signaling pathway, such as Gremlin 2 and Noggin (FIG. 10A, right panel), suggesting the presence of a potential negative feedback mechanism to control mSSC proliferation by more differentiated skeletal lineages. Specifically, Thy expresses Gremlin 2, and both Thy and BLSP express Noggin. Thus we speculate that Thy and BLSP subpopulations may act in a negative feedback loop to inhibit BMP-2 induced proliferation of the mSSC, further suggesting that autocrine and paracrine signaling may occur among mSSCs and their progeny can regulate their own expansion. We hypothesized that systemic endocrine regulation, as well as autocrine and paracrine regulation, may be important in regulating mSSCs and their progeny. Transcriptional expression of cognate receptors for the systemic hormones, leptin and thyroid stimulating hormone (TSH), was selectively upregulated on the mature Thy and BLSP subsets isolated from P3 mice, but not on the BCSP or the *mSSC populations (FIG. 10A). Furthermore, single cell RNA sequencing illustrated that the leptin receptor was expressed at a single cell level only on Thy/BLSP subsets isolated from P3 mice (FIG. 15E(ii)). In contrast, all of these subpopulations had minimal transcriptional expression of the corresponding ligands to these leptin or TSH receptors (FIG. 10C). These findings suggest that the downstream progeny may serve as an intermediary between the systemic endocrine signals and the mSSC (FIG. 10A, E). We found additional support for this hypothesis in that culturing Thy subsets with recombinant leptin growth hormone (1 μg/mL) was associated with upregulation of Noggin and Gremlin-2, antagonists of the BMP-2 signaling pathway (FIG. 10D). Correspondingly, conditioned media from leptin-treated Thy subsets inhibited proliferation of mSSCs (FIG. 10B). In addition, culturing Thy cells in media supplemented with recombinant leptin growth hormone (1 μg/mL) led to increased expression of gremlin 2, as observed by immunofluorescent staining (FIG. 10D(ii)-(iii)). This finding further indicates that downstream progenitors may act as a mediator between the systemic endocrine signals and the mSSC, translating endocrine to paracrine signals (FIG. 10E). Thy and 6C3 cells co-localize with and may contribute to a niche for mSSCs marked by Foxa2. As we have evidence that Thy and 6C3 subsets express components of the signaling milieu that regulate mSSC activity, we hypothesized that Thy and 6C3 subsets function not just as progeny of mSSCs but also as supportive niche cells.

To test this hypothesis we sought to determine whether Thy and 6C3 subsets co-localize with the mSSC in vivo. However this required finding a unique marker that could distinguish the mSSC from these subpopulations by immunofluorescent-histology. Thus, we used the Gene Expression Commons platform as described above and identified Foxa2 as an intracellular factor markedly expressed at highest by the mSSC, significantly lower by the CSP, but not the by any of the downstream skeletal progenitor cells (FIG. 3I), hematopoietic, or endothelial cells. Consistently, by single-cell RNA sequencing we observed that Foxa2 is significantly upregulated on the mSSC, at much lower levels in BCSPs, and almost non-existent on downstream progeny (FIG. 15F(ii)). To validate mSSC expression of Foxa2 at a protein level, we performed intracellular FACS using a specific antibody for Foxa2 in permeabilized mSSCs, which again confirmed high expression of Foxa2 by the mSSC subset (FIG. 3K). Immunofluorescent staining of femoral bone sections indicated that Foxa2+ cells are localized to the growth plates consistent with detection of mSSC in these areas by FACS analysis of dissociated tissue from these sub-regions (FIG. 1B). In the femoral growth plate, Thy and 6C3 subpopulations, stained by immunofluorescence, are localized adjacent to Foxa2+ cells, suggesting the potential role of the Thy and 6C3 subpopulations as supportive niche cells for the mSSC (FIG. 3J, L). Cartilage fates can be skewed towards bone formation. Having determined that the constituent progenitor cells of the mSSC form part of the supportive stromal niche for mSSC, we asked whether mSSC-derived stroma could influence fate commitment of the skeletal progenitor cells (FIG. 2G).

Figure 4A:
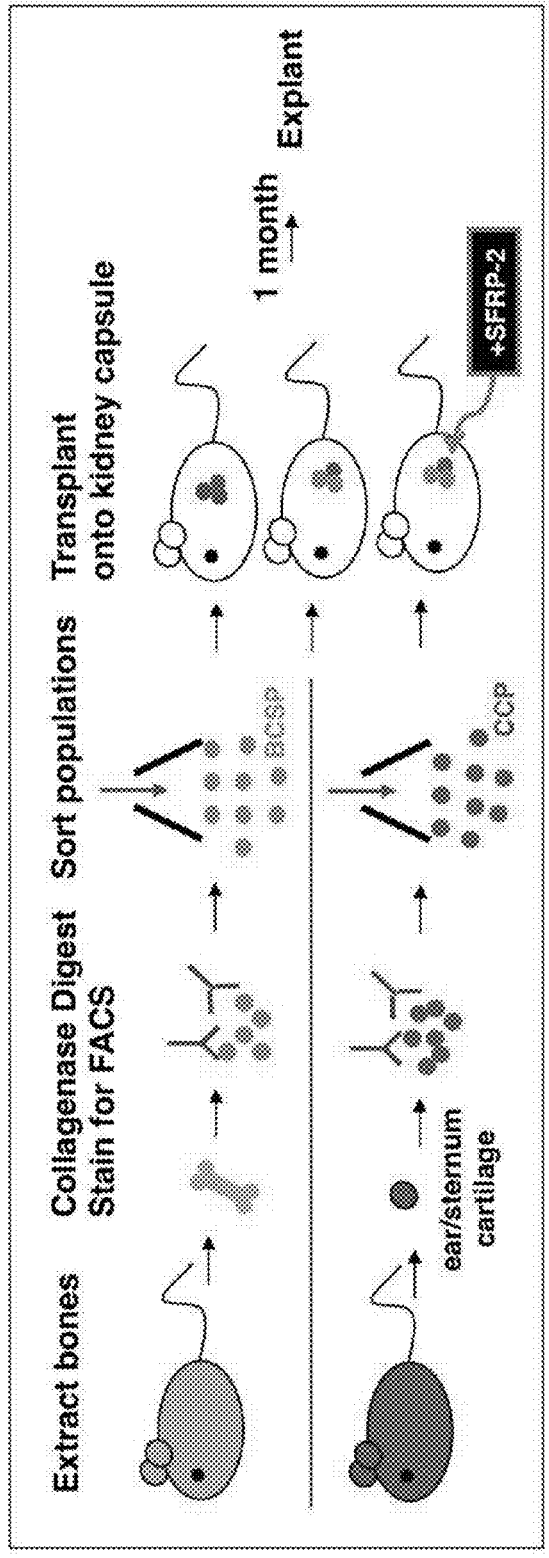
FIG. 4A-4D. Chondrocyte lineages can be induced by osteoblast lineages to undergo osteogenesis.
Figure 4D:
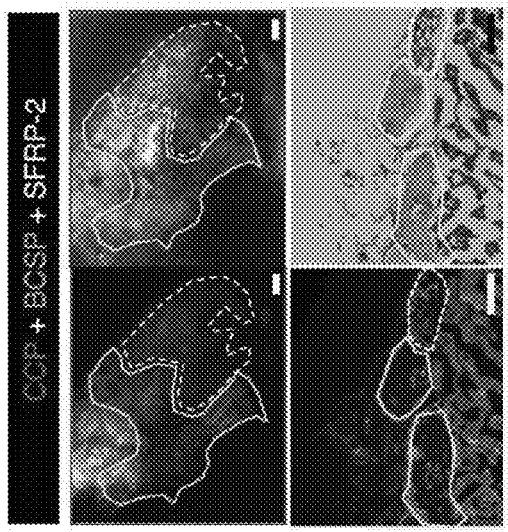
Figure 4C:
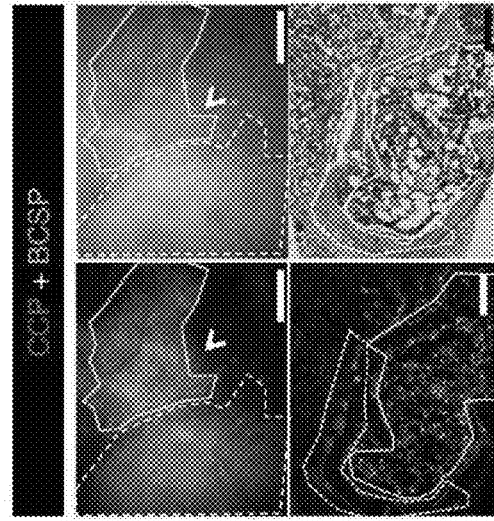
Figure 4B:
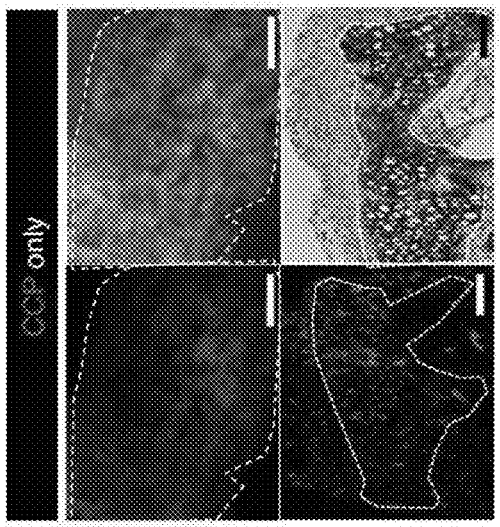

We observed that CD200(+) skeletal subsets [CD45-Ter119-AlphaV+Thy+6C3-CD105+CD200+] (FIG. 1F, population g) isolated from RFP+ mice are directed primarily towards cartilage formation when transplanted in isolation beneath the renal capsule of non-fluorescent recipient mice; thus, we designated this cell the committed cartilage progenitor (CCP) (FIGS. 4A and B). However, when RFP-labeled CCPs cells (FIG. 2G) are co-transplanted with GFP-labeled BCSPs, they differentiate into bone tissue but not cartilage (FIG. 4C). Gene expression analysis of mSSC-derived lineages (including BCSP, Thy, 6C3, BLSP and HEC) indicates that the mSSC and most of its progeny express high levels of WNT3A, WNT4 and WNT5a (FIG. 3D).

In contrast, CCPs, which when transplanted alone undergo chondrogenic differentiation, express low levels of Axin1, indicative of repressed WNT signaling. We, therefore, hypothesized that activated WNT signaling may be involved in shifting chondrogenic progenitors towards osteoblastic fates. To test this possibility, we again co-transplanted beneath the kidney capsule 20,000 RFP-labeled CCP cells with 20,000 GFP-labeled BCSPs that had local Wnt-Frizzled receptor mediated canonical WNT signal inhibited (by prior transduction with 108-109 MOI units of lentiviral vector encoding secreted frizzled-receptor-2 [SFRP-2]) (FIG. 4A). As when they were transplanted alone, the CCP cells underwent chondrogenic differentiation, repressing osteogenesis, thus indicating that the osteogenic influence by BCSP is WNT-mediated (FIG. 4D). These results suggest that gradients of WNT-related signaling activity are a possible mechanism in determining fate commitment in the skeletal progenitors (FIG. 2G).

Bone fates can be skewed towards cartilage formation by VEGF blockade. Having observed that BCSP and WNT signaling could divert cartilage fated-cells towards bone formation, we next sought to identify factors that could, conversely, selectively promote mSSCs to chondrogenic rather than bone fates. Based on the following results, we hypothesized that VEGF signaling was crucial in this fate determination. By comparing the transcriptome of purified mSSCs and that of the committed skeletal progenitors, we found that mSSCs express many key genes associated with chondrogenesis—including Runx2, Sox9, Collagen 2, and Collagen 10, suggesting that mSSCs are already primed towards a cartilaginous fate. Single-cell RNA sequencing confirmed this finding in mSSCs, showing high expression levels of Sox9 and Collagen 2 and low expression levels of Runx2 and Collagen 10. Purified mSSCs also initially form hypertrophic cartilage when transplanted, before progressing towards bone and bone marrow formation through endochondral ossification.

Emerging evidence in models of osteoarthritis indicate that dysregulation of HIF2 signaling, resulting in increased VEGF expression, can spur resting chondrocytes to re-enter a hypertrophic state and resume endochondral ossification. Treating mesenchymal stromal cells in vitro with VEGF also promotes calcification of cultured bone marrow-derived mesenchymal stromal cells and expression of early bone formation markers such as alkaline phosphatase. Thus, determined whether inhibition of VEGF signaling could promote chondrogenic differentiation of transplanted mSSCs by blocking VEGF-dependent ossification (FIG. 5A). In these experiments we used both fetal (E14.5) and post-natal mSSCs. Inclusion of the former allowed us to focus on a period of embryonic skeletal development in which VEGF signaling plays a crucial role in vascularization, enabling cartilage to become calcified to form bone. We administered $10^9$ plaque forming units (pfu) units of adenoviral vectors encoding a soluble ligand-binding ectodomain (ECD) of the VEGFR1 receptor (Ad sVEGFR1) by intravenous injection, leading to liver transduction and hepatic secretion of the soluble VEGFR1 ECD into the circulation and producing potent systemic VEGF antagonism. Adenovirus encoding a control immunoglobulin IgG2(Fc domain served as control treatment. One day later, we transplanted intact E14.5 pre-osteogenic fetal femora under the renal capsule of these mice, and then explanted the tissue 3 weeks later (FIG. 5A).

The grafts from the Ad sVEGFR1-treated mice seemed viable but appeared (grossly) pale and contained predominantly cartilaginous tissue (FIG. 5B: uppermost two panels on right; FIG. 5C). In contrast, the grafts from the control Ad Fc animals were grossly reddish in color and evidenced, on histological examination, endochondral ossification and formation of a marrow cavity surrounded by cortical bone (FIG. 5B: uppermost two panels on left; FIG. 5C). These results show that VEGF blockade can promote chondrogenesis at the expense of osteogenesis, perhaps at the level of mSSC commitment.

To test whether VEGF inhibition promotes cartilage formation at the expense of bone formation at the level of mSSC lineage commitment, we isolated mSSCs from the limbs of neonatal P3 mice, as previously described, and transplanted 20,000 of these under the renal capsule of Ad sVEGFR1-treated mice (FIG. 5A). Three weeks after transplantation, we explanted the kidneys, and performed histological analysis of sectioned mSSC-derived tissue stained with Movat's Pentachrome. Again, as in the fetal whole bone femoral transplant setting, mSSCs in the mice treated with VEGF blockade formed cartilage but not bone or marrow (FIG. 5B: lowermost two panels on right; FIG. 5C). In contrast, mSSCs transplanted into control mice underwent endochondral ossification, forming bone and marrow (FIG. 5B: lowermost two panels on left; FIG. 5C).

Given the dramatic effect of VEGF blockade on osteogenesis in both the fetal femoral and mSSC transplant assays, we were surprised to find that expression of the VEGF receptors (VEGFRs; including VEGFR1, 2, 3) and ligands VEGFA and VEGFB was extremely low to undetectable in mSSCs and their progeny (BCSP, Thy, 6C3, BLSP, HEC subsets) (FIG. 5D: panel on left). However, VEGFC was expressed at high levels in the progenitor subpopulations (FIG. 5D: panel on left). In addition, mSSC and its derivative lineages express high levels of neuropilin 1 and 2, which function as receptors for some forms of VEGF, including Placental Growth Factor (PlGF) and soluble VEGFR1 antagonizes the activation of NRP1 by PlGF (FIG. 5D: panel on right). Therefore, VEGF blockade may affect mSSCs and their progeny (resulting in cartilage formation instead of bone) (FIG. 5A-C), through NRP1 antagonism instead of direct inhibition of VEGF signaling.

Figure 5E:
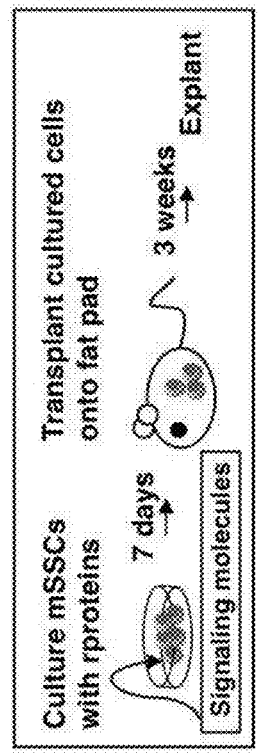
Figure 5F:
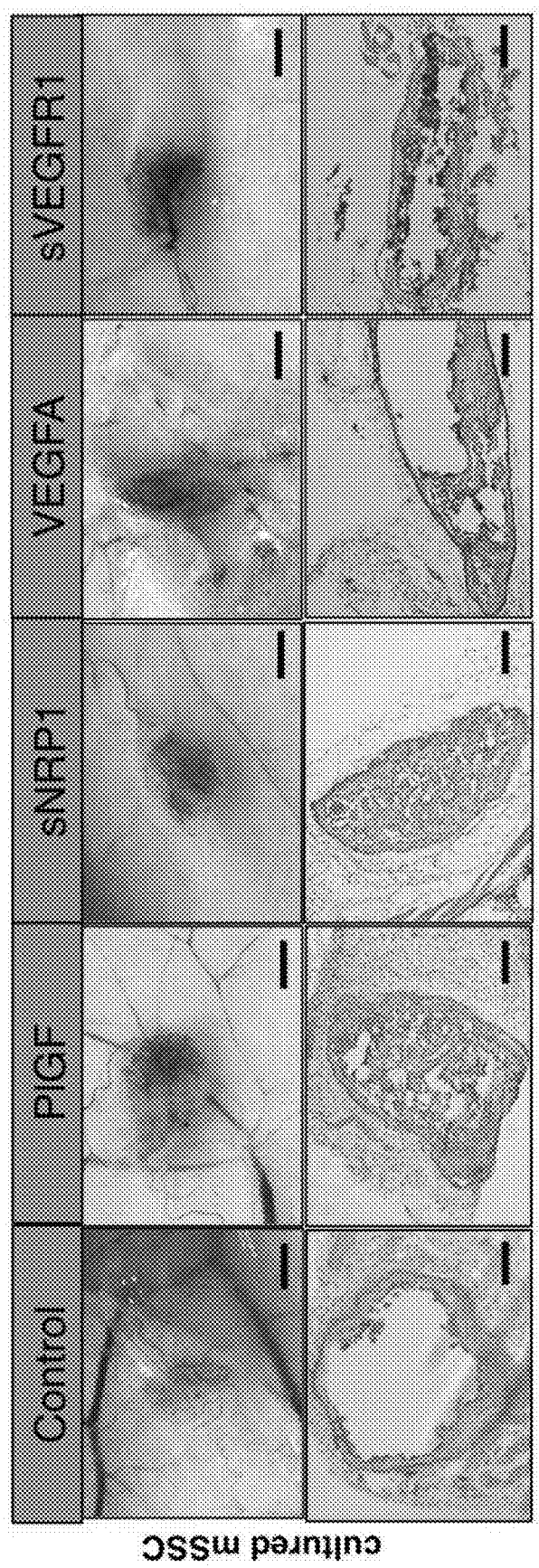

As systemic VEGF blockade dramatically stimulates chondrogenesis in transplanted fetal anlage and mSSC, we questioned whether chondrogenesis is mediated by an indirect or direct effect of VEGF antagonism in the mSSC. Thus, we explored which fate was promoted (cartilage or bone formation) following (direct) exogenous activation or inactivation of NRP1/VEGFR1. We plated freshly isolated mSSCs from GFP-labeled mice for in vitro treatment with sVEGFR1-Fc fusion protein (5 µg/mL), soluble NRP1 ectodomain (2.5 µg/mL) and PlGF (0.5 µg/mL). After one week of treatment in vitro, we transplanted 20,000 mSSCs beneath the renal capsule of immunodeficient mice (FIG. 5E). Three weeks after transplantation, we explanted the grafts and noted that neither agonism nor antagonism of in vitro VEGF and PlGF signaling significantly altered mSSC potential to differentiate into bone in vivo, indicating that the mechanism of VEGFR antagonism resulting in chondrogenic fate promotion occurs indirectly through the environment, rather than a direct effect on the mSSC (FIG. 5F).

We next questioned whether promotion of chondrogenesis might occur following activation or inhibition of TGFβ signaling, which is reported to be involved in postnatal endochondral bone formation. We isolated mSSCs from GFP-labeled mice by mechanical and enzymatic dissociation and subsequent FACS. We then plated these cells in the presence of either TGFβ (250 ng/mL) or conversely soluble TGFβ receptor (5 µg/mL) for one week prior to transplantation beneath the renal capsule of immunodeficient mice. Three weeks after transplantation, these grafts were explanted for histological analysis. Following direct inhibition of TGFβ, we found that these grafts formed cartilage and little bone, reflecting that direct antagonism of TGFβ signaling results in cartilage fate promotion in the mSSC.

Manipulation of the BMP pathway can induce de novo formation of the mSSC in extraskeletal locations. Since we established that bone, cartilage and stromal populations in skeletal tissue are derived from mSSCs and their progeny, we next investigated whether other tissue types contain cells that are osteo-inducible or harbor dormant mSSCs that can be activated to undergo osteogenesis. We tested BMP2 as an agent that may induce such osteogenesis. Although the osteogenic properties of BMP2 are known and it is approved in clinical orthopedic procedures to stimulate osteogenesis, the biological mechanism underlying BMP2 mediated osteogenic induction has not been determined. We observed that BMP2 can expand mSSC in vitro, as detailed above (FIG. 3G, H).

Figure 6B:
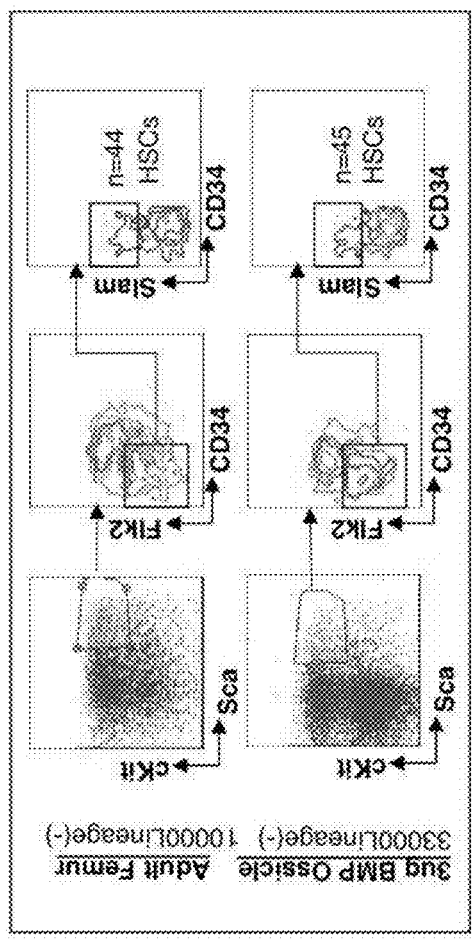
FIG. 6A-6F. Manipulation of the BMP pathway can induce de novo formation of the mSSC in extraskeletal regions.
Figure 6A:
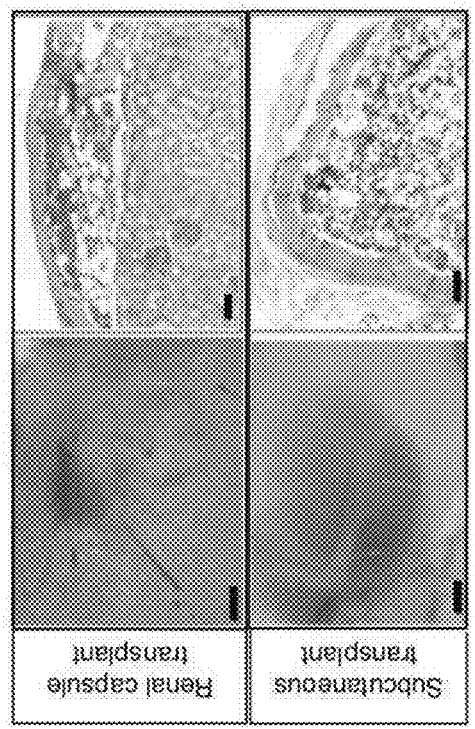
Figure 6C:
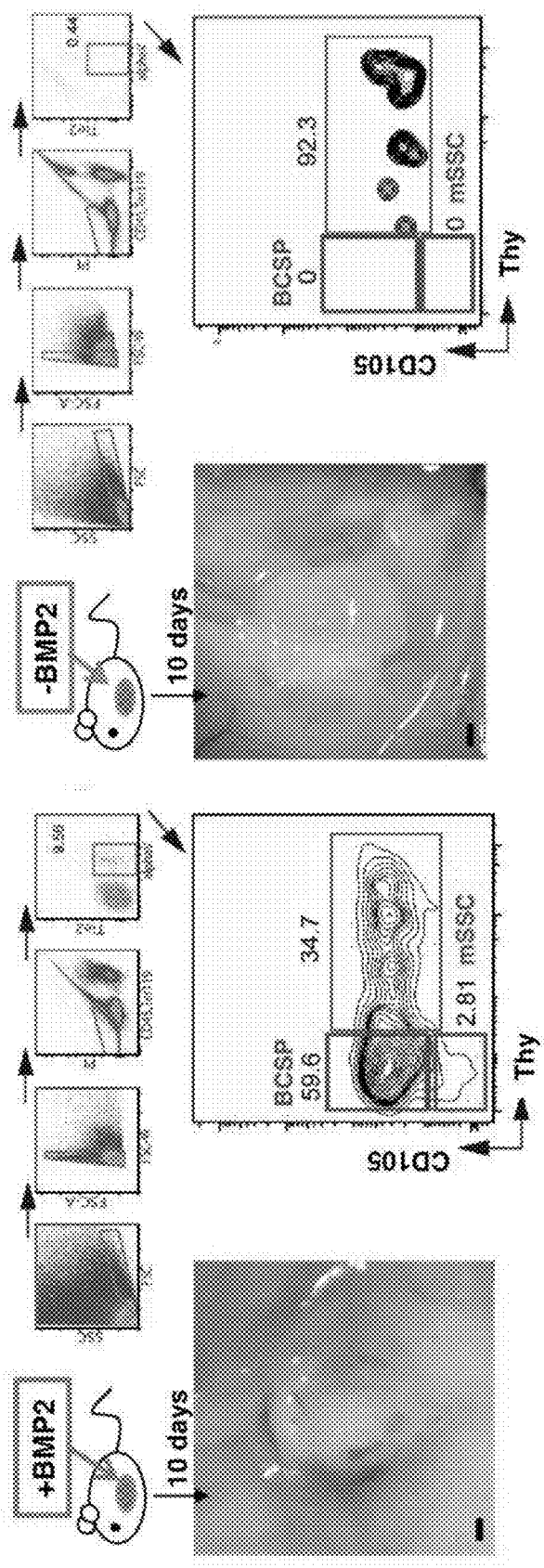

To better understand the osteogenic effect of BMP2, we placed collagen sponges containing 3 µg of lyophilized recombinant BMP2 into extraskeletal sites, either subcutaneously into the inguinal fat-pad or under the renal capsule. Harvest of the collagen sponges 4 weeks after placement revealed abundant osseous osteoids replete with marrow from the sites in the kidney and subcutaneous tissue (FIG. 6A-C). Furthermore, FACS analysis of cells within the marrow of the osteoids revealed a frequency of HSCs (FIG. 6B, bottom row) similar to that found in "normal" adult femurs (FIG. 6B, top row). These data show that BMP2-induced bones are functionally similar to normal bones (FIG. 6B). By FACS analysis we determined that mSSC are normally not detectable or are exceedingly rare in subcutaneous adipose tissue (FIG. 6C: right panel). In contrast, mSSC are found in high numbers in BMP2-induced osteoids 10 days after implantation, while ossification is still proceeding (FIG. 6C, left panel).

Figure 6D:
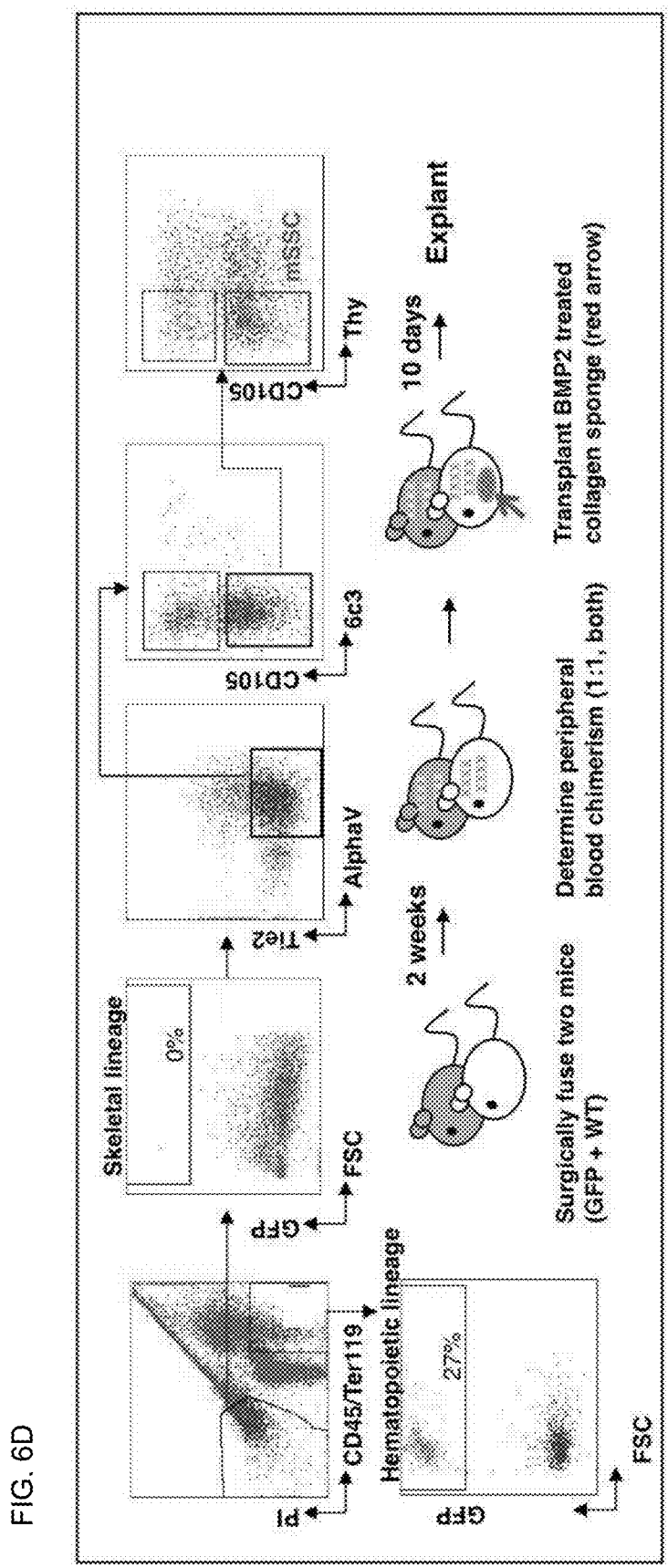

As we had established that mSSC and downstream skeletal progenitors are exceedingly rare in "normal" subcutaneous adipose tissue, we questioned the origin of the skeletal progenitors contributing to BMP2-induced ectopic bone formation. To determine whether BMP2 induced skeletal transformation of in situ cells or the migration of circulating skeletal progenitors recruited from bone tissue, we used a parabiont model (FIG. 6D). We surgically fused actin-GFP transgenic mice to non-GFP congenic mice such that they established a shared circulatory system by vessel sprouting and anastomosis in the joined regions. Two weeks after parabiosis, after a common circulation between parabionts had been confirmed by FACS analysis, collagen sponges containing 3 pg of lyophilized recombinant BMP2 (as described above) were placed in the inguinal fat pad of the non-GFP parabiont. Ten days after implantation, we explanted the sponge and surrounding tissue and performed mechanical and chemical dissociation to isolate the constituent cell populations.

We assayed the contribution of the GFP-labeled cells to ectopic bone formation in the non-GFP mouse by FACs analysis, to determine whether circulating cells contributed to the development of ectopic bone. The tissue of the explants contained abundant GFP-labeled cells at harvest, but FACS analysis revealed that the GFP-labeled cells in the graft were solely CD45(+) hematopoietic cells (FIG. 6D, left panel, top and bottom), and not skeletal progenitors (FIG. 6D, FACS plots, mSSC cell population shown on far right). The skeletal progenitor population present in the explanted tissue was entirely GFP-negative, suggesting that circulating skeletal progenitor cells did not contribute to BMP2-induced ectopic bones (FIG. 6D, FACS plots, mSSC cell population shown on far right).

Figure 6E:
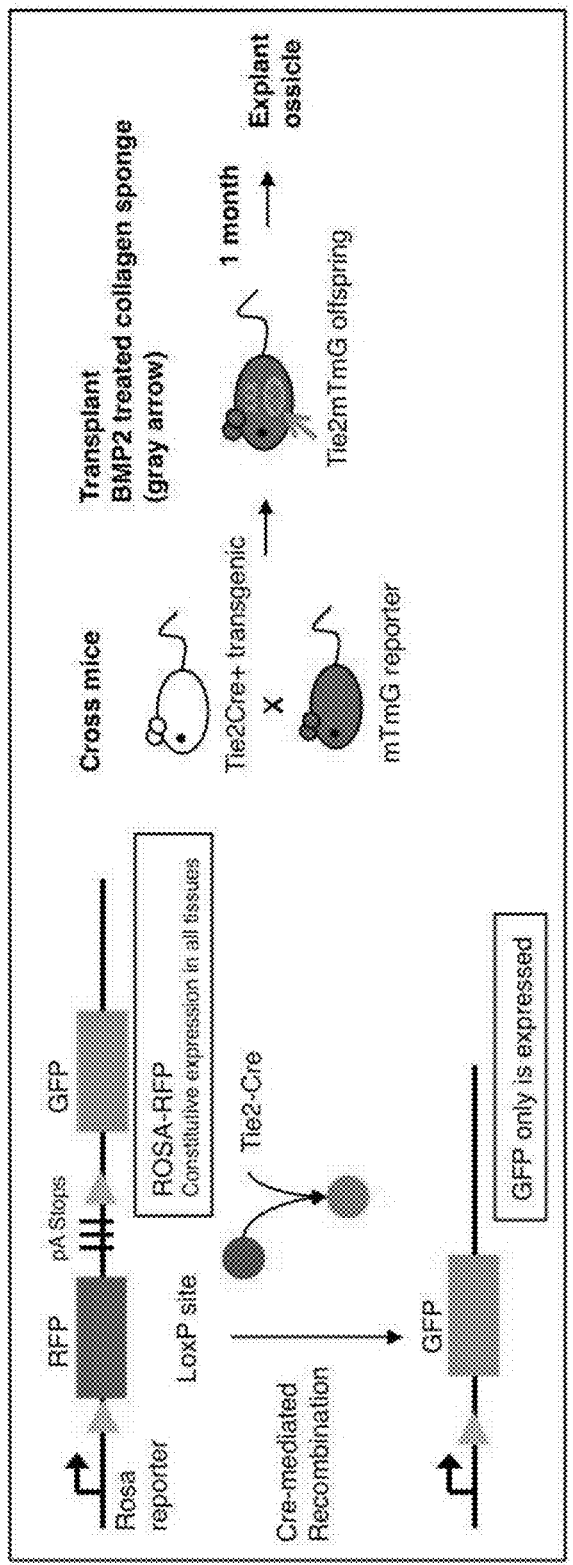
Figure 6F:
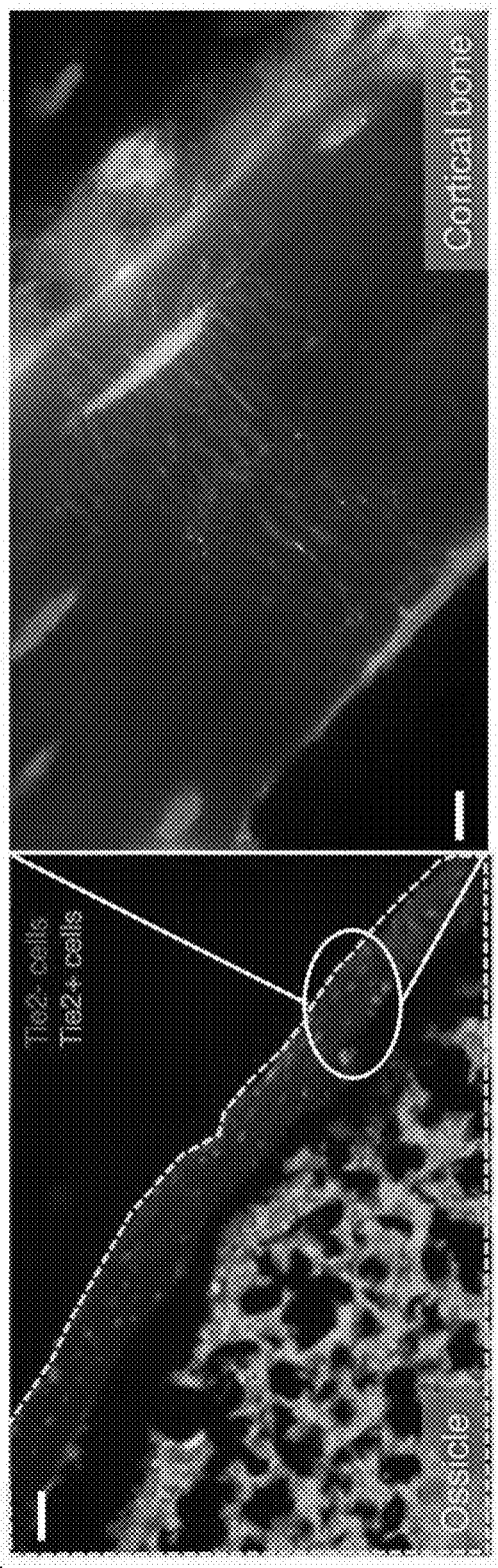

These data indicate that BMP2-induced osteogenesis involves local cell response that is sufficient to induce formation of primitive mSSC skeletal progenitors in the subcutaneous fat pads, leading to formation of ectopic bone that can support hematopoiesis. As we had established that BMP2 could induce ectopic bone formation both subcutaneously and beneath the renal capsule, we wished to determine which cell types could undergo BMP2-mediated reprogramming to mSSC in these extraskeletal sites. We, therefore, conducted FACS analysis of suspended cells isolated from the kidney and the subcutaneous adipose tissue and looked for markers that could distinguish cell types common to both of these extraskeletal organs. We found that both kidney and adipose tissue contain high numbers of Tie2 and PDGFRα-expressing cells. Tie2 expression has been detected in endothelial, pericyte and hematopoietic stem cell subsets, while PDGFR(is expressed in various tissues. Using a specific Tie2Cre x MTMG reporter mouse, which genetically labels cells that express Tie2 with GFP and other cells with RFP, we again inserted collagen sponges containing 3 µg of lyophilized recombinant BMP2 into the inguinal fat pad and harvested the implanted tissue at 32 days later (FIG. 6E). FACS analysis revealed that BMP2-derived ossicles clearly incorporated both GFP-positive Tie2-derived osteocytes with visible canaliculi (FIG. 6F, high magnification inset) and Tie2-negative RFP-labeled osteocytes (FIG. 6F). This finding suggests that both Tie2-positive and Tie2-negative BM P2-induced skeletal reprogramming. Consistent with these observations, subcutaneous Tie2(+)PDGFR((+) and Tie2(-)PDGFR((+) cells expressed high levels of BMPR1a, which is a primary receptor for BMP2 signaling (FIG. 7D).

These data suggest that a variety of cell types could be induced by BMP2 to initiate formation of mSSC. Co-delivery of BMP2 and VEGF inhibitor is sufficient to induce de novo formation of articular cartilage in adipose tissue. While bone itself possesses regenerative ability, the capacity for regeneration in other types of skeletal tissues, such as cartilage, is very low. As described above, VEGF blockade indirectly stimulates mSSCs to form cartilage (FIG. 5 A-C). As BMP2 induction could stimulate mSSC expansion and formation (FIG. 3G-H, FIG. 6C), we speculated that the mSSC inducing capacity of BMP2 could be coupled with VEGF blockade to direct de novo cartilage formation.

Figure 7A:
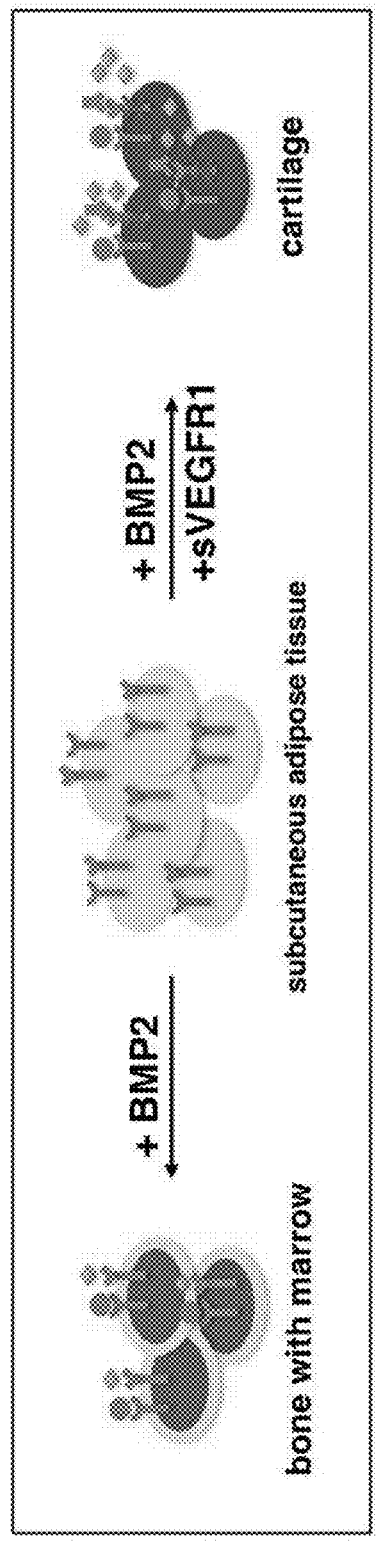
FIG. 7A-7E. Co-delivery of BMP2 and VEGF inhibitor is sufficient to induce de novo formation of cartilage in adipose tissue.
Figure 7B:
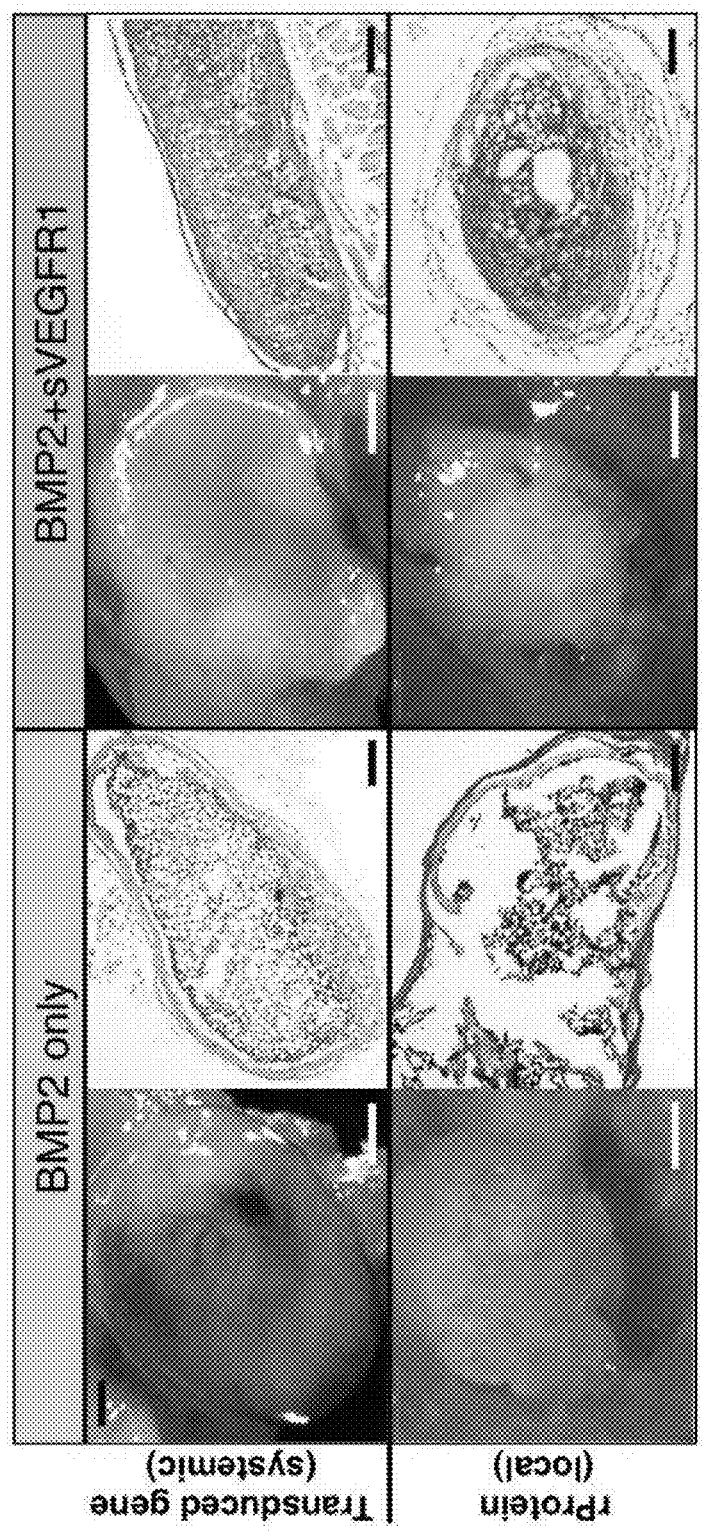
Figures 7C, 7D, 7E:
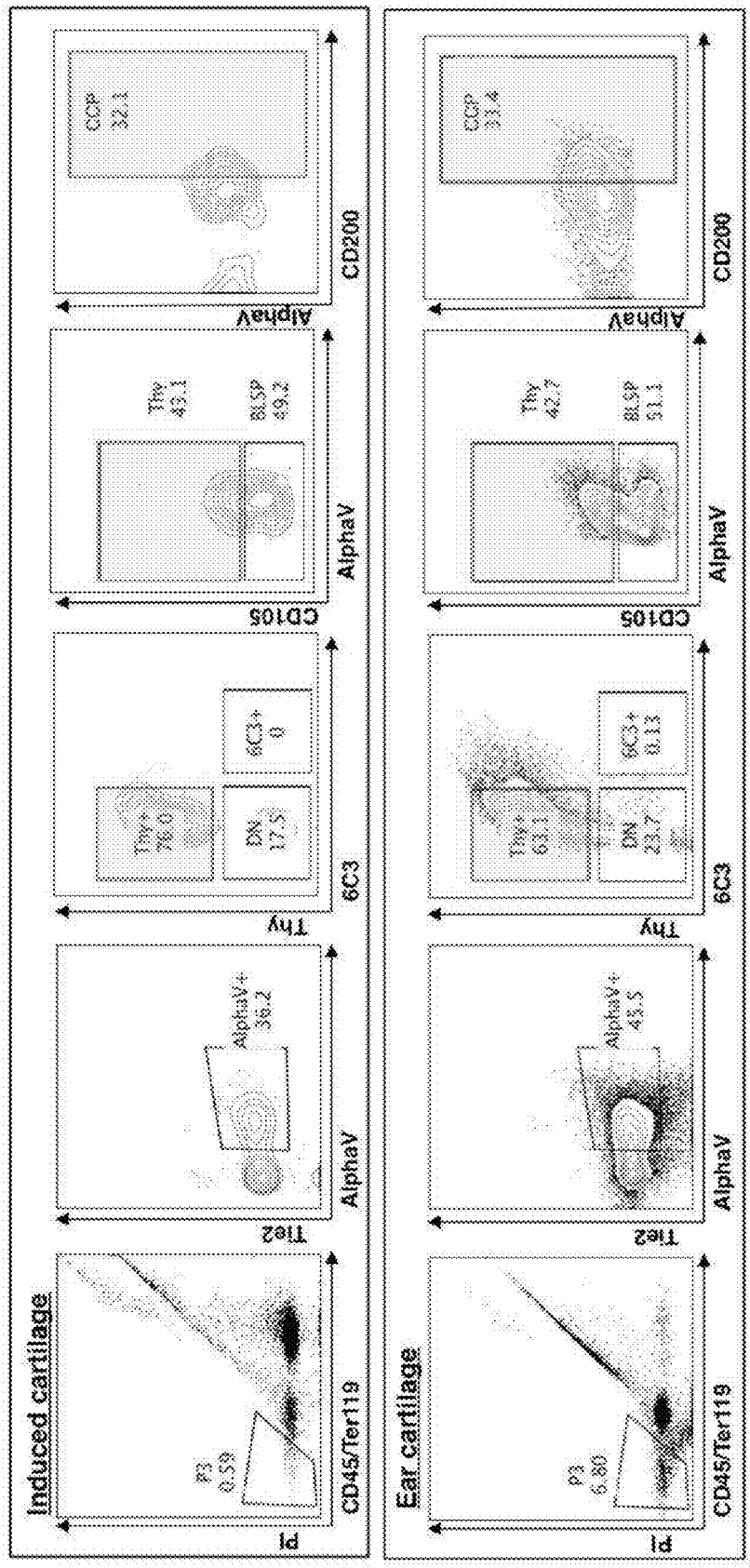

To test this possibility, we implanted BMP2-treated collagen sponges into the adipose tissue of mice that had been treated 24 hours earlier with either intravenous delivery of Ad sVEGFR1 as in FIG. 5, or included soluble VEGFR1 ECD (50 pg) directly in the collagen sponge (FIG. 7A). One month later the sponge and surrounding tissue were explanted. BMP2 alone generated bone tissue with hematopoietic activity (FIG. 7B: left panel). However, BMP2 with either systemic or local VEGF inhibition resulted in predominant cartilage formation (FIG. 7B: right panel). Like natural cartilage in the mouse ear, this induced cartilage contained a high frequency of CCPs as detected by FACS (FIG. 7C). This cartilage likely derives from de novo reprogramming of adipose tissue into chondrogenic fates since native adipose tissue normally express very low to undetectable levels of genes associated with chondrogenesis, such as Sox9 or Runx2 (FIG. 7E).

The genetic pathways necessary for maintenance of post-embryonic stem/progenitors of skeletal tissues and how they are coordinated at stem cell level to maintain skeletal patterning during skeletal growth and regeneration are poorly understood. To complicate things further, considerable uncertainty remains regarding the origins and identities of skeletal progenitors and their lineal relationship to a prototypical mesenchymal stem cell, which has been proposed as a ubiquitous progenitor for diverse mesenchymal tissue types, including bone, muscle, cartilage and fat. Using a transgenic "Rainbow mouse" model for in vivo genetic tracing of clonally derived tissues, we found that bone, cartilage, and stromal tissues are indeed clonally related. Conversely, we found little evidence that they share the same clonal origins as fat, vessel, or skeletal muscle tissue, implying that these tissues likely arise from their own distinct stem/progenitor cells following embryogenesis.

Identifying postnatal skeletal stem/progenitor cells and defining the skeletal stem cell lineage tree. After identifying the existence of clonal populations giving rise to skeletal (bone, cartilage and stromal) tissue, we compiled a lineage map of prospectively isolated stem/progenitor cells with skeletogenic potential to help resolve the uncertainty regarding lineage relationships among skeletal stem and progenitor cells (FIG. 2G). This lineage map consists of eight different cellular subpopulations with distinct skeletogenic properties. Some of these subpopulations have characteristics of recently described skeletogenic cell types that were identified by genetic lineage tracing (see Park et al. (2012) Cell stem cell 10, 259-272; Mendez-Ferrer et al. (1998) Radiographics: a review publication of the Radiological Society of North America, Inc 18, 1125-1136; Zhou et al. (2014) Cell stem cell 15, 154-168).

For instance, the Thy subtype selectively expresses high levels of CXCL12, leptin receptor, and nestin, which are characteristics of CXCL12-abundant reticular cells, leptin receptor-expressing cells (LepR+), and Nestin-expressing mesenchymal stem cells, respectively. In contrast to the recent report that LepR+ cells in the adult bone marrow are the major source of bone and adipose tissue postnatally, our results indicate that neonatal mSSCs do not express LepR. Furthermore, we note that the mSSC and its progeny give rise to only skeletal but not adipose tissue. We also find that both Nestin-cre and MX1-cre labeled populations overlap with the mSSC population.

This work represents the first report of a postnatal skeletal stem cell and its downstream progenitors. Mechanistically, mSSC expansion and self renewal must be tightly controlled, evinced by the expression of numerous cognate receptors to signaling molecules belonging to most of the known signaling pathways including Hedgehog, BMP, FGF, TGF, Notch, etc. BMP2 in particular is sufficient to expand mSSC in culture. Both BMP2 and 4 are expressed by mSSCs and most mSSC-derived subsets, where they likely mediate survival and expansion via both autocrine and paracrine loops. Conversely, downstream progeny of mSSCs such as Thy and BLSP populations also express noggin and/or gremlin-2, which antagonize BMP signaling. This suggests that mSSCs and some of their progeny form a portion of their own niche, maintaining critical levels of pro-survival factors such as BMP2 but also keeping skeletal growth in check by antagonizing BMP signaling. These inhibitory signals may be repressed following injury, for instance we observe that there is notable amplification of SSC number following induced femoral fracture, which is most marked in the early stages of fracture healing.

Directing mSSC fate determination from bone to cartilage. Antagonistic signaling between mSSC-derived skeletal subsets also appears to be a key mechanism in lineage commitment of skeletal subsets, particularly to either a bone or cartilage fate. When we antagonized VEGF signaling in early skeletal progenitors, bone fates were inhibited in favor of cartilage fates. Yet, we did not observe significant expression of VEGF or VEGF receptors in mSSCs or downstream skeletal subsets. Instead, we see that they express the VEGF and VEGFR homologues PlGF and neuropilin, respectively.

Directing skeletal progenitor fate determination from cartilage to bone WNT signaling may also play a role in determining bone vs. cartilage formation, specifically in favoring bone. Altering WNT signaling in a particular subpopulation can direct the skeletal fate of other subpopulations in the microenvironment. For example, we find evidence that WNT signaling in BCSPs that were co-transplanted with CCPs (i.e., committed cartilage progenitors), caused the latter to form bone rather than cartilage when placed under the renal capsule. Cartilage fates may be promoted by WNT antagonism and that this could be mediated by the mSSC, BCSP and 6C3+ subpopulations, which express high levels of SFRP-2, an endogenous antagonist of canonical WNT signaling (FIG. 3D).

Pathological conditions involving calcification of cartilaginous tissues, such as osteoarthritis, could stem from defects in the mSSC niche, possibly due to activation of WNT signaling and resultant promotion of osteogenesis.

We conducted gene expression analysis of multiple highly purified hematopoietic stem and progenitor subsets including HSCs, and the committed progenitors of major hematopoietic lineages and found that hematopoietic progenitors express myriad factors associated with skeletogenesis, including BMP2, BMP7, TGFb1, and Wnt3a (Table 1).

TABLE 1

Expression of hematopoietic factors by skeletal progenitors*

| Cytokines | Progenitor type (expression level) |
|---|---|
| Kitl | Thy (5) |
| SDF | Thy (5), 6C3 (3), BLSP (3), HEC (3) |
| IL-3 | BLSP (7), HEC (5) |
| IL-9 | BLSP (9), HEC (6), mSSC/pre-BCSP (5), 6C3 (3), Thy (2) |
| IL-11 | BCSP (5), mSSC/pre-BCSP (3) |
| IL-16 | 6C3 (2), HEC (2) |
| IL-17b | mSSC/pre-BCSP (8), BLSP (4), BCSP (4), HEC (2) |
| IL-25 | BLSP (4), HEC (3) |
| IL-33 | Thy (7), BLSP (3), HEC (2) |
| MCSF/CSF1 | BLSP (5) |

*Numbers in parentheses represent level of expression on a scale of 1-10 where 10 is the highest level.

The cognate receptors of these factors are highly expressed by mSSCs and skeletal derived progenitors (FIG. 3D-E). Intriguingly, while mSSC-generated progeny, such as Thy and BLSP, selectively express receptors to circulating systemic hormones, such as leptin, testosterone, ghrelin and thyroid-stimulating hormone, these receptors are not highly expressed in HSCs or hematopoietic subsets (Table 2).

TABLE 2

Expression of skeletalgenic factors by hematopoietic progenitors*

| Morphogen/receptor | Progenitor type (expression level) |
|---|---|
| BMP2 | iNK (2) |
| BMP7 | iNK (7) |
| Tgfb1 | CLP (6), BLP (5), Monocyte (4), MKP (3), iNK (2) |
| Wnt1 | MKP (3) |
| Wnt3a | MKP (7) |
| Fdz5 | iNK (8), MEP (3), HSC (2) |
| Fdz7 | MPP (3), MEP (3), CMP (3), GMP (2), HSC (2) |
| Fgf3 | MPP (8), CMP (8), MEP (7), GMP (3) |
| Shh | MKP (7) |
| Lepr | HSC (0), CMP (0), CLP (0), BLP (0), GMP (0), MEP (0), MKP (0), MPP (0), iNK (0) |
| Gremr | HSC (0), CMP (0), CLP (0), BLP (0), GMP (0), MEP (0), MKP (0), MPP (0), iNK (0) |
| Ar | HSC (0), CMP (0), CLP (0), BLP (0), GMP (0), MEP (0), MKP (0), MPP (0), iNK (0) |
| Tshr | HSC (0), CMP (0), CLP (0), BLP (0), GMP (0), MEP (0), MKP (0), MPP (0), iNK (0) |

*Numbers in parentheses represent level of expression on a scale of 1-10 where 10 is the highest level.
BLP: B Lymphoid Progenitor
CLP: Common Lymphoid Progenitor
CMP: Common Myeloid Progenitor
GMP: Granulocyte Macrophage Progenitor
HSC: Hematopoietic Stem Cell
iNK: Natural Killer Cell Progenitor
MEP: Megakaryocyte erythroid Progenitor
MKP: Megakaryocyte Specific Progenitor
MPP: Multipotent Hematopoietic Progenitor Thus, we mSSC-derived stromal cells constitute a cellular interface linking systemic endocrine regulation to both the skeletal and hematopoietic system.

Figure 14F:
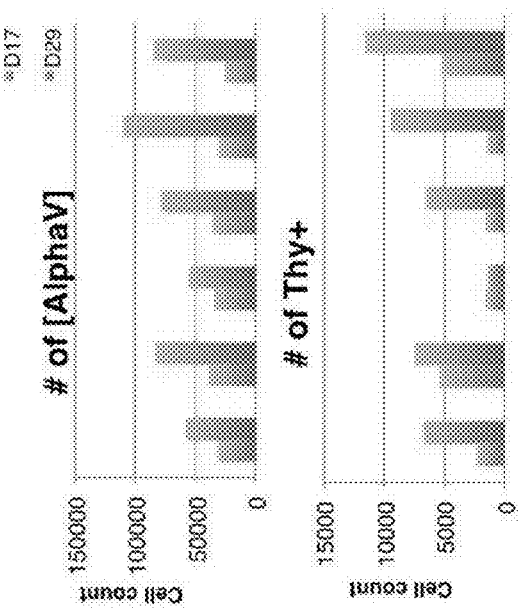
Figure 14D:
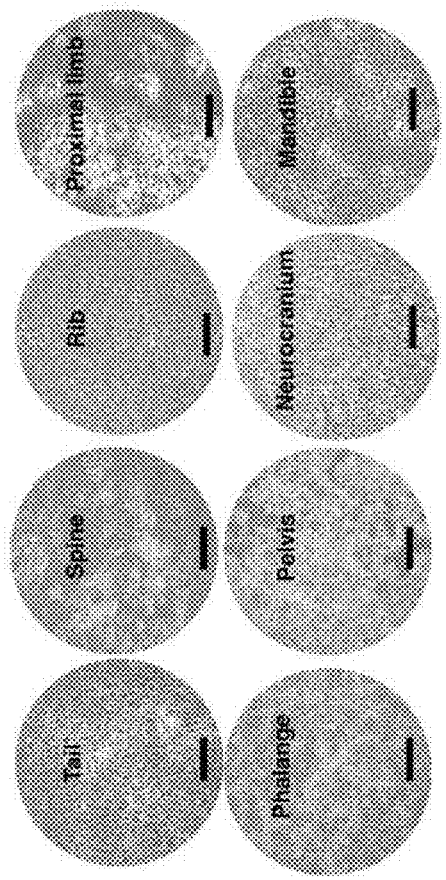
Figure 14E:
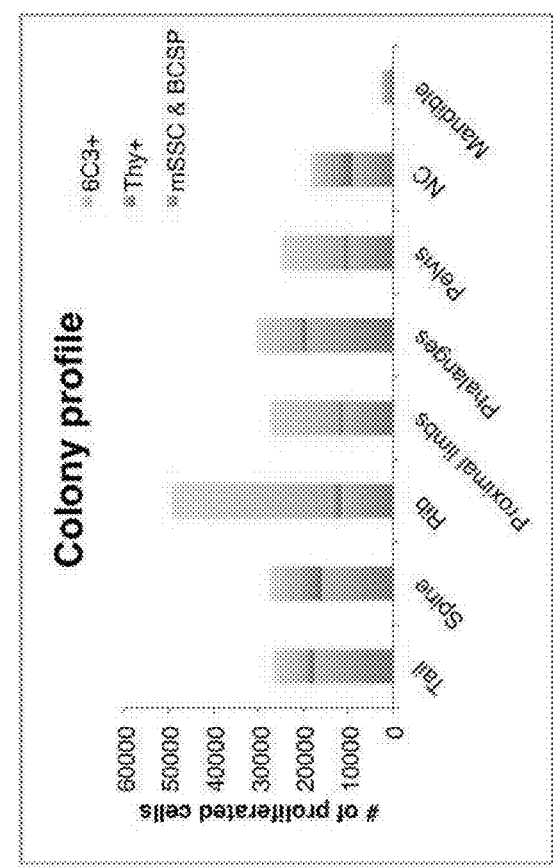

Activity and fate determination of the mSSC depends on the skeletal origin. Our analyses have established a framework for interrogating the genetic circuitry guiding postnatal skeletal development at the stem cell level. mSSC are tasked with maintaining the shape of the skeletal system during growth and its recovery after injury. Differences in mSSC activity may underlie the many differences in skeletal shapes. In agreement with this possibility, we find that mSSC are functionally heterogeneous, and there are substantial differences in the mSSC frequency, colony forming potential, and lineage potential depending on the types of bones from which they were harvested (FIG. 14).

Altering extra-skeletal niche signaling to induce osteogenesis and chondrogenesis. Since most organs are composites of multiple tissue types, the stem cell niche may coordinate the activity of different tissue-specific resident progenitors. Modulating niche signaling can stimulate tissue growth by inducing proliferation of stem cells, as we have now observed with skeletal stem cells and has been described in the hematopoietic system. Niche interactions may also play significant roles in maintaining lineage commitment, for instance, high levels of BMP2 signaling can dominate local adipose microenvironment signaling and re-specify resident Tie2(+) and Tie2(−) subsets to undergo osteogenesis. Niche interactions can also determine the fate of the mSSC. By implanting BMP2-treated collagen sponges in concert with systemic or local application of soluble VEGF receptor, we demonstrate that cartilage can be induced to form entirely by manipulation of local signaling pathways in extraskeletal tissue.

Inducing mSSC formation with soluble factors and subsequently regulating the mSSC niche to control its differentiation towards bone, cartilage, or stromal cells represents a paradigm shift in the therapeutic regeneration of skeletal tissues. This therapeutic modality can also extend to the co-dependent hematopoietic system even when resident levels of endogenous mSSCs have been depleted by disease or aging.

Experimental Procedures. All experiments were performed in triplicate, unless otherwise stated. Animal experiments included a cohort of at least three animals in each experimental group and, at least, three control subjects. For transplant experiments, 7-10 P3 mice were harvested for each mSSC/progenitor transplant (e.g., 7-10 mice were harvested to obtain 20,000 stem/progenitor cells for subsequent transplantation as detailed below).

Mice. Mice were maintained in Stanford University Laboratory Animal Facility in accordance with Stanford Animal Care and Use Committee and National Institutes of Health guidelines. C57BL/Ka-Thy1.1-CD45.1 (HZ), C57BL/Ka-Thy1.1-CD45.1 (BA), C57BL/Ka-Thy1.2-CD45.1 (Ly5.2) and C57BL/Ka-Thy1.2-CD45.1 (B6), Rag-2/gamma(c)KO, C57BL/6-Tg(CAGEGFP) 1Osb/J, Mx1Cre were derived and maintained in our laboratory. Rosa-Tomato Red RFP and Tie2Cre mice were obtained from Jackson Labs and a breeding colony was established. mTmG mice were a gift from Liqun Luo. Mice were housed in sterile micro-insulators and given water and rodent chow ad libitum.

Rainbow mouse system. We utilized a "Rainbow mouse" model as a way to evaluate clonal lineage relationships in vivo to determine if mesenchymal tissues in bone, including stroma, fat, bone, cartilage, and muscle share a common progenitor. The Rainbow reporter (R26VT2/GK3) mouse, which enables us to trace individual cells of skeletal tissue in limbs in vivo over long periods of time, is a multicolor Cre-dependent marker system that harbors a four-color (green, blue, yellow, red) reporter construct within the ROSA locus. After recombination, each cell is randomly and permanently (genetically) marked with one of four colors, resulting in a mosaic fluorescent pattern within tissues. Daughter cells maintain the same color as the cell of origin, such that products of clonal divisions can be visualized as expanding regions of a single color. Rainbow mice were crossed with the ubiquitous ActinCreER driver so as to universally mark, and clonally trace, all cells within skeletal tissues after administration of tamoxifen. Despite the chance of two adjacent cells being similarly colored, our laboratory and other groups have found that lineage tracing over long periods of time uncovers a faithful cellular readout to that observed using tissue-specific or stem cell-specific reporters. Furthermore, as this assay can be used broadly to trace all cell types, it allows clonal analysis of even rare and as-yet-unidentified tissue stem cells that may be activated during embryonic/postnatal development that would not be uncovered using existing stem cell reporters.

In order to accurately count the clones, we utilized the Image J software analysis platform (National Institute of Health, Bethesda). Fluorescence-activated cell sorting (FACS) Flow Cytometry was performed on FACS Aria II in the Shared FACS Facility in the Lokey Stem Cell Institute, details of the sorting profile are detailed below and illustrated in FIG. 1B, FIG. 1E, FIG. 6B, FIG. 6D, FIG. 7C and FIG. 13.

Isolation and transplantation of adult and fetal skeletal progenitors. Skeletal tissues were dissected from P3 GFP-labeled mice and dissociated by mechanical and enzymatic dissociation. Specifically, the tissue was placed in collagenase digestion buffer supplemented with DNase and incubated at 37° C. for 40 minutes under constant agitation. After collagenase digestion and neutralization, undigested materials were gently triturated by repeated pipetting. Total dissociated cells were filtered through 40 m nylon mesh, pelleted at 200 g at 4° C., resuspended in staining media (2% fetal calf serum in PBS), blocked with rat IgG and stained with fluorochrome-conjugated antibodies against CD45, Tie2, AlphaV integrin, CD105, Thy1.1, Thy 1.2, 6C3 and CD200 for fractionation by fluorescence activated-cell sorting.

Sorted and unsorted skeletal progenitors were pelleted, resuspended in 2 ml of matrigel, then injected underneath the renal capsule of 8-12 week old anesthetized immuno-compromised Rag-2/gamma(c)KO mice. Bones of GFP-labeled 6-week old adult mice were dissected, gently crushed by mortar and pestle, and subsequently digested in collagenase buffer with DNase at 37° C. for 40 minutes under constant agitation. After collagenase treatment, undigested materials were gently triturated by repeated pipetting. Total dissociated cells were filtered through 40 μm nylon mesh, pelleted at 200 g at 4° C., resuspended in staining media (2% fetal calf serum in PBS), blocked with rat IgG and stained with fluorochrome-conjugated antibodies against CD45 (Biolegend, San Diego, Calif.), Tie2 (eBioscience, San Diego, Calif.), AlphaV integrin (eBioscience, San Diego, Calif.), CD105 (eBioscience, San Diego, Calif.), Thy1.1 (eBioscience, San Diego, Calif.), Thy 1.2 (eBioscience), 6C3 (Biolegend, San Diego, Calif.) and CD200 (Biolegend, San Diego, Calif.) for purification by flow cytometry sorting.

CCPs for BCSP cotransplantation experiments were isolated from the sternum and ear where they are present in the highest frequencies. CD200 was used to enrich for CCPs for the majority of these experiments. Sorted and unsorted skeletal progenitors were pelleted and resuspended in 2 ml of matrigel, then injected underneath the renal capsule of 8-12 week old anesthetized Rag-2/gamma(c)KO mice. In initial experiments, we noted that the earliest skeletogenic population from fetal limbs was triple negative for Thy, 6C3, and CD105. The "triple negative" (TN) cell gave rise to CD105+, and Thy and 603+/− cells in vitro and in vivo, and also self renews at least in vitro. Therefore, the TN population was our earliest nomenclature for the mSSC and these results are shown in the microarray transcriptional data. We observed that CD200 appears to refine the colony-forming unit activity of the TN and thus, recent experiments including single cell RNA sequencing were performed on the mSSC with the described immunophenotype in FIG. 2G. Similarly, the immunophenotype of the committed cartilage progenitor (CCP) was refined with the observation of the importance of CD200 in further subfractionation of the skeletogenic stem/progenitor cells.

Transcriptional Expression Profiling. We performed microarray analyses on highly-purified, double-sorted populations of mSSC, BCSP, Thy(+), 6C3(+), HEC and the B-cell lymphocyte stimulating populations (BLSP) of bone marrow mesenchymal stromal cells and HSC, MEP, GMP and CLP. Each population was sorted in independent sorts using cells isolated from postnatal day 3 mice. RNA was isolated with RNeasy Micro Kit (Qiagen, Germantown, Md.) as per manufacturer's instructions. RNA was twice amplified with a RiboAmp RNA amplification kit (Arcturus Engineering, Mountain View, Calif.). Amplified cRNA was streptavidin-labeled, fragmented, and hybridized to Affymetrix 430-2.0 arrays as recommended by the manufacturer (Affymetrix, Santa Clara). Arrays were scanned with a Gene Chip Scanner 3000 (Affymetrix) running GCOS 1.1.1. software. Raw microarray data were submitted to Gene Expression Commons, where data normalization was computed against the Common Reference, which is a large collection (n=11,939) of publically available microarray data from the National Center for Biotechnology Information Gene Expression Omnibus (NCBI GEO). Meta-analysis of the Common Reference also provides the dynamic range of each probe set on the array, and, in situations where there are multiple probe sets for the same gene, the probe set with the widest dynamic range was used for analysis. The Affymetrix Mouse Genome 430 2.0 Array includes 45,101 probe sets, of which 17,872 annotated genes are measurable. Heat maps representing fold change of gene expression were generated in Gene Expression Commons. Pathway-level statistical comparison was performed using Ingenuity Pathway Analysis software (IPA, Ingenuity Systems, Qiagen, Redwood City, Calif.).

Histological analysis of endochondral ossification. Dissected specimens were fixed in 2% PFA at 4° C. overnight, then decalcified in 0.4M EDTA in PBS (pH 7.2) at 4° C. for 2 weeks. Specimens were then processed for embedding in paraffin (by dehydration in alcohol or xylene) or OCT (by cryoprotection in sucrose) and sectioned. Representative sections were stained with freshly-prepared Hematoxylin-and-Eosin, Movat's modified pentachrome, or Alizarin Red stains depending on the individual experiment.

Immunofluorescence. Immunofluorescence on cryopreserved ectopic bone specimens were performed using an M.O.M. immunodetection kit (Vector Laboratories, Burlingame, Calif.) according to manufacturer's instructions. Briefly, specimens were treated with a blocking reagent, then probed with monoclonal antibody at 4° C. overnight. Specimens were next washed with PBS, probed with alexa-dye conjugated antibodies, washed, cover-slipped, and imaged with a Leica DM16000B inverted microscope system. Immunofluorescence on tissue cultured cell specimens were performed similar to cryopreserved specimens using an M.O.M. immunodetection kit (Vector Laboratories, Burlingame, Calif.) according to manufacturer's instructions. Briefly, cultured cells in 6-well to 96-well culture plates were washed with PBS and fixed in 2% PFA at 4° C. overnight. Specimens were treated with a blocking reagent, then probed with monoclonal antibody at 4° C. overnight. Specimens were next washed with PBS, probed with alexa-dye conjugated antibodies, washed, immersed in PBS and imaged with a Leica DM16000B inverted microscope system.

Monoclonal antibodies to the following mouse antigens were obtained from a variety of suppliers (with each respective supplier listed in parentheses following the antigen): mouse collagen 11 (Abcam, Cambridge, Mass.), osteocalcin (Abcam, Cambridge, Mass.), perilipin A (Chemicon/EMD Millipore, Billerica, Mass., USA), CD31 (Abcam, Cambridge, Mass.), CD45 (Biolegend, San Diego, Calif.), Leptin receptor (R&D, Minneapolis, Minn.), gremlin 2 (Biorbyt LLC, San Francisco, Calif.), Foxa2 (Abcam, Cambridge, Mass.), 6C3 (Abcam, Cambridge, Mass.), Thy (Abcam, Cambridge, Mass.), DAPI (Abcam, Cambridge, Mass.) and CD31 (Abcam, Cambridge, Mass.). Alexa-dye conjugated secondary antibodies were purchased from Molecular Probes (Molecular Probes, Eugene, Oreg.).

Cell culture. Skeletal progenitors are cultured in vitro in MEM alpha medium with 10% FCS, 1% Penicillin-Streptomycin under low O2 (2% atmospheric oxygen, 7.5% C O2) conditions. Culture vessels were first coated with 0.1% Gelatin. Cultured cells are lifted for analysis or passaging by incubating with M199 with 2 mg/ml Collagenase 11 (Sigma-Aldrich, St. Louis, Mo.). For mSSC colony forming assays, single cells were sorted into each well of a 96-well plate and cultured for 2 weeks. At this time, specimens were examined under Phase microscopy and a cloning ring was used for quantification. The cells were subsequently lifted for staining and analysis by FACS.

Parabiosis. Parabiosis was performed as described. Briefly, age and sex matched mice of GFP and non-GFP mice of identical B6/Ka background are selected for parabiosis. Mice are anesthetized with inhalational anesthesia. An incision in the skin from the base of the fore-leg to the base of the hind-leg on the right side of one parabiont and the left side of the partner. The fore and hind legs are sutured together at the joints while the dorsal-dorsal, and ventral-ventral folds of the skin flaps are stapled together. Analgesia was administered post-operatively. After two weeks of parabiosis, peripheral samples were collected from the tail and parabiont blood chimerism was assessed by FACS. BMP2-collagen implants were transplanted into the subcutaneous fat of the inguinal fat pad at the third week after peripheral blood chimerism has reached a ratio of 1:1 indicating full fusion of circulatory system between parabionts.

In vivo osteo-induction with BMP2. 10 µg rhBMP2 (R&D Systems, Minneapolis, Minn.) was re-suspended in 30 µl of sterile filtered buffer (30 mM sodium glutamate, 2.5% glycine, 0.5% sucrose, 0.01% Tween 80, pH 4.5) then applied to a collagen sponge (Helistat, Integra Life Sciences, Plainsboro, N.J.) of 3×1.5×1.5 cm dimensions. Sponge was lyophilized and transplanted into anesthetized mice beneath the skin, into the renal capsule, or into the muscles of the posterior thigh.

In vitro culture (TGFβ, BMP-2, TNFα) supplementation assays. Five thousand mSSC (derived from a GFP-labeled mouse) were co-cultured with either regular media [MEM alpha medium with 10% FCS, 1% Penicillin-Streptomycin], or regular media supplemented with either TGFβ (5 ng/mL), BMP-2 (100 ng/mL) or TNFα (10 ng/mL) under low $O_2$ (2% atmospheric oxygen, 7.5% CO2) conditions. 14 days post culture, the cells were lifted using collagenase digestion buffer (as before) for staining and analysis by FACS.

Generation of Conditioned Media from Leptin treated Thy (+), BLSP populations. Ten-thousand freshly isolated Thy (+) and BLSP cells were cultured for three days in regular media until 80% cell confluency was reached. At this stage, the media was changed to serum free media supplemented with the following three recombinant growth factors: IGF (125 ng/mL), FGF2 (100 ng/mL) and Heparin Sulphate (10 U/mL) which was supplemented with or without recombinant leptin (1 µg/mL). The cells were subsequently cultured for 14 days, at which point the conditioned media was collected. 10,000 freshly sorted mSSC were then plated under different conditions: (i) control regular media; (ii) conditioned media from Thy(+) subset treated with leptin; (iii) conditioned media from Thy(+) subset treated with serum-free media; (iv) conditioned media from BLSP subset treated with leptin and (v) conditioned media from BLSP subset treated with serum-free media. These cells were then collected for FACS analysis to determine the number of mSSC present following culture in the experimental/control media.

Quantitative Reverse Transcription Polymerase Chain Reaction. RNA from cultivated cells was extracted using the RNeasy Mini Kit (Qiagen, Valencia, Calif.) according to the manufacturer's protocol. Reverse transcription was performed and gene expression was examined by quantitative real-time polymerase chain reaction (qRT-PCR) using the applied Applied Biosystems Prism 7900HT sequence detection system (Applied Biosystems, Foster City, Calif.) and SYBR Green PCR Master Mix (Applied Biosystems). The amount of PCR product was calculated using external GAPDH standard curve and LightCycler software. All values were normalized based on the GAPDH expression in the corresponding samples. Specific primers for the genes examined (Noggin, Gremlin 2, Leptin Receptor) were based on their PrimerBank sequence.

Inhibition of VEGF signaling. (i) Systemic VEGF inhibition. To study systemic inhibition of VEGF signaling, $10^9$ pfu units of adenoviral vectors encoding the soluble murine VEGFR1 ectodomain (Ad sVEGFR1) was injected intravenously to the designated recipient mice 24 hours prior to transplantation, leading to hepatic infection and secretion of this potent antagonist of VEGF/PlGF signaling into the circulation. For negative control, adenovirus encoding a murine IgG2(Fc immunoglobulin fragment was used (Ad Fc). These reagents are described elsewhere. (ii) Local VEGF inhibition To study local inhibition of VEGF signaling, 50 µg of soluble VEGFR1 (R&D Systems, Minneapolis, Minn.) was placed into the subcutaneous fat of the inguinal fat pad of mice along with a collagen sponge containing 3 µg of lyophilized recombinant BMP2.

Femoral Fracture. An incision was made from the groin crease to the knee of the right femur. Following manual patellar dislocation, a medullary rod was inserted into the femur of anaesthetized 8-week-old C57BL6 wild-type mice. A bicortical transverse mid-diaphyseal fracture was created using a straight micro-scissors. The patella was relocated manually and a suture was placed to prevent subsequent dislocation. The skin incision closed with nylon sutures and the mice received postoperative analgesia. The mice were sacrificed at day 3, day 7 and day 21 post fracture placement. The callus was harvested and the constituent cells were isolated by mechanical and enzymatic dissociation and subsequent FACS fractionation, as detailed above. The uninjured left femur acted as the control, uninjured femur. Hind limb Irradiation 8-week-old C57BL6 mice were placed in a radiation shield, so that only the hindlimbs were exposed to radiation. The mice received a single dose of 800 rads (8Gy) to bilateral hindlimbs. Surgical placement of fracture (as described above) was performed 12 hours post irradiation.

Single Cell RNA Sequencing. Single Cell RNA Sequencing was Performed as Previously Described.

Example 2

Human SSC

As discussed in Example 1, using a transgenic "Rainbow mouse" model (for in vivo tracing of clonally derived tissues), we found that bone, cartilage, and stromal tissues are clonally related in mice. Conversely, we found no evidence that they share the same clonal origins as fat, vessel, or skeletal muscle tissue, implying that bone, cartilage and stromal tissues arise from their own distinct stem/progenitor cells following embryogenesis. Our human skeletal stem/progenitor data demonstrate the existence of the hSSC and its downstream progenitor cells in both fetal and adult skeletal tissue.

Analyses include genomic studies, differentiation potential, lineage tracing performed on fresh isolated primary cells from both fetal and adult human tissue. It was determined that the subcapsular location in the kidney is a novel extra-skeletal site for engraftment of transplanted skeletogenic cells. Incorporating this technique defines a functional assay for examining the fate potential of specific prospectively-isolated cellular subsets of stem/progenitor cells in a mouse study. Subcapsular renal capsule transplantation of cells has previously enabled identification of (i) the minimal cellular components of the bone marrow niche required to support adult HSCs and (ii) a cellular subset from mouse fetal limb bones with the capacity to initiate formation of a fully functional HSC niche. Conditions were optimized for transducing freshly-isolated fetal and adult skeletal progenitors with lentiviral vectors, enabling both surveillance of cellular subsets in a xenograft model and assessment of key genetic pathways using both knock-down and over-expression approaches, technical expertise which is integral to human cell analysis.

Figure 16A:
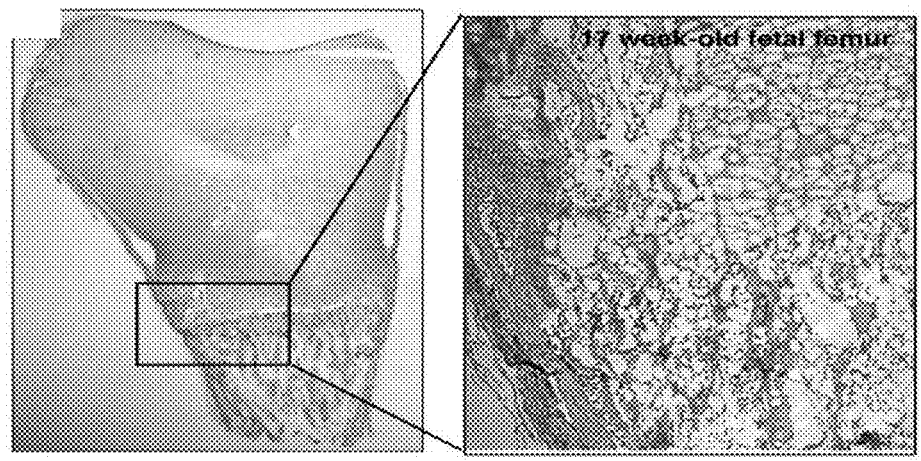
FIG. 16A-16E.
Figure 16B:
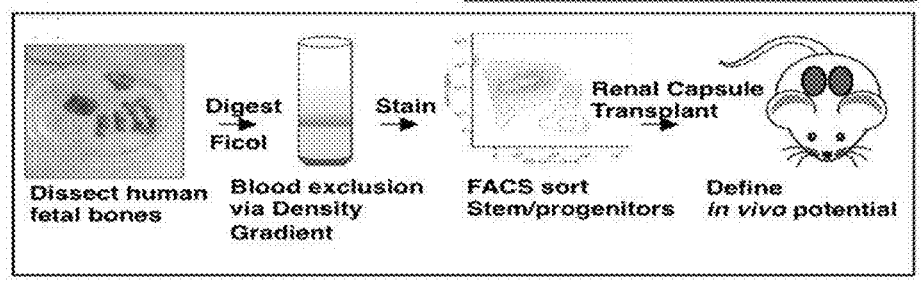
Figure 16C:
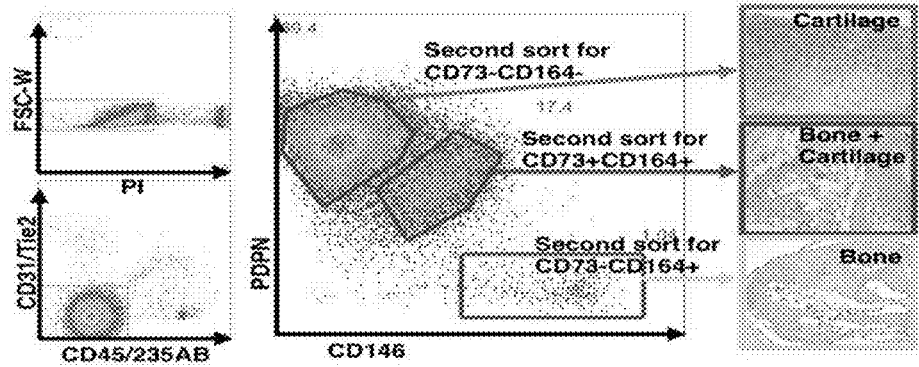

Identification of the human skeletal stem cell (hSSC) and its downstream lineage-restricted progenitors. The strategy described in Example 1 was used to purify specific skeletogenic populations from human fetal skeletal tissue by prospective isolation using FACS. We isolated cells from the growth plates of week 17 human fetal femora by mechanical and enzymatic dissociation and analyzed them for surface markers corresponding to those present on vascular and hematopoietic (CD45, CD235, Tie2, CD31) lineages (FIG. 16a-c). By transplanting dissociated human fetal skeletal cells to mouse renal capsule in immunodeficient mice, we confirmed that only cells negative for CD45, CD235, Tie2, and CD31 possessed intrinsic skeletogenic activity when transplanted in vivo (FIG. 16c Right panel).

Gene expression analysis on [CD45(−)CD31(−)Tie2(−) CD235(−)] dissociated fetal skeletal cells identified additional markers including CD146, PDPN, CD73 and CD164 that further separated human fetal femoral cells into distinct populations, which we then transplanted into the renal capsule to determine their intrinsic skeletogenic potential (FIG. 16b-c). We found that the growth plate had a high frequency of [CD45-CD235-Tie2-CD31-PDPN+CD146-] cells, hereafter referred to as [PDPN+/146-] cells that showed differential expression of CD164 and CD73. Differential expression of these markers further enabled us to subfractionate the [PDPN+/146-] population into three populations: one unipotent subset capable of chondrogenesis [PDPN+CD146-CD73-CD164-], one unipotent cellular subpopulation capable of osteogenesis [PDPN+CD146-CD73-CD164+] and one multipotent [PDPN+CD146-CD73+CD164+] cell capable of endochondral (bone and cartilage) ossification.

Among the distinct populations examined, the [PDPN+CD146-CD73+CD164+] subset selectively gives rise to the highest frequency of colony forming units (CFU). In addition, following in vitro colony formation assays, we find re-isolated [PDPN+CD146-CD73+CD164+] cells from these colonies possess serial CFU forming ability. Thus, our data show that [PDPN+CD146-CD73+CD164+] cells possess the hallmark ability of stem cells to self renew in vitro.

Figure 16D:
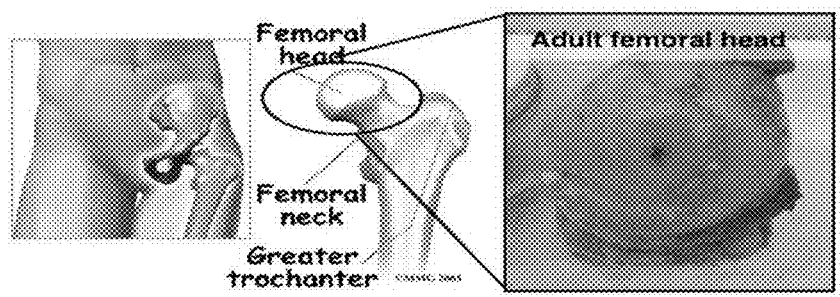
Figure 16E:
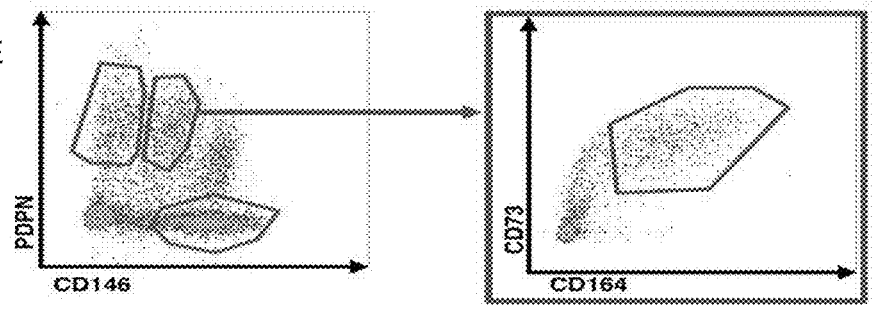

Importantly we found that [PDPN+CD146-CD73+CD164+] cells can be isolated from adult femoral head specimens collected after hip-replacement procedures on 38-73 year old patients. Since hip-replacement procedures are very common and practiced routinely at most major medical centers in the world, femoral head specimens constitute a readily accessible source for material to engage in SSC research and for clinical use (FIGS. 16d and e). Both fetal and adult derived [PDPN+CD146-CD73+CD164+] cells are capable of giving rise to all other skeletal subsets in vitro (FIG. 17a-b).

We have further tracked the clonal skeletogenic activity of [PDPN+CD146-CD73+CD164+] hSSC in vivo. We followed in vivo clonal formation from hSSCs that were transduced with lentiviral gene ontology (LeGO) vectors encoding red, green or blue (RGB) fluorescent proteins. In accordance with the additive color model, individual RGB-marked cells display a large variety of unique and highly specific colors. Color codes remain stable after cell division and thus, facilitate clonal tracking in vivo and in vitro (FIG. 17c). The data demonstrate that hSSCs following lentiviral transduction can form clones both in vitro and in vivo (FIG. 17d-e).

The human data from both fetal and adult tissue indicate a self-renewing clonal precursor of bone, cartilage and stroma (hSSCs, hSSCs) in vitro, defined by the following immunophenotype [PDPN+CD146-CD73+CD164+]. Results indicate that human skeletogenic progenitors are diverse, with distinct surface marker profiles and skeletal fates, as in hematopoiesis. Adult and fetal derived hSSCs are prospectively isolated for functional analysis by transplantation to the renal capsule to assay their intrinsic skeletogenic potential, and also to the femoral cavity of immunodeficient mice to re-evaluate their differentiation potential in the context of a normal skeletogenic microenvironment.

The Gene Expression Commons platform normalizes RNA microarray data against the Common Reference, which is a large collection (n=11,939) of publicly available microarray data from the National Center for Biotechnology Information Gene Expression Omnibus. This innovative algorithmic system enables identification of additional cell surface markers to correlate osteoblastic, chondrogenic, or fibroblastic-associated genes with specific surface marker proteins. These markers can resolve distinct progenitor subsets with characteristic colony-forming capabilities and developmental fates. The developmental fate of newly resolved skeletogenic progenitor cells in the human SSC lineage map to differentiate into skeletal tissue in vivo is determined by transplanting them beneath the renal capsule in a mouse xenograft model. Freshly-isolated skeletal stem/progenitor cells are transduced with lentiviral vectors and the clonality of each transplanted cell followed in vivo (FIG. 17d).

Figure 18:
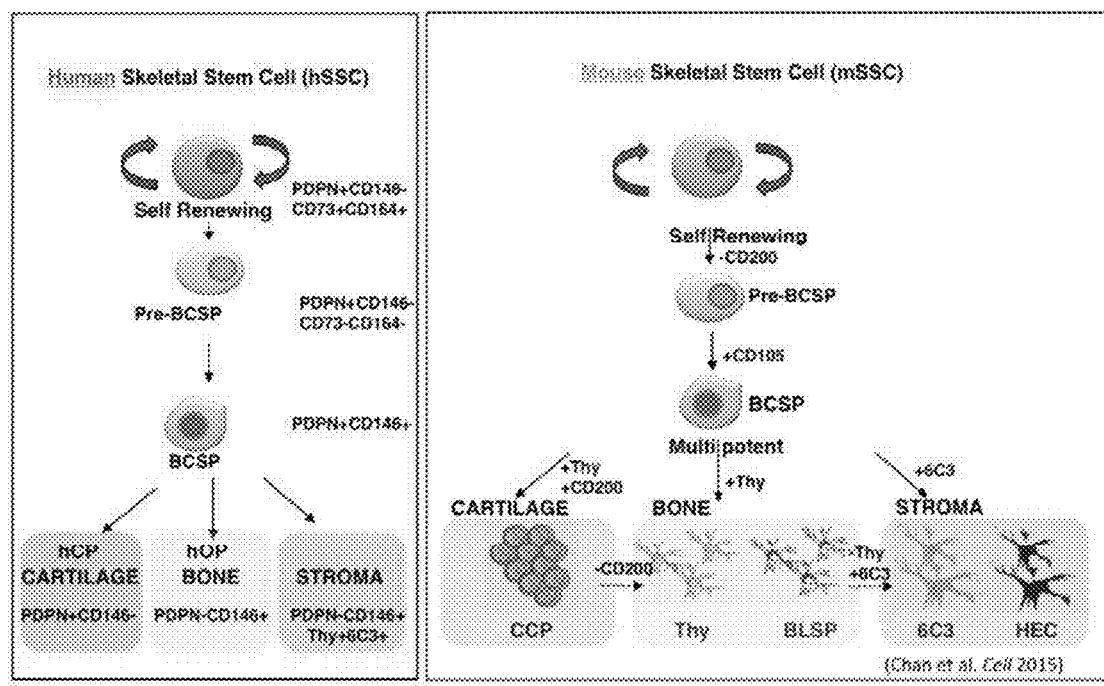
FIG. 18. Lineage maps of hSSC (left) vs mSSC (right). (pre) BCSP=(pre) bone, cartilage and stromal progenitor cell; hCP=human chondrogenic progenitor; hOP=human osteogenic progenitor.

The hSSC [PDPN+CD146-CD73+CD164+] are predicted to linearly generate all of the progenitor subpopulations through a sequence of stages both in vitro and in vivo (FIG. 18). To evaluate the comparative potential of individual human skeletal progenitor subsets to generate a downstream subtype, FACS purified, lentivirally-labeled stem and progenitor cells from femora at 17 weeks gestation and adult femoral heads are tested both (i) in vitro and (ii) in vivo.

In vitro: Individual lentivirally-labeled freshly sorted hSSCs are transplanted (along with 5,000 non-labeled dissociated fetal bone cells as feeder) into renal capsule for a period of 14 days, at which point they are explanted, re-fractionated by FACS and subsequently re-transplanted beneath the renal capsule for functional readout. Data indicate that hSSCs both self-renew and differentiate on serial colony forming assays (FIGS. 17d and e). The hSSC, following single-cell plating, are expected to (i) generate the downstream progenitors linearly and (ii) both self-renew and differentiate on serial colony forming assays, in keeping with stem cell characteristics.

In vivo: 2,000 freshly-isolated fetal and adult hSSCs are transplanted into the renal capsule of RAGγ mice, then engrafted progenitors are explanted 2/4/8 weeks or 6 months post transplant for analysis. Data indicate that primitive xenografted human skeletal progenitors can generate mature bone, cartilage, and stromal cells capable of supporting HSCs within 4 weeks of transplant beneath the renal capsule. The developmental fate of the human grafts is shown by histological analysis using Movat's Pentachrome staining which differentiates bone, cartilage, and stromal tissues (FIG. 16c). To better correlate the phenotypic outcome of transplanted cells, with the appearance of distinct FACS-defined skeletal subsets, explanted graft tissue are dissociated and analyzed by FACS.

Experimental Methods:

Isolation of fetal human skeletal progenitors using fluorescence activated cell sorting (FACS): Human fetal tissue at 17 weeks gestation are purchased from StemExpress (Placerville, Calif., USA). Human fetal limb bones are dissected, serially digested in collagenase digestion buffer supplemented with DNase at 37° C. for 40 min under constant agitation and total dissociated cells are filtered through 40 mm nylon mesh, pelleted at 200 g at 4° C., resuspended in staining media (2% fetal calf serum in PBS), and stained with fluorochrome-conjugated antibodies for CD45, CD235ab, Tie2, CD31, CD146, PDPN, CD73, CD164 for FACS analysis on a FACS Aria II Instrument (BD Biosciences, San Jose, Calif.) using a 70 μm nozzle.

Isolation of adult Skeletal Progenitors using fluorescence activated cell sorting (FACS): Discarded femoral head tissues from hip replacement procedures are obtained from Stanford's Orthopedic Surgery Service. Skeletal tissue is removed from different regions of the femoral head mechanically including the marrow cavity and then serially digested in collagenase digestion buffer supplemented with DNase at 37° C. for 40 min under constant agitation and total dissociated cells are filtered through 40 mm nylon mesh, pelleted at 200 g at 4° C., resuspended in staining media (2% fetal calf serum in PBS), and stained with fluorochrome-conjugated antibodies for CD45, CD235ab, Tie2, CD31, CD146, PDPN, CD73, CD164 for FACS analysis on a FACS Aria II Instrument (BD Biosciences, San Jose, Calif.) using a 100 μm nozzle.

Cell culture: Skeletal progenitors are cultured in vitro on pre-coated (0.1% gelatin) culture vessels in MEMα medium with 20% FCS under low $O_2$ (2% atmospheric oxygen, 7.5% $CO_2$) conditions. Cells are lifted for analysis/passaging by incubating with collagenase digestion buffer followed by neutralization of collagenase enzymatic activity with staining media and final centrifugation.

In vitro colony formation assays: Populations of hSSCs are FACS-sorted prior to single cell culturing, as described above. hSSC colony forming units are identified using an inverted microscope under 40× magnification. Colonies are assessed for size and cell morphology.

Microarray analyses of highly purified populations of human skeletal progenitors: Each cellular subpopulation is obtained by FACS from limbs of a human fetus at 17 weeks gestation or adult femoral heads for RNA extraction for microarray analysis, using techniques published by our laboratory and repeated in triplicate (three different samples) to ensure maximal accuracy. RNA is isolated with RNeasy Micro Kit (Qiagen) per manufacturer's instructions. mRNA amplification is performed using a two-cycle target labeling system for 3' in vitro transcription, hybridized to a human genome U133 plus 2.0 array, and scanned according to the manufacturer's protocol (Affymetrix). Background correction and signal normalization is performed using the standard multichip average algorithm.

Microarray analysis using Gene Expression Commons (GEXC): Raw data obtained from microarray analysis is uploaded to GEXC, a system created our laboratory to mine datasets. The GEXC platform normalizes RNA microarray data against the Common Reference, (a large collection (n=11,939) of publicly available microarray data from the National Center for Biotechnology Information) and generates heat maps representing fold change of gene expression. GEXC analysis also provides an intuitive user-friendly interface to conduct differential expression analysis to identify genes that are selectively up-regulated in one population and not another.

Transplantation of fetal and adult cells beneath the kidney capsule of immunodeficient mice: Kidney capsule transplants are performed as previously published. Briefly, under general anesthesia, blunt dissection is performed to identify the kidney of an immunocompromised RAGγ mouse. RAGγ mice are immunodeficient due to homozygous deletions of the Rag2 polymerase and the IL2 receptor which are necessary for formation of mature B, T, and NK cells. A small renal capsulotomy using a 25 gauge needle allows insertion of the blunt injection cannula and 2,000 cells suspended in Matrigel are placed beneath the renal capsule. Formation of a visible bulla between the renal parenchyma and capsule and lack of significant bleeding or extra-renal leakage of injected cells are criteria used for successful injection. The overlying tissue and skin above the kidney is then sutured for closure. Grafts will be explanted using a dissection microscope at 2/4/8 weeks or 6 months post placement and is analyzed by FACS following enzymatic digestion and subsequent mechanical dissociation of cells or by histological analysis.

In vitro Skeletal Progenitor Differentiation Assays: Freshly isolated skeletal progenitors are fluorescently labeled with lentiviral vectors as described. This process makes use of the simultaneous transduction of target cells with three lentiviral gene ontology (LeGO) vectors encoding red, green or blue (RGB) fluorescent proteins. In accordance with the additive color model, individual RGB-marked cells display a large variety of unique and highly specific colors. Color codes remain stable after cell division and thus, facilitate clonal tracking in vivo and in vitro (FIG. 17c-d). After 8 hours of transduction, distinct transduced populations are isolated by FACS then co-cultured either with unsorted/unlabeled total progenitor populations, by themselves, or with distinct FACS-isolated fractions together in MEMα medium.

In vivo Skeletal Progenitor Differentiation Assays: After transduction, FACS-isolated populations are embedded in Matrigel (Corning, N.Y.) and transplanted beneath the renal capsule as above. Matrigel localizes the transplanted cells under the renal capsule. One month after transplant, grafts are explanted from recipient mouse kidneys, and dissociated (enzymatically and mechanically) for analysis by FACS. Portions of explanted grafts are fixed and prepared for histological analysis Histological analysis: Dissected specimens are fixed, decalcified and embedded in paraffin or OCT for sectioning and staining for endochondral ossification using Movat's Pentachrome staining. We evaluate potential non-skeletal fates generated by our transplanted purified populations by immuno-staining, with specific differentiation markers for adipocytes and fibrocytes, such as adiponectin and smooth muscle actin, respectively.

Example 3

Stem cell fate is influenced by the specialized microenvironment or "niche", in which the cells reside (FIG. 19a-b). Modulating niche signaling can stimulate tissue growth by inducing proliferation of stem cells, as we have observed with mSSCs. Niche interactions may also play significant roles in maintaining lineage commitment; for instance, increased local BMP2 signaling can promote expansion and survival of mouse SSC. Microarray data on hSSC demonstrated conservation of genes involved in BMP, WNT, and VEGF signaling which we observed were involved in survival, proliferation, and differentiation of mSSC (FIG. 19c-e). Thus, a system of autocrine and paracrine signaling in the niche microenvironment of hSSCs, regulates their expansion, activity and differentiation (FIG. 19b). The application of specific exogenous morphogens such as BMP2, WNT and VEGFA can mimic niche signaling, leading to survival, and/or proliferation, of hSSC in minimal conditions. Alternatively, other combinations of BMP2, WNT or VEGF may promote differentiation of SSC towards specific skeletal fates, such as bone, cartilage or stroma.

Comparative microarray analysis on FACS-purified human skeletal stem/progenitor cells identifies specific genes that are distinctly upregulated in hSSCs and crude progenitor populations. Data illustrate high transcriptional expression of BMP2 in hSSCs, reflecting that seen in our mouse study (FIG. 19d). In addition, high transcriptional expression of genes implicated in WNT and VEGF dependent signaling pathways is seen in hSSCs and their downstream-derived progenitor cells, similar to our findings on mouse skeletal progenitors (FIG. 19e). Conversely we observed reduced expression of VEGF in the hCP (human chrondrogenic progenitor subset). This is consistent with the observation that VEGF antagonism promotes chondrocyte differentiation by endogenous and induced mouse SSC (FIG. 20e). BMP2, WNT and VEGF pathways are highly involved in regulating expansion, formation, and differentiation of mouse and human SSC (FIG. 19f).

It is determined whether human progenitor subsets can maintain survival and proliferation of hSSC in minimal conditions. In vitro: co-culturing lentivirally-fluorescent (e.g. GFP) labeled stromal subsets with freshly harvested hSSCs in serum-free conditions that have been labeled with a different color (e.g. RFP). After two weeks period of co-culture, the relative percentages of hSSCs are determined by FACS to determine the capacity of a particular stromal subset to maintain survival and proliferation of human skeletal stem/progenitor cells in minimal conditions. In vivo: The ability of distinct stromal fractions to affect hSSC activity is directly tested in vivo, by co-transplanting 100-200 differentially fluorescent-protein labeled hSSC with distinct stromal subsets beneath the renal capsule of RAGγ mice, and then by explanting the engrafted tissue one month later for dissociation and analysis by FACS/histology. We transplant 100-200 hSSCs in this assay. Systematic profiling of distinct progenitor subtypes allows identification of the minimal in vivo conditions required for survival/proliferation of the human stem/progenitor cells. Distinct human skeletal progenitor subsets maintain survival and proliferation of hSSCs in minimal conditions.

Role of BMP2, WNT3A, and VEGF, either alone or in combinations to regulate maintenance, expansion and differentiation of human fetal and adult skeletal stem/progenitor cells in minimal conditions in vitro and in vivo. The role of distinct hSSC niche pathways is evaluated directly using commercially available purified recombinant factors (BMP2, WNT and VEGF) by administering them to hSSCs in culture (in serum free media) either as single agents or in specific combinations matching the presentation of their specific cognate receptors on hSSCs, as shown by microarray analysis through GEXC. The expression of key genes involved in BMP2, WNT, and VEGF pathways is validated using single cell RNA sequencing (FIG. 19f).

In vivo: Combinations of these factors are tested on hSSCs, by transplanting hSSCs in direct combination with a depot of BMP2, WNT and VEGF(s). To evaluate the activity of candidate combinations of BMP2, WNT and VEGF in situ, and the role of the intact hSSC environment as potential modifying effects of skeletal matrix, intact xenografted human fetal bones established following transplants of intact fetal limb anlages (e.g. phalanges), are implanted subcutaneously with a small catheter connected to an implantable osmotic pump which administers the BMP2, WNT and VEGF or a solvent/PBS control in a rate controlled constant daily delivery (rather than supraphysiological depot delivery which can result in burst release of the morphogen(s)). Treated and untreated human fetal limbs are assayed for gross morphology and by histology or dissociated for FACS analysis to determine shifts in the relative abundance of hSSCs and downstream skeletal subsets.

The critical signaling pathways in a particular hSSC-niche interaction are further evaluated using lentivirally mediated silencing of either the signaling ligand expression in the stromal cells or its corresponding receptor in hSSCs.

Experimental Methods:

Lentiviral labeling of hSSCs for in vitro and in vivo co-culture with stromal subsets: hSSCs are fluorescently-labeled by transfection with (GFP, RFP or CFP) lentiviruses. After 8 hours of transduction, distinct GFP, RFP or CFP transduced populations are isolated by FACS. This enables observation of the functional interaction between hSSCs and stromal populations both in vitro and in vivo.

Microarray analyses of highly purified populations of human skeletal progenitors: is performed and data is analyzed using GEXC. Using GEXC cell-cell interactions between the hSSC and other cellular components of the skeletal niche are mapped. Stromal cells that express ligands or are involved in BMP, WNT and VEGF signaling are identified.

Single cell gene expression analysis by single cell RNA sequencing: To determine the expression patterns of BMP2, WNT, and VEGF pathway genes at a single cell level, isolated purified hSSC utilize the C1 microfluidic system (Fluidigm) to capture single cells per well. The C1 system uses a microfluidic circuit to capture single cells followed by cell-lysis, RNA isolation, cDNA preparation, and amplification of the cDNA in a fully automated fashion. Libraries are prepared using amplified cDNA from individual cells using Nextera-XT kit (Illumina) and sequenced using Nextseq-500 platform (Illumina) to obtain ~10-15 million 2×150 base-pair pair-end reads per cell.

Co-culture of hSSC with stromal subsets: Lentivirally transduced differentially fluorescently-labeled stromal subsets and freshly harvested hSSCs are co-cultured in serum-free conditions. After one week of co-culture, the relative percentages of hSSCs are determined by FACS to determine the capacity of a particular stromal subset to maintain survival and proliferation of hSSC in minimal conditions.

FACS analysis of hSSC behavior in the presence of stromal subset(s): After one week of co-culture (of differentially fluorescently labeled hSSC and distinct stromal progenitors), the relative percentages of hSSCs is determined by FACS analysis, then resorted and transplanted in vivo to determine if specific stromal cell subtype(s) can maintain, amplify, or differentiate hSSCs down particular skeletal lineages in vivo.

Transplantation of cells beneath the kidney capsule of immunodeficient mice: Direct co-transplantation assay: 100-200 hSSCs are directly co-transplanted in vivo with stromal subset(s) found to affect hSSC when assayed in vitro. Grafts are explanted and analyzed by FACS.

Use of cytokine factors to assess gene function in vitro and manipulate the function of cells in vivo: To assess gene function in vitro and to assess the role of key regulatory genes identified, hSSCs are co-cultured in the presence of cytokine growth factors (e.g. BMP2, WNT and VEGF). Optimal concentrations of these cytokine growth factors is determined per manufacturer's recommendation according to the measured activity level per batch of growth factors. Colony formation assays allow measuring the effects of particular combinations of BMP2, WNT and VEGF to regulate hSSC expansion, differentiation and survival.

Gene silencing in hSSCs and stromal subsets using lentivirus: To assess the role of the specific genes that are differentially regulated and necessary for regulating the niche in the interaction between the hSSC and cellular components of the niche, genes involved in BMP2, WNT and VEGF signaling are silenced using shRNA lentiviral-mediated suppression of genes. The critical signaling pathways in a particular hSSC niche interaction is evaluated using lentivirally mediated silencing of either the signaling ligand expression in the stromal cells or its corresponding receptor in hSSCs.

Manipulation of hSSCs with recombinant morphogens in vitro and in vivo: Identification of key regulatory pathways that control hSSC differentiation fate is identified using microarray analyses as described above. This allows identification of a combination of cytokine growth factors such as BMP2, WNT and VEGF for in vitro and in vivo analysis with hSSCs. Cells are co-cultured with recombinant BMP2, WNT and VEGF and two weeks later cells are (i) analyzed using FACS or (ii) transplanted beneath the renal capsule of immunodeficient mice. After one month these grafts are explanted to assess the role of the cytokines on hSSC differentiation and proliferation, using combinations of histology and immunofluorescence. Recombinant morphogen(s) effects are tested on hSSCs in vivo, by co-transplanting morphogen depots with hSSCs for instance by implanting hydrogels that slowly-release BMP2, WNT and VEGF.

Transplantation of fetal limb anlages: Fetal limb anlages are isolated from the phalanges of a human fetus at 10-12 weeks gestation. Under anesthesia, anlages are transplanted to the dorsal subcutaneous space of a RAGγ mice mouse. After 1 month, anlages are explanted and morphology is assessed using histology.

Cytokine delivery to fetal anlages in vivo: Patterning and growth of the xenografted human fetal limb anlage is manipulated by delivering cytokine growth factors (e.g. BMP2, WNT and VEGF) locally using a subcutaneous osmotic pump. Pumps are purchased from Alzet (Cupertino, Calif.). To establish subcutaneous human fetal bone xenografts, human bone anlage are dissected from 10-12 week gestational age human fetal tissue purchased from StemExpress (Placerville, Calif., USA). Dissected anlages are transplanted subcutaneously and secured in place with single suture. Catheter of osmotic pump are placed alongside graft and also secured using single suture. Following one month of treatment, anlages will be explanted for analysis by histology and immunofluorescence. The effects of cytokine treatment are functionally assessed by comparing with anlages that have not been treated with cytokines.

Histology & Immunofluorescence (IF): IF on cryopreserved ectopic bone specimens is performed using a M.O.M. immunodetection kit from Vector Laboratories (CA) as previously describe. Briefly, specimens are treated with a blocking reagent; probed with monoclonal antibody at 4° C. overnight; washed with PBS; probed with alexa dye conjugated antibodies; washed; coverslipped; and imaged with a Leica DMI6000B inverted microscope system. IF on tissue cultured cell specimens is performed similarly to that used for cryopreserved specimens. (Image analysis: confocal microscopy, Zeiss 780 confocal system).

Systemic inhibition of vascular signaling: To study the effect of VEGF inhibition on skeletal niche regulation and specifically on chondrogenic fate promotion, $10^9$ pfu units of adenoviral vectors encoding the soluble murine VEGFR1 ectodomain (Ad sVEGFR1) are injected intravenously to the designated recipient mice 24 hours prior to transplantation, leading to hepatic infection and secretion of this potent antagonist of VEGF signaling into the circulation. For negative control, adenovirus encoding a murine IgG2a Fc immunoglobulin fragment is used (Ad Fc). Grafts are explanted 3 weeks post-transplantation.

Example 4

Figure 21:
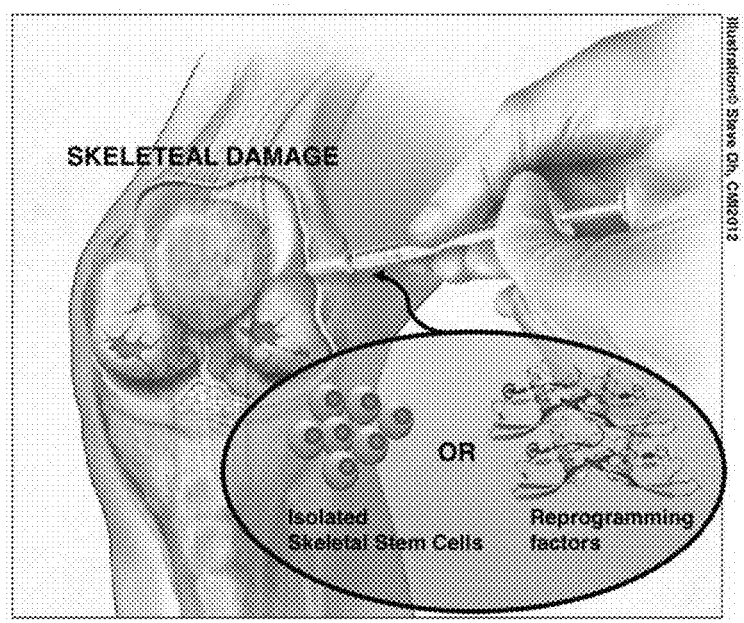
FIG. 21. Next generation stem-cell based skeletal regenerative medicine.

Conditions for efficient in situ reprogramming of human adipose tissue into bone, cartilage, or bone marrow stroma. Inducing SSC formation with soluble factors and subsequently regulating the SSC niche to specify its differentiation towards bone, cartilage, or stromal cells represents a paradigm shift in the therapeutic regeneration of skeletal tissues. In situ induction of SSC formation is possible in mouse adipose tissue, and BMP2 can trigger in situ induction of SSC formation in human adipose tissue (FIG. 20a-c). This therapeutic modality extends the ability to treat skeletal defects or degeneration even when resident levels of endogenous SSCs have been depleted by disease or aging. Fat is naturally abundant and offers a readily available source of mesenchymal cells that can be reprogrammed into skeletal progenitors. This strategy has enormous translational potential for skeletal diseases, such as osteoarthritis and osteoporosis (FIG. 21).

Specific concentrations of BMP2 can trigger activation of skeletogenic transcriptional programs in non-skeletal mesenchymal cells residing in adipose tissue, as seen in mouse. These adipose-derived induced SSCs (iSSCs) can then be directed with additional factors (WNT, VEGF) towards specific skeletal fate (e.g. bone, cartilage, or bone marrow stroma) for in situ skeletal tissue therapeutic regeneration. Delivery of adipose derived stromal cells with combinations of SSC-inducing BMP2 and SSC-specifying niche factors such as (WNT, and VEGF) will maximize induced skeletal tissue formation at injury sites.

Human adipose derived stroma express BMPR1B indicating they are responsive to BMP2 signaling (FIG. 20a, top). Unsorted hematopoietic depleted human adipose stromal cells (hASCs) effectively form bone when transplanted with 0.3 mg/ml BMP2 in Ragγ mice subcutaneously (FIG. 20c). These data support the use of BMP2 to induce hSSC in adipose-derived cells.

RhBMP2 protein can induce SSC formation in adipose tissue (i) in situ in mice or (ii) when hASCs are co-transplanted with BMP2 (FIG. 20c). The optimum concentration of BMP2 necessary to induce formation of hSSC in hASCs is determined: following hematopoietic cell depletion by magnetic activated cell sorting, $10^6$ freshly isolated hASCs are resuspended in matrigel containing increasing concentrations of rhBMP2, (from 1 µg/ml to 1 mg/ml), in a total final volume of 20 µl for subcutaneous transplantation into RAGγ actin-CFP transgenic mice. Grafts are explanted at weekly intervals for histological analysis by Movat's Pentachrome and FACS for human skeletal progenitors. BMP2-induced mSSC undergo endochondral ossification leading to cartilage formation in the first week and bone/marrow formation by the fourth week. Grafts are explanted at weekly intervals to determine the pace of induced bone formation per concentration of BMP2 assayed. After determining the optimum concentration of BMP2 to induce bone, 100× activity unit per batch are co-injected with of other skeletal-modulatory factors (e.g. VEGFR, WNT) to determine the capacity to pursue BMP2-induced chondrogenesis or bone (FIGS. 20d and e).

Multiple distinct cell types in adipose tissue may be capable of undergoing BMP2-induced skeletogenesis. Resolving the identity of these cell types in human adipose tissue could elucidate the mechanism of BMP2-mediated osteo-induction and reveal new directions to engineer this response to regenerate diseased or damaged skeletal tissue. Distinct subsets of hASCs express BMPR indicating they are responsive to BMP-mediated signaling. Following supplementation of media with BMP2, hASCs are induced to express several of the defining markers identified on hSSC and downstream progenitor (hBCSP) subset including PDPN and CD146 (FIG. 20a). To determine if BMPR defines cells competent to undergo skeletogenesis, distinct populations of BMPR expressing subsets are isolated by FACS and co-transplanted with BMP2 in matrigel into RAGγ CFP mice subcutaneously. Grafts are explanted four weeks after transplant as this corresponds to the time when BMP2-induced skeletogenesis in vivo reaches its peak. Samples are analyzed histologically by Pentachrome staining. Murine versus human tissue is ascertained through CFP expression. Staining with human nuclear antigen could supplant negative CFP expression to mark human tissue as required. It is expected that BMP2-induced skeletogenesis correlates with the degree of BMPR expression.

Experimental Methods:

Isolation of hASCs: hASCs are freshly isolated from lipoaspirate from healthy patients undergoing elective lipoaspiration of the abdomen, flank, and/or thigh region, as previously described.

Magnetic Activated Cell Sorting: hASCs are incubated with CD45 and CD235 antibodies conjugated to magnetic beads (Miltenyi Biotech, San Diego, Calif.) for 20 minutes at 4° C. under continuous rotation. The cells are passed through a magnet in order to deplete the hASCs of hematopoietic cells. This procedure enriches fresh lipoaspirated tissue for stromal cells prior to further separation by FACS.

Supplementation of hASC with rhBMP2 in vitro: hASCs are isolated as above and cultured in the presence of increasing concentrations of rhBMP2 from 1 µg/ml to 1 mg/ml.

Subcutaneous Transplantation of hASCs with increasing concentrations of rhBMP2: Freshly depleted hASCs ($10^6$) are resuspended in matrigel with increasing concentrations of rhBMP2 from 1 µg/ml to 1 mg/ml in a total volume of 20 µl for subsequent subcutaneous transplantation into the inguinal fat pad of RAGγ actin-CFP transgenic mice. Grafts are explanted at weekly intervals for histological analysis by Movat's Pentachrome and FACS for human skeletal progenitors.

Isolation of hASCs expressing BMPR1a, BMPR1b, BMPR2: hASCs are isolated as above and resuspended in staining media (2% fetal calf serum in PBS), and stained with fluorochrome-conjugated antibodies for BMPR1a/BMPR1b/BMPR2 for FACS analysis on a FACS Aria II Instrument (BD Biosciences, San Jose, Calif.).

What is claimed is:

1. A method for regenerating articular cartilage in a human individual, the method comprising:
   administering to the individual at a site where regeneration of articular cartilage is desired, a combination of an effective dose of human adipose-derived stem cells (hASC) that express BMP receptor (BMPR1); human BMP2 protein in a dose effective to reprogram the ASC to $CD45^-CD235^-Tie2^-CD31^-PDPN^+CD146^-CD73^+$ CD164+ human skeletal stem cells (hSSC); and a VEGF inhibitor in a dose effective to induce a chondrogenic fate in the hSSC;
   wherein articular cartilage is regenerated at the site.

2. The method of claim 1, wherein the combination of cells, BMP2 and VEGF inhibitor are provided in a matrix.

3. The method of claim 1 wherein the cells are autologous to the individual.

4. The method of claim 1 wherein the cells are allogeneic to the individual.

5. The method of claim 1, wherein the cells are freshly isolated from lipoaspirate.

6. The method of claim 2, wherein the matrix is a scaffold, paste or implant, and wherein articular cartilage is formed at the site of the matrix.

7. The method of claim 1, wherein the VEGF inhibitor is an antibody that specifically binds to human VEGF.

8. The method of claim 1, wherein the VEGF inhibitor is a soluble VEGF receptor.

9. The method of claim 1, wherein the VEGF inhibitor is selected from: ABT-869; AEE-788; AG-13736; AG-028262; Angiostatin; bevacizumab; AVE-8062; AZD-2171; sorafenib; BMS-387032; CEP-7055; CHIR-258; CP-547632; 786034; GW-654652; IMC-1C11; KRN-951; PKC-412; benzoylstaurosporine; CGP-41251; midostaurin; STI-412; PTK-787; vatalanib; sunitinib; semaxanib; SU-666; VEGF Trap; Thalidomide; XL-647; XL-999; XL-880; ZD-6474; and ZK-304709.

10. The method of claim 2, wherein the matrix is a biodegradable matrix comprised comprising one or more of matrigel, polylactic acid, polyglycolic acid, poly(lactic-co-glycolic acid); collagen, and alginate.

11. The method of claim 5, wherein the hASC are isolated by selecting for cells that express BMPR1.

12. The method of claim 5, wherein the hASC are isolated by depleting lipoaspirate of hematopoietic cells.

13. The method of claim 1 wherein following the administering steps, an articular cartilage mass of the treated individual is increased at least 50% relative to an untreated control.

14. A method for regenerating articular cartilage in a human individual, the method comprising:
isolating human adipose stem cells (hASC) from lipoaspirate by negative selection for CD45 and CD235; and positive selection for expression of BMP receptor (BMPR1);
administering to the individual at a site where regeneration of cartilage is desired, a composition consisting of human BMP2, wherein human BMP2 is provided at a concentration from 1 mg/ml to 1 mg/ml; an effective dose of the isolated human adipose-derived stem cells (hASC) that express BMP receptor (BMPR1) to reprogram the ASC to human skeletal stem cells (hSSC), and the VEGF inhibitor is administered in a dose effective to induce a chondrogenic fate in the hSSC;
wherein following the administering steps, the articular cartilage mass is increased at least 50% relative to an untreated control.

15. The method of claim 14 wherein the cells, BMP2 and VEGF inhibitor are provided in a matrix.

16. The method of claim 15, wherein the matrix is a scaffold, paste or implant, and wherein articular cartilage is formed at the site of the matrix.

17. The method of claim 2, wherein the matrix is a biodegradable matrix comprised comprising one or more of matrigel, polylactic acid, polyglycolic acid, poly(lactic-co-glycolic acid); collagen, alginate.

18. The method of claim 14, wherein the VEGF inhibitor is an antibody that specifically binds to human VEGF.

19. The method of claim 14, wherein the VEGF inhibitor is a soluble VEGF receptor.

\* \* \* \* \*

UNITED STATES PATENT AND TRADEMARK OFFICE
CERTIFICATE OF CORRECTION

| | |
|---|---|
| PATENT NO. | : 11,083,755 B2 |
| APPLICATION NO. | : 15/538894 |
| DATED | : August 10, 2021 |
| INVENTOR(S) | : Charles K. F. Chan et al. |

It is certified that error appears in the above-identified patent and that said Letters Patent is hereby corrected as shown below:

In the Specification

Please add the "STATEMENT OF GOVERNMENT SUPPORT" with the following text:
-- This invention was made with Government support under contracts DK115600 and HL058770 awarded by the National Institutes of Health. The Government has certain rights in the invention. --

Signed and Sealed this
First Day of October, 2024

*Katherine Kelly Vidal*

Katherine Kelly Vidal
*Director of the United States Patent and Trademark Office*